United States Patent
Cook

(10) Patent No.: US 6,804,661 B2
(45) Date of Patent: Oct. 12, 2004

(54) DRUG PROFILING APPARATUS AND METHOD

(75) Inventor: Daniel R. Cook, Bountiful, UT (US)

(73) Assignee: Bright Ideas, L.L.C., Bountiful, UT (US)

( * ) Notice: Subject to any disclaimer, the term of this patent is extended or adjusted under 35 U.S.C. 154(b) by 643 days.

(21) Appl. No.: 09/894,440

(22) Filed: Jun. 28, 2001

(65) Prior Publication Data

US 2002/0059159 A1 May 16, 2002

Related U.S. Application Data

(63) Continuation-in-part of application No. 08/840,052, filed on Apr. 24, 1997, now Pat. No. 6,546,378.
(60) Provisional application No. 60/214,624, filed on Jun. 28, 2000.

(51) Int. Cl.[7] .............................. G06E 3/00; G06F 15/18
(52) U.S. Cl. .............................. 706/20; 706/12; 706/16
(58) Field of Search .............................. 706/20, 12, 16

(56) References Cited

U.S. PATENT DOCUMENTS

| | | | |
|---|---|---|---|
| 4,883,067 A | 11/1989 | Knispel et al. | 600/545 |
| 5,222,210 A | 6/1993 | Leivian | 706/11 |
| 5,253,332 A | 10/1993 | Kumamoto | 706/52 |
| 5,255,347 A | 10/1993 | Matsuba et al. | 706/25 |
| 5,353,380 A | 10/1994 | Zhang | 706/52 |
| 5,355,435 A | 10/1994 | DeYong et al. | 706/26 |
| 5,377,100 A | 12/1994 | Pope et al. | 600/545 |
| 5,379,268 A | 1/1995 | Hutson | 367/100 |
| 5,402,521 A | 3/1995 | Niida et al. | 706/20 |
| 5,434,955 A | 7/1995 | Kumamoto | 706/52 |
| 5,465,321 A | 11/1995 | Smyth | 706/20 |
| 5,470,081 A | 11/1995 | Sato et al. | 463/36 |
| 5,474,082 A | 12/1995 | Junker | 600/545 |
| 5,485,551 A | 1/1996 | Ejima et al. | 706/52 |
| 5,515,477 A | 5/1996 | Sutherland | 706/41 |
| 5,524,176 A | 6/1996 | Narita et al. | 706/2 |
| 5,571,057 A | 11/1996 | Ayers | 463/36 |
| 5,579,439 A | 11/1996 | Khan | 706/2 |
| 5,583,771 A | 12/1996 | Lynch et al. | 701/36 |
| 5,617,513 A | 4/1997 | Schnitta | 706/14 |
| 5,651,100 A | 7/1997 | Hayashi et al. | 706/52 |
| 5,687,286 A | 11/1997 | Bar-Yam | 704/232 |
| 5,797,395 A * | 8/1998 | Martin | 600/486 |
| 5,819,242 A | 10/1998 | Matsuoka et al. | 706/2 |

OTHER PUBLICATIONS

J.J. Rajan and P.J.W. Rayner, "Time Series Classification Using the Volterra Connectionst Model and Bayes Decision Theory," IEEE Int'l Conf. on Acoustics, Speech and Signal Processing, vol. 1, pp. 601, 604.

NeuralWare Brochure, "NeuralWorks Professional II/PLUSv5.0," 2 pages.

J.J. Rayan and R.J.W. Rayner, "Unsupervised Time Series Classification," Signal Processing, vol. 46(1), pp. 57–74.

* cited by examiner

Primary Examiner—George B. Davis
(74) Attorney, Agent, or Firm—Pate, Pierce & Baird

(57) ABSTRACT

A method for assessing a condition of an organism having body waves corresponding to states of the organism. The method includes the step of recording signals corresponding to a body wave, output by a portion of the organism in a first state, to provide a first record. In a similar manner, signals are recorded during a time period in which the organism is in a second state, to provide a second record. The first and second records, are processed by applying feature expansion procedures thereto. The results of the feature expansion procedures are evaluated to identify first selected feature expansion procedures effective to distinguish values of the first signals corresponding to the first state from values of the first signals corresponding to the second state.

20 Claims, 43 Drawing Sheets

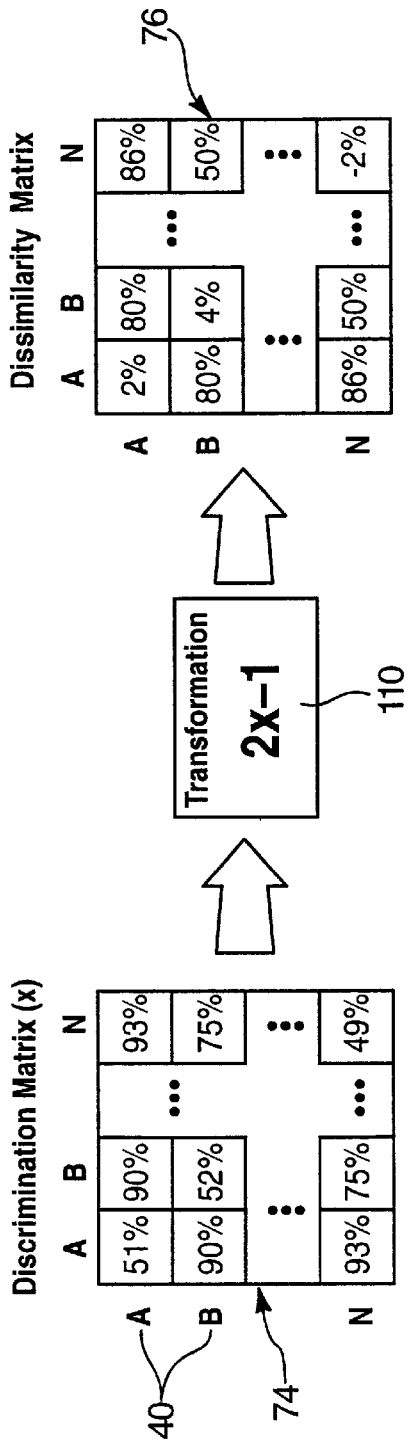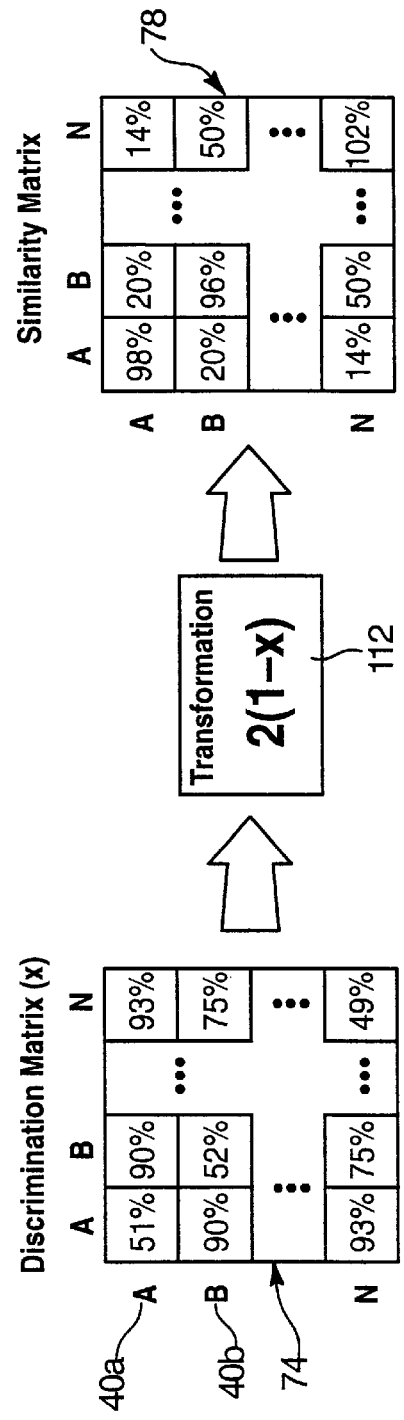

DRUG PROFILING APPARATUS AND METHOD

RELATED APPLICATION

This application claims the benefit of U.S. Provisional Application No. 60/214,624, filed Jun. 28, 2000, and entitled CENTRAL NERVOUS SYSTEM AND CARDIO-VASCULAR DRUG PROFILING SYSTEMS and is a continuation-in-part of co-pending U.S. patent application Ser. No. 08/840,052, filed Apr. 24, 1997, U.S. Pat. No. 6,546,378 B1 and entitled SIGNAL INTERPRETATION ENGINE. The foregoing applications are hereby incorporated herein by reference.

BACKGROUND

1. The Field of the Invention

This invention relates to signal processing and, more particularly, to novel systems and methods for pattern recognition and data interpretation relative to monitoring and categorizing patterns for predictably quantifying and evaluating systems of an observed entity as they react to stimuli such as, for example, drug profiling.

2. The Background Art

The nervous system is a complex network of tissue for carrying and transmitting signals from one part of a body to another. The nervous system can be divided into the central nervous system and the peripheral nervous system. The central nervous system comprises the brain and spinal cord, to which sensory impulses are transmitted and from which motor impulses pass out, and which coordinates the activity of the entire nervous system. The peripheral nervous system incorporates the remainder of the nerve elements of the body. The autonomic nervous system governs involuntary actions and consists of the sympathetic and the parasympathetic nervous systems.

The impulses (currents) of the nervous system may be measured and charted for the purposes of study and evaluation. For example, electroencephalograms (EEG) can be used to detect and record the impulses of the brain (brain waves). Electrocardiograms (EKG) can be used to gather and chart the impulses and currents of the heart (e.g., changes of electrical potential occurring during the heartbeat). Magnetoencephalographs (MEG) can also be used to measure and chart the changing magnetic fields of the brain. An analysis of the impulses of a particular system or organ (e.g., brain, heart or the like) may provide information as to how the particular observed entity (i.e., human or animal) is performing or reacting to stimuli.

A variety of techniques or strategies of analysis have been developed by those skilled in the art to amplify, analyze and interpret EEG, EKG and MEG waveforms. As appreciated, each of these analysis techniques, however, has its own advantages and disadvantages. Specifically, strategies of analysis used by those skilled in the art may range from the early techniques of spectral analysis and multiple-trial waveform averaging, to various transforms, time-frequency distributions, spatial filtering methods, to one or more of the newer approaches of neural networks, fuzzy logic systems and integrated neurofuzzy systems.

One of the disadvantages of prior art spectral analysis techniques is that they are generally limited to the analysis of a single channel or the comparison of two channels at a time. In addition, spectral analysis usually relies on human inspection of the generated waveforms, whereas in frequency representations, time domain information is implicit or hidden.

Multiple-trial waveform averaging is a widely used analysis technique method that uses summing and averaging over many trials to amplify evoked and event-related signals while reducing background noise. While useful for certain applications, averaging techniques have several significant drawbacks. For example, large quantities of information may be lost in the averaging process as only those signals that are robustly time-locked to a stimulus or response are able to survive the summation over multiple-trials. Another serious disadvantage is that the averaging process only provides a comparison between groups of trials rather than between individual trials themselves. Additionally, the need to first record multiple trials before a reliable evoked potential (EP) can be obtained tends to reduce the utility of signal averaging for real-time applications.

Alternative analysis approaches have been developed by those skilled in the art in an attempt to overcome many of the limitations of multiple-trial waveform averaging. These prior art techniques or methods of analysis may include, for example: (1) Fourier Transforms, (2) Hilbert Transforms, (3) Wavelet Transforms, (4) Short-Time Fourier Transforms, (5) Wigner Functions, (6) Generalized Time-Frequency Distributions and other joint time-frequency distributions. While valuable for certain indications, these alternative prior art approaches are usually accomplished using only a single channel. Therefore, there is no spatial information and, accordingly, inter-channel relationships are often missed. Moreover, these prior art alternate approaches have not been integrated with computerized condition discrimination. Like spectral analysis techniques, these alternate prior art approaches rely on human visual inspection of the generated waveforms in concluding findings, which produces a review process fraught with the potential of observer error.

Spatial filtering methods have also been investigated which include: (1) Principal Component Analysis, (2) Singular Value Decomposition and (3) Eigenvalue Analysis. These prior art filtering methods tend to ignore frequency, and often temporal information as well. Additionally, these prior art spatial analysis techniques must be applied to averaged evoked potentials or the noise level is prohibitive. The foregoing prior art spatial filtering methods therefore are not typically useful for single-trial analysis.

Additional analysis techniques and methodology have been developed by those skilled in the art which take advantage of recent increases in computer processing power. Neural networks have been developed to discover discriminant information. The traditional neural network approaches, however, generally take a long time to program and learn, are difficult to train and tend to focus on local minima to the detriment of other more important areas. Moreover, most of these analysis techniques are limited by a lack of integration with time, frequency and spatial analysis techniques.

Although the forgoing analysis techniques and methods of wave signal processing have provided useful concepts and are valuable in their application in particular areas, due to their inherent narrow ranges of applicability, these prior methods of analysis have provided a fragmentary approach to brain signal evaluation. To this end, the prior art methodologies for evaluating waveforms have significant weaknesses and limitations, and none seem to meet the goals of rapid accurate analysis of all pertinent characteristics of a wide variety of single-trial waveforms. What is needed, therefore, is an integrated waveform analysis method capable of extracting useful information from highly complex and irregular waveforms such as EEG, EKG and MEG data.

BRIEF SUMMARY AND OBJECTS OF THE INVENTION

In view of the foregoing, it is a primary object of the present invention to provide novel systems and methods for signal processing, pattern recognition and data interpretation by means of observing the affects of a particular state or event on an observed entity.

It is also an object of the present invention to provide a method for improved drug modeling for evaluating the benefits of drugs and side-effect predication in relation to an observed entity (e.g., human or animal).

It is a further object of the present invention to provide an improved method for drug fingerprinting.

Additionally, it is an object of the present invention to provide novel systems and methods for measuring the effect of a particular event or state on the cognitive skills, motor ability, sensation, perception and the like of an observed entity (e.g., human or animal).

It is still a further object of the present invention to provide novel systems and methods for one or more of the following: (1) determining whether a drug successfully crosses the blood-brain barrier; (2) determining whether a drug alters brain function; (3) determining whether a drug modifies cardiovascular activity; (4) determining of dose response relationships by analyzing the effect of a range of doses on EKG or EEG; (5) measuring drug-induced brain activity patterns indicating the presence of particular side effects inducing drowsiness, nausea, headaches, dizziness or cognitive impairment; (6) identifying the effect of a neurological drug on the electrical activity of the brain and heart in animal models and in human clinical trials; (7) improving the accuracy of drug evaluation with improved discrimination of physiological similarities and differences between distinct drug types; (8) lowering the cost of toxicology testing by more accurately revealing the effects of drugs on neurological and cardiovascular information processing systems in preclinical and in clinical trials; and (9) speeding the development of new drugs by shedding new light on drug-induced brain and heart activity patters.

Consistent with the foregoing objects, and in accordance with the invention as embodied and broadly described herein, apparatus and methods in accordance with the present invention may be used to develop a new drug evaluation protocol which includes the step of obtaining EEG signal data relating to several drug states and using an event resolution imager (ERI) to conduct analysis to determine the best way to distinguish which drug is present or associated with a given time segment or epoch of EEG data. This discrimination capability stems from recognition of learned patterns in the multichannel EEG time series data. Experiments may be performed to find the best discriminant wave-processing sequence. The best wave-processing sequence may then be automated and tested on additional drug-labeled EEG data to determine utility, accuracy and the ability to generalize. Finally, the protocol may be packaged for one-button operation and ease of use, thus making the drug evaluation method of the present invention more economical and efficient.

Particularly, characteristic signals relating to a particular observed entity may be gathered, amplified, processed and recorded. The signals may be divided into time segments or epochs of a selected time period. Each epoch may contain all the signals recorded from the observed entity during that selected time period. Each epoch may be related to a particular event or state of the observed entity that was occurring at the time the signal (signals) contained in the epoch were recorded.

The basic strategy of an event resolution imager (ERI) in accordance with the present invention is to apply several methods of analysis to each epoch to find consistent differences between epochs relating to different events or states and similarities within the epochs related to similar events or states. ERI analysis may consists of three primary processes. Generally, these process include learning, classification and validation.

The learning process may use several waveform analysis techniques including, by way of example and not limitation, time-frequency expansion, feature coherence analysis, principal component analysis and separation analysis. Each epoch may be decomposed into features in an extended phase space representing spatial, time, frequency, phase and interchannel relationships. These features may then be analyzed in detail for characteristics common to each epoch. This analysis may include evaluation of coherence between signals distributed across the four domains of space, time, frequency and phase.

The learning process performs a set of analyses to find features that are most reliably different between epoch types, which is characterized as state separation analysis. This consists of waveform analysis, distribution function analysis and discriminant optimization. Finally, the results of the above analyses are used to generate a set of parameters, components, functions and criteria which best identify epoch type and discriminate between epochs. This information may then be recorded as an interpretation map.

In one presently preferred embodiment of the present invention, a classification process uses the interpretation map to apply the set of analyses and criteria previously determined to be optimal, to the classification of epochs having "unknown" events or states corresponding thereto. The classification system analyzes each epoch as an individual event (no averaging) and generates a composite, clean waveform made up of those characteristics or features generated by the analysis.

The classification process may then pass the classification data to an output generator to compile a statistical summary of the results, including the confidence level that each epoch was classified correctly. As appreciated, additional outputs may include calculations of sensitivity, specificity and overall accuracy.

True epoch event or state labels may be bound to analyzed epochs to enable a comparison with epoch classifications generated by the classification system. That is, the actual or true event associated with a particular epoch may provide a key to determine if that epoch has been correctly classified. Accordingly, this may provide a method of testing or validating the accuracy of the ERI. High classification accuracy of epochs that are separate and distinct from the epochs used in the creation of the interpretation map, indicates a valid derived interpretation map.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 11 is schematic block diagram of one presently preferred embodiment illustrating the transformation of a discrimination matrix into a dissimilarity matrix in accordance with the present invention;

FIG. 12 is schematic block diagram of one presently preferred embodiment illustrating the transformation of a discrimination matrix into a similarity matrix in accordance with the present invention;

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and methods of the present invention, as represented in FIGS. 1 through 43, is not intended to limit the scope of the invention, as claimed, but is merely representative of the presently preferred embodiments of the invention.

Certain embodiments in accordance with the present invention incorporate the application of the hardware and software of the signal interpretation engine disclosed in U.S. patent application Ser. No. 09/840,052, filed Apr. 24, 1997, and entitled SIGNAL INTERPRETATION ENGINE, which is incorporated herein by reference. The present application does not attempt to describe every detail of the signal interpretation engine (e.g., event resolution imager). To this end, the details of the signal interpretation engine are contained in the patent application directed thereto. Whereas, only a general description of the key modules and procedures is presented herewith.

Figure 1:
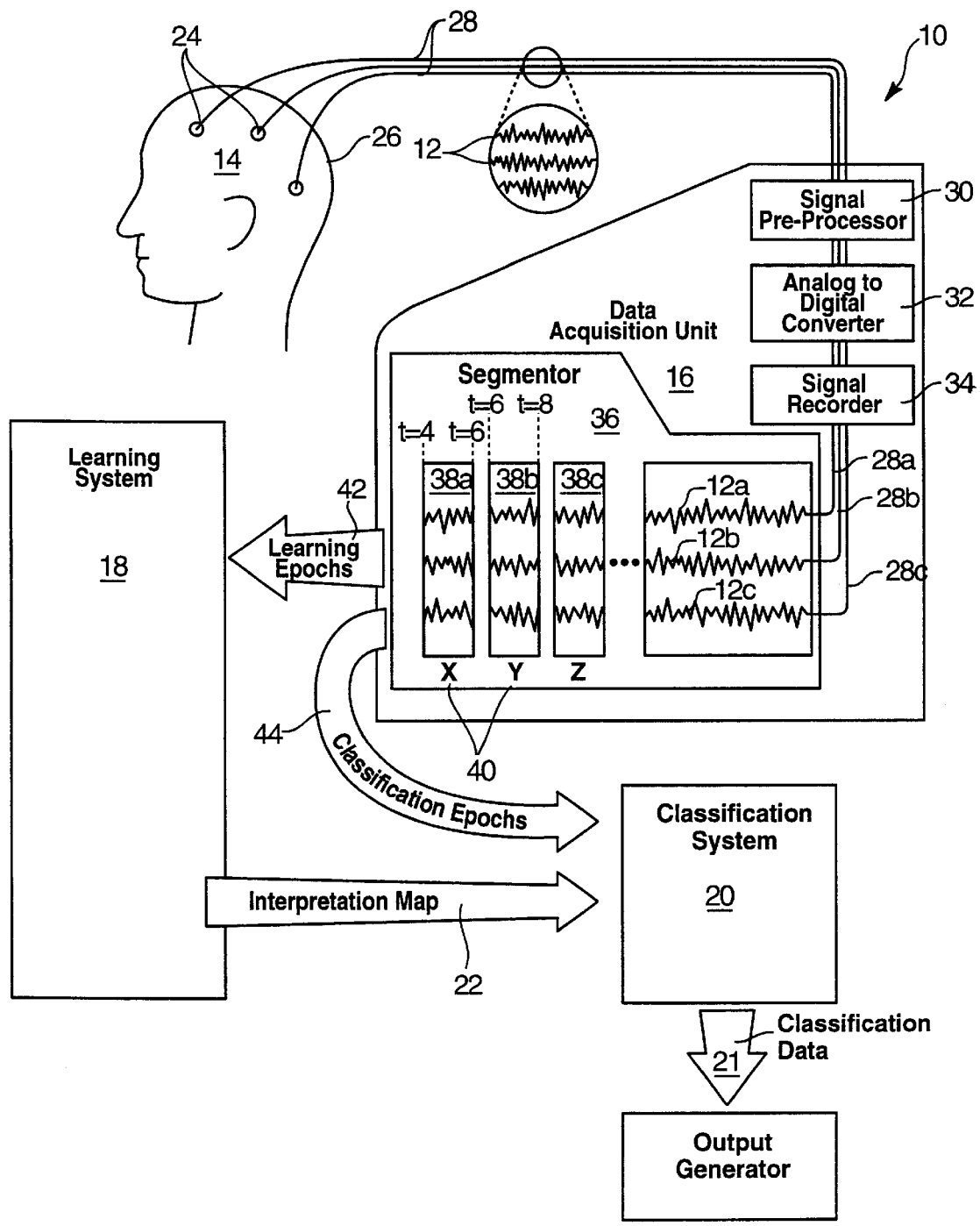
FIG. 1 is a schematic block diagram of one presently preferred embodiment of an event resolution imager (ERI) in accordance with the present invention.

Referring to FIG. 1, one presently preferred embodiment of an event resolution imager (ERI) 10 in accordance with the present invention is illustrated. An ERI 10 may gather signals 12 from an observed entity 14 (e.g. human, animal, plant, microbe, or the like), process the signals 12, and produce an output sufficient to provide the user with an increased understanding of what is happening to the observed entity 14. Preferably, the main sub-systems of the ERI 10 may include a data acquisition unit 16, a learning system 18 and a classification system 20.

In one presently preferred embodiment, the signals 12 received from the observed entity 14 may be gathered, amplified, processed and recorded by the data acquisition unit 16. The data acquisition unit 16 may then send the processed signals 12 to either the learning system 18 or the classification system 20. The decision of where the signals 12 are sent generally depends on the particular location in the processing cycle. That is, the signals 12 may be sent to the learning system 18 to be expanded for the creation of an interpretation map 22. However, once the interpretation map 22 has been created and transmitted to the clarification system 20, the signals 12 may be sent directly from the data acquisition unit 16 to the classification system 20.

The observed entity 14 of a presently preferred embodiment of the present invention may be any entity 14 that produces signals 12 (i.e., body waves 12), (e.g. currents, impulses, magnetic fields, transmissions, or the like) which contain information relating to the performance, state or condition thereof. For example, a brain produces signals 12 to communicate with and control the body of which it is a part. The signals 12 of the brain contain information as to how the brain is functioning and what is being processed. Another example may be the heart. The muscle tissue of the heart emits electrical signals 12 used to control beating frequency and the like.

In selected embodiments, the signals 12 may be measure quantities rather than emissions. For example, a signal 12 may be a red blood cell count. Other signals 12 in accordance with the present invention may be hormone levels, antibody counts, respiration pressure, blood pressure, skin conductance, chemical potentials, infrared light propagating or scattering through tissue, and the like.

Those skilled in the art will readily recognize various other applications are likewise suitable. It is intended, therefore, that the examples provided herein be viewed as exemplary of the principles of the present invention, and not as restrictive to a particular structure or method for implementing those principles.

An observed entity 14 in accordance with the present invention may be any organism, organ, tissue sample, or cell. For example, an observed entity 14 may be a heart, liver, lung, kidney, intestine, muscle, vein, artery. Additionally, an observed entity 14 may be a system such as the central nervous system, peripheral nervous system, somatic nervous system autonomic, nervous system, parasympathetic nervous system, sympathetic nervous system, cardiovascular system, lymphatic system, immune system, endocrine system, respiratory system, or the like.

As will be appreciated, the observed entity 14 need not be an entire organ or system. The observed entity 14 may be a sub-section thereof. For example, the observed entity 14 may be the portion of the brain responsible for receiving and processing information from the optical nerves. In other embodiments, the observed entity 14 may be a particular muscle responsible for extending or contracting a particular finger. Additionally, the observed entity 14 may be a particular nerve circuit. For example, the observed entity 14 may be sub-component of the somatosensory evoked potential (see FIG. 43, four such sub-components are shown.) In this regard, those skilled in the art will recognize various other applications which are likewise suitable. It is intended, therefore, that the examples provided herein be viewed as exemplary of the principles of the present invention, and not as restrictive to a particular structure for implementing those principles.

Any suitable method may be employed to gather the signals 12 emitted from the observed entity 14. Such methods may be invasive or non-invasive. In one presently preferred embodiment, the brain signals 12 may be gathered by multiple nodes 24 secured to the head of a patient. In another embodiment, a signal 12 generated by the heart may be gathered by inserting a single probe into the muscle tissue thereof. The wiring 28 or transmission lines 28 used to transfer the signal(s) 12 to the data acquisition unit 16 may be of any suitable variety providing sufficient conductance for the particular signal 12 being monitored.

The number of nodes 24 (i.e., probes, electrodes, and the like) may be selected to provide the desired number of signals 12. The number of signals 12 desired may vary, depending of the particular observed entity 14. For example, when monitoring the human brain, it may be desirable to have on the order of three hundred nodes 24 to receive three hundred separate signals 12. In other embodiments, a single node 24 receiving a single signal 12 may suffice depending upon the nature of the evaluation. General factors that may influence the selection of the number of nodes 24 and accompanying signals 12 may include accessibility to the observed entity 14, cost of parts and installation, time of installation, data acquisition processing capabilities, interference between nodes, effect on observed entity 14, and the like.

For general background information, electroencephalograms (EEG), magnetoencephalographs (MEG), and electrocardiograms (EKG) are common monitoring equipment (found in many hospitals). An EEG typically receives minute electrical signals from electrodes placed on the scalp of the patient. The electrodes are preferably held in place by an electrically conducting gel. The EEG greatly amplifies the signal received until a usable magnitude is achieved. Often a galvanometer is used to plot the amplified signal on a strip of paper. The resulting plot is a highly oscillatory waveform that is typically analyzed by the operator of the EEG or attending physician.

If desired, the output of an EEG may be directed to an analog to digital converter rather than to a galvanometer. An analog to digital converter may periodically sample the electrical current amplified by the EEG and assign a numerical value corresponding to the magnitude thereof. The sampling frequency is typically selected to provide an accurate map of the waveform. A sampling rate of about 100 samples per second may suffice. A greater sampling rate, however, may produce more accurate results. Once the numeric values representing the waveform have been recorded, they may be processed or used again to generate a graph of the waveform.

MEG's and EKG's work in a similar manner in comparison to EEG's. The difference however is that a MEG measures minute magnetic fields produced in the brain rather than electrical currents and an EKG measures the electrical currents of the heart rather than brain waves.

The signals 12 received from observed entity 14 are preferably sent to the data acquisition unit 16, the data acquisition unit 16 in accordance with the present invention, may be any unit (i.e., hardware/software combination) capable of gathering, amplifying, recording and processing the signals 12 into usable data. In selected embodiments of the present invention, the data acquisition unit 16 may include a signal pre-processor 30. The signal pre-processor 30 may gather, amplify, filter, clean or otherwise prepare the signals 12 for additional processing. In certain embodiments, the gathering and pre-processing of the signals 12 may be carried out by an EEG, an EKG, a MEG, or the like.

In one presently preferred embodiment as shown in FIG. 1, the data acquisition unit 16 is configured to interface with an EEG (MEG, EKG or the like). In such a configuration, the data acquisition unit 16 may receive the signals 12 from the EEG 30 in analog or digital form. If received in analog form, the data acquisition unit 16 may include an analog to digital converter 32 to convert the signals 12 to digital.

In selected embodiments, an EEG 30 (MEG 30, EKG 30, or the like) may be incorporated into a single unit incorporating both hardware and software in accordance with the present invention. In such a configuration, the transmission lines 28 may carry the signals 12 to the unitary structure where they may be processed in accordance with the present invention and the results displayed.

In an alternative embodiment, the data acquisition unit 16 may simply be a personal computer having an appropriate hardware and software configuration sufficient to provide a desired level of signal reception, amplification, recordation and manipulation capabilities. In such embodiments, general data acquisition software and hardware that is commercially available may be sufficient.

After the signal pre-processor 30 has performed its function, the signal data 12 may be recorded by a signal recorder 34. The recorded signal 12 may then be passed to a segmentor 36 to be divided into time segments 38 or epochs 38. Each epoch 38 contains a piece of signal data 12 gathered from each node 24 corresponding to a particular time segment 40, state 40, or event 40.

An event 40 (time segment 40, state 40) in accordance with the present invention may be any stimuli applied to the observed entity 14. In other embodiments, an event 40 may not be a stimuli, but rather a condition 40 or state 40 (e.g., high blood pressure). Stimuli may be externally or internally applied. For example, event 40 may be the delivery of a drug, ingestion of a food or liquid, exposure to sun light, or the like. An internal stimuli event 40 may be a thought process or the like. In selected embodiments, certain signals 12 may also be used as an event 40. For example, a white blood cell count may be used as a signal 12 for analyzing the immune system or it may be used as a state 40 for studying the effect a high white blood cell count may have on the brain.

In one presently preferred embodiment of the present invention as shown in FIG. 1, if there are three signal input lines 28a, 28b and 28c recording signal data 12a, 12b, and 12c, the recording from line 28a from time t=4 to t=6 seconds, the recording from line 28b from time t=4 to t=6 seconds, and the recording from line 28c from time t=4 to t=6 seconds would equate to a first epoch 38a. The time from t=4 to t=6 seconds may correspond to some event X. A second epoch 38b may contain the recording from line 28a from time t=6 to t=8 seconds, the recording from line 28b from time t=6 to t=8 seconds, and the recording from line 28c from time t=6 to t=8 seconds. The time from t=6 to t=8 seconds may correspond to some event Y.

Events X and Y may be similar or dissimilar. For example, in one instance, events X and Y may both be EEG recordings from a patient under the influence of ethanol (X and Y are both state or event A). In this situation events X and Y may be considered to be similar even though they are not recordings occurring at the same time. In another instance, event X may be an EEG recording of a normal patient (state or event A) while event X is a recording of that same patient under the influence of ethanol (state or event B). In this situation events X and Y are said to be dissimilar.

With the completion of the segmentation process by means of the segmentator 36 of the data equation unit 16, a selected number of epochs 38 may proceed to the learning system 18 to begin feature expansion. Epochs 38 that are transmitted to the learning system 18 may be referred to as learning epochs 42. The basic strategy of feature expansion process is to apply several methods of analysis to each epoch 38 to find consistent similarities within epochs 38 related to similar events 40 and differences between epochs 38 relating to different events 40.

The results of the analyses may be used to generate a set of parameters, scaling factors, patterns, components, functions, and criteria, which best identify epochs 38 relating to similar events 40 and discriminate between epochs 38 relating to dissimilar events 40. This information may be recorded as part of an interpretation map 22.

Upon the formulation of the interpretation map 22 by the learning system 18, the interpretation map 22 may be transmitted to the classification system 20. Preferably, the classification system 20 provides a test to verify the utility of the newly generated interpretation map 22.

The classification system 20 may also import epochs 38 directly from the data acquisition unit 16. The epochs 38 received from the data acquisition unit 16 are generally referred to as classification epochs 44. The classification system 20 may analyze and expand the classification epochs 44 in accordance with the information supplied by the interpretation map 22. Upon completion of the classification process, the classification data 21 may be passed to an output generator 46 to be converted into useful and easily accessible information.

Figure 2:
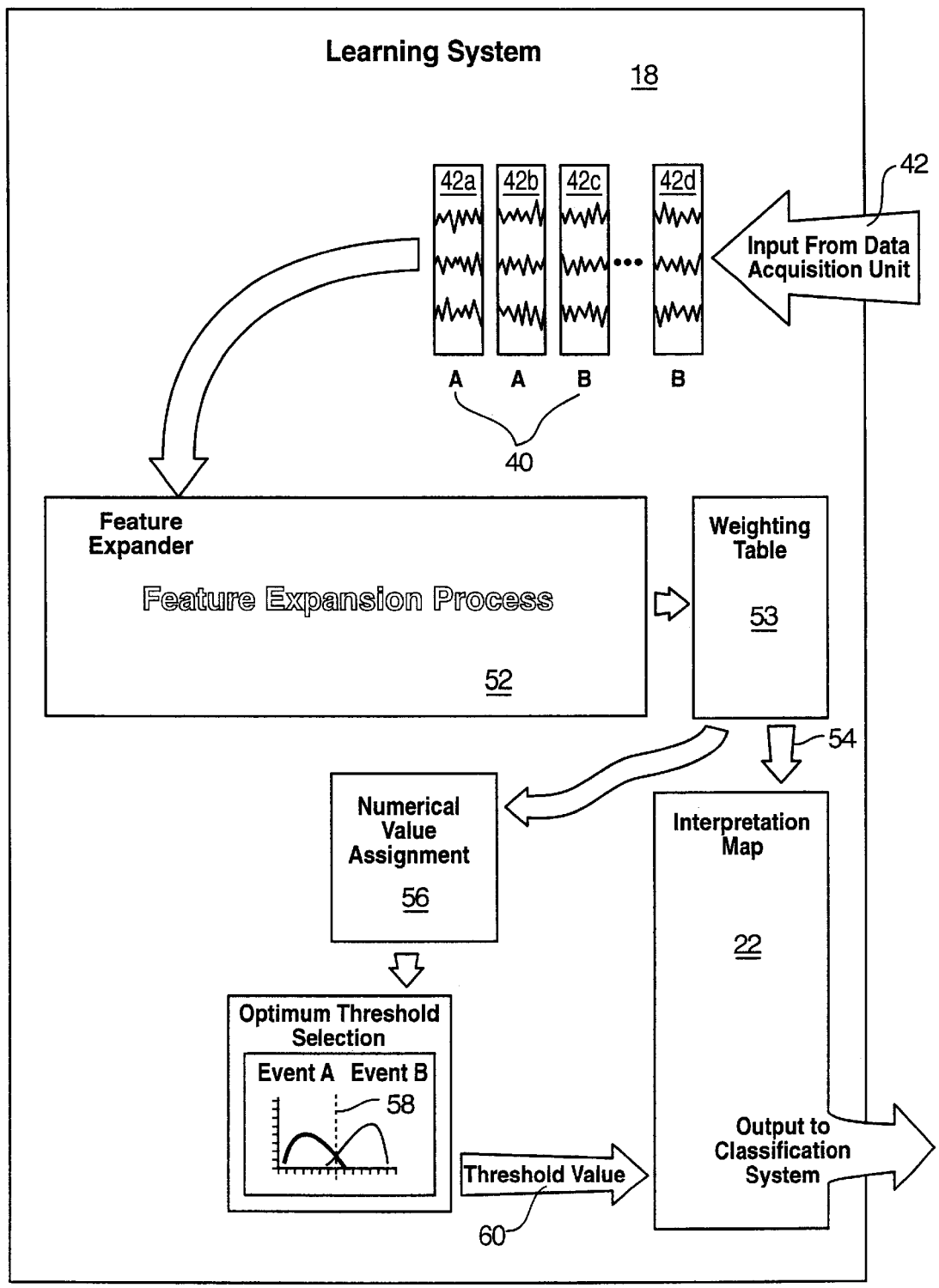
FIG. 2 is a schematic block diagram of one presently preferred embodiment of a learning system in accordance with the present invention.

Referring now to FIGS. 1 and 2, as discussed hereinabove, the learning system 18 may input and analyze learning epochs 42 received from the data acquisition unit 16 to create an interpretation map 22. The learning system 18 manipulates each learning epoch 42 to discover or expand the features hidden therein. By processing each epoch 42 through a multitude of mathematical manipulations, features or unique characteristics may be magnified to the point that they become easily discernable.

In one presently preferred embodiment of the present invention, the learning system 18 may operate on a binary basis. That is, the learning system 18 may compare events 40 related to two states or conditions. For example, the learning system 18 may perform analysis to determine feature differences between epochs 42 related to state A and epochs 42 related to state B. States A and B may be pre-injection of a particular drug and, respectively, post-injection of the drug. In other applications of the present invention, states A and B may be the presence of ethanol in the observed entity and the presence of heroine in the same observed entity, respectively. In still other applications, states A and B may both be the presence of pentobarbital in the patient. In a situation where the two states A and B are actually the same state, theoretically the learning system 18 should not be able to find any significant differences in the expanded features.

The feature expander 52 analyzes an epoch 42 and identifies a set of characteristics which best differentiates and identifies epochs 42 related to a particular type of event (e.g. state A or state B). In one presently preferred embodiment of the present invention, the feature expansion process may involve multiple waveform analysis techniques including time-frequency expansion, feature coherence analysis, principal component analysis and separation analysis.

Each signal 12 contained in an epoch 42 may be processed individually. If desired, however, feature expansion may include signal consolidation. If there are multiple input signals 12 in an epoch 42, a signal consolidator may superimpose any combination of the input signals 12 to create a composite signal. Particularly, however, this may not be an averaging process. In certain embodiments, selected signals 12 of an epoch 42 may be processed individually while others are combined and analyzed as a superposition.

Each learning epoch 42 may be decomposed into features in an extended phase space representing spatial, time, frequency, phase and interchannel relationships. These features are then analyzed in detail for characteristics common to the epochs 42 relating to a particular event (i.e., A or B). This analysis includes evaluation of coherence between signals 12 distributed across the four domains of space, time, frequency and phase.

The feature expander 52 may perform a set of analyses to find features that are most reliably different between epochs 42 related to different events 40. These polarizing features may be generated or discovered by applying frequency weighting factors, phase weighing factors, amplitude weighting factors, selective superposition of signals 12, comparing spacial pattern, comparing signal shape, comparing area under the curve of selected signals 12, analyzing temporal latencies in response to stimuli, or the like. This form of analysis may be referred to as state separation analysis and may consist of waveform analysis, distribution function analysis, and discriminant optimization.

Feature selection may provide a level of resolution control in an ERI 10 in accordance with the present invention. That is, by selecting which signals 12, and which features of those signals 12, are expanded and analyzed, a user may increase or decrease the discrimination resolution produced. Decreased resolution may present certain advantages to the user.

The results of the analyses may be used to generate a set of parameters, scaling factors, weights, patterns, components, functions, and criteria, which best identify epochs 38 relating to similar events 40 and discriminate between epochs 38 relating to dissimilar events 40. This information may be recorded as part of an interpretation map 22.

Once the characteristic feature(s) of a particular epoch 42 has been expanded, the expanded features may be passed to a weighting table 53. A weight table 53 and accompanying weights may be based on some manipulation of the signal data 12 of an epoch 42 that will tend to self-neutralize. For example, certain resonance frequencies may occur at a higher or lower frequency than the background noise. Thus, shifting signal data 12 slightly forward or backward within a time segment 42 and adding or multiplying the signal data 12 together may provide enhancement of certain features, while minimizing others relative thereto. Thus, in general, several approaches to a weight table 53 may be implemented.

Epochs 42 may be assigned a numerical value (56) corresponding to the magnitude of the presence or non-presence of a particular feature. Specifically, the learning system 18 may compare the numerical value assigned to all the learning epochs 42 and select a particular threshold value 58 which best defines the dividing line between epochs 42 relating to different events (i.e., A or B).

For example, the assigned numerical values relating to the expanded features of a recorded epoch 42 from a normal patient (state A) may fall in the range from 31 to 39. The assigned numerical values relating to the expanded features of a recorded epoch 42 from the same patient on ethanol (state B) may fall in the range from 21 to 29. An optimum threshold value 58 for this example would be 30 because it accurately divides the epochs 42 relating to the non-drugged (event A) and the drugged state (event B). In actual practice, the divisions between expanded epochs 42 may not be so delineated as in this example. However, even in situations with overlapping event ranges, an optimum threshold value 58 that best delineates between epochs 42 of dissimilar events (A and B) may be determined. The optimum threshold value 58 may then be passed 60 to the interpretation map 22 to be incorporated therewith.

Figure 3:
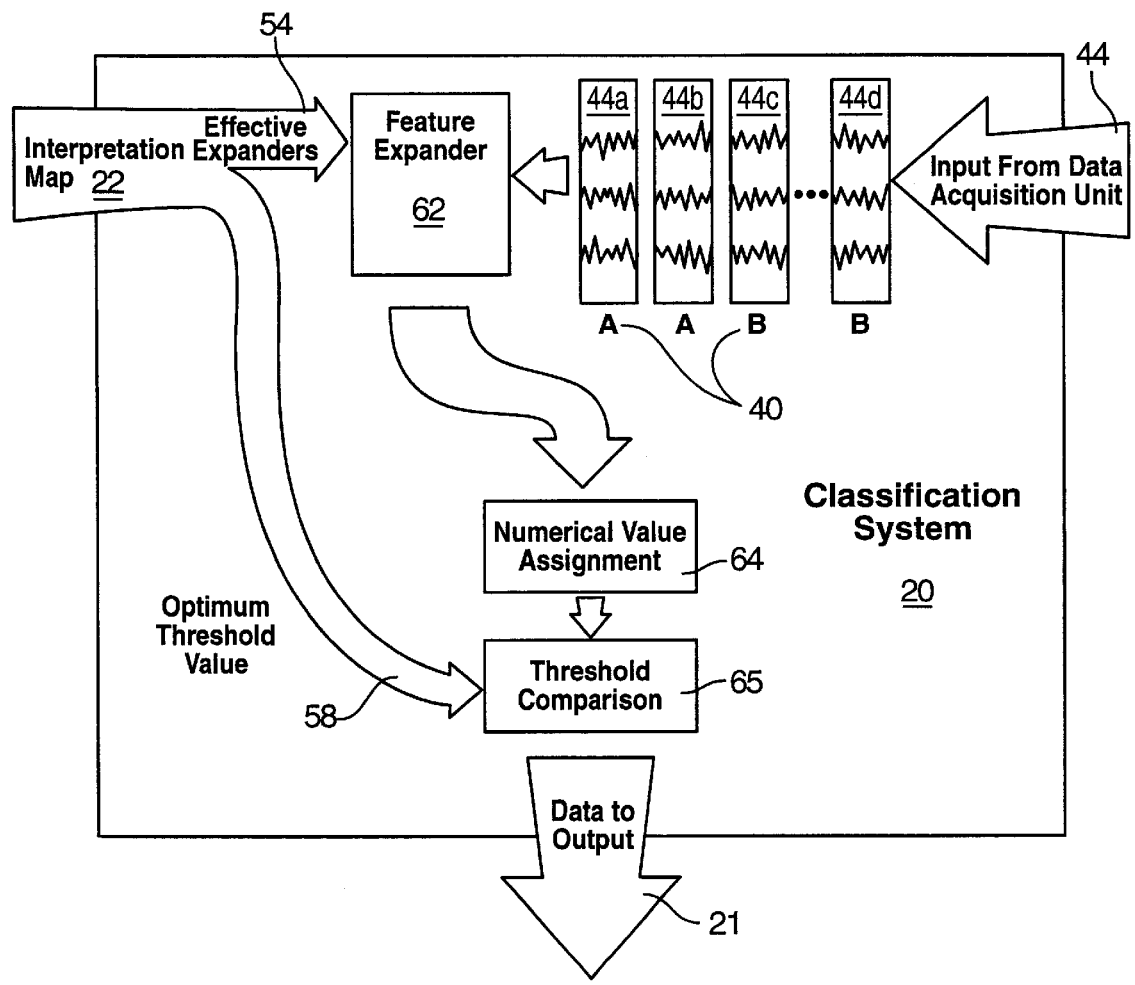
FIG. 3 is schematic block diagram of one presently preferred embodiment of a classification system in accordance with the present invention.

Referring now to FIG. 3, the classification system 20 may import epochs 38 directly from the data acquisition unit 16. The epochs 38 received from the data acquisition unit 16 are referred to herein as classification epochs 44. The classification epochs 44 are typically different than the learning epochs 42 sent to the learning system 18 from which the interpretation map 22 is generated. This allows the interpretation map 22 to be tested on epochs 44 that it has never "evaluated," thus providing a more rigorous evaluation. Additionally, the number of classification epochs 44 is usually much greater than the number of learning epochs 42. Learning epochs 42 typically consist of a fewer number of epochs 42 recorded during a first event (e.g., event A) and a fewer number of epochs 42 recorded during a second event (e.g., event B). Accordingly, classification epochs 44 generally make up the remainder of the recorded epochs 38.

The classification epochs 44 may be delivered to a feature expander 62. The feature expander 62 may include a signal consolidator for superimposing multiple signals 12 to obtain one composite signal for each epoch 44. Unlike the feature expander 52 of the learning system 18, the feature expander 62 of the classification system 20 does not apply a multitude of algorithms to expand the features of the epochs 44. The feature expander 62 simply applies the effective algorithms 54 delivered thereto as part of the interpretation map 22.

Upon completion of the feature expansion, the epochs 44 may be assigned a numerical value 64 corresponding to the magnitude of the presence or non-presence of a particular feature. This assigned numerical value 64 may then be compared against the optimum threshold value 58 provided by the interpretation map 22 to provide a threshold companion 65. Depending on where a particular epoch 44 falls in relation to the optimum threshold value 58, the epoch 44 is classified as being associated with one of the two events (i.e., A or B) being tested. Upon completion of the classification process, the classification data 21 may be passed to an output generator 46 to be converted into useful and easily accessible information as shown in FIG. 1.

Figure 4:
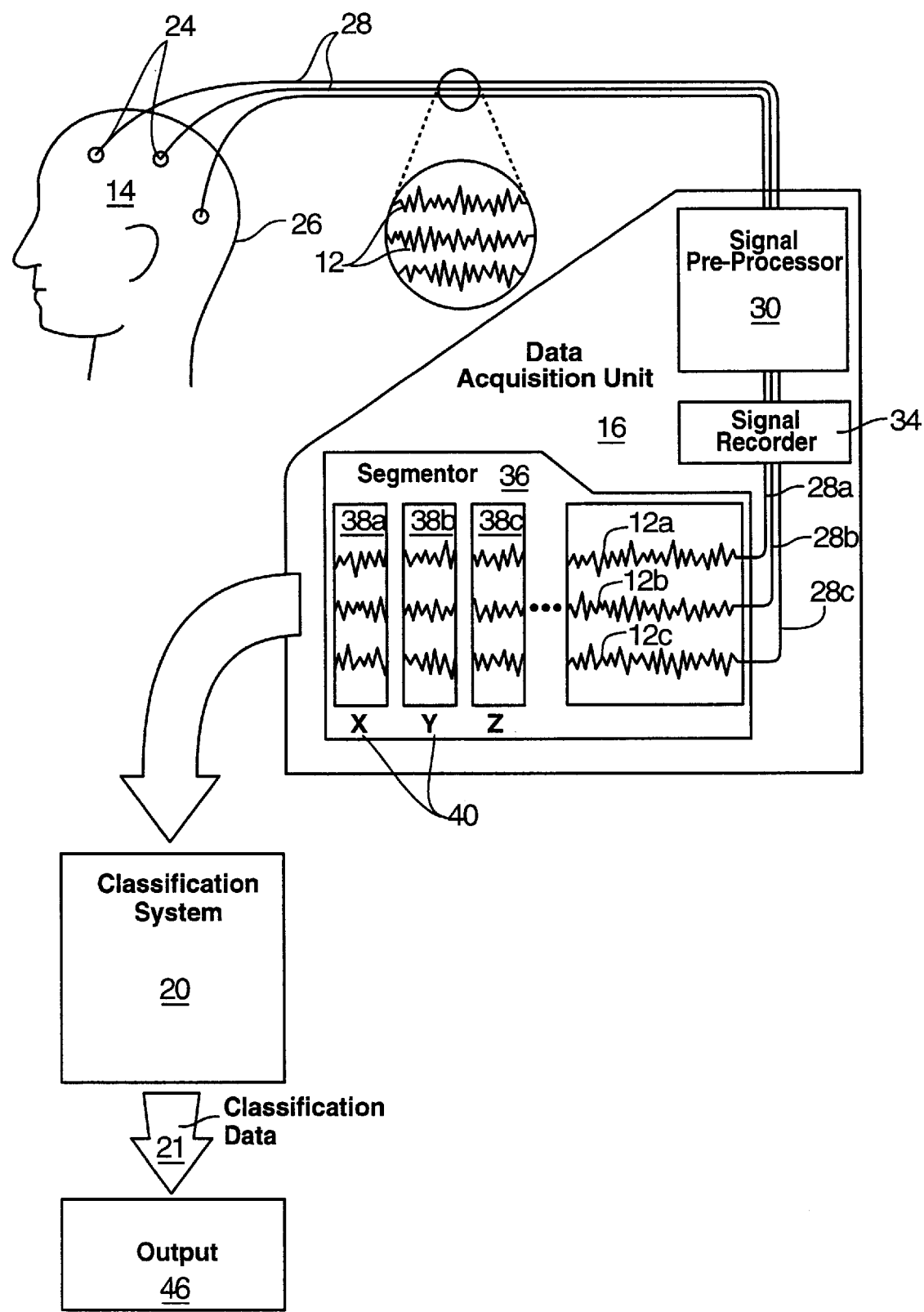
FIG. 4 is schematic block diagram of an alternative embodiment of an ERI in accordance with the present invention.
Figure 5:
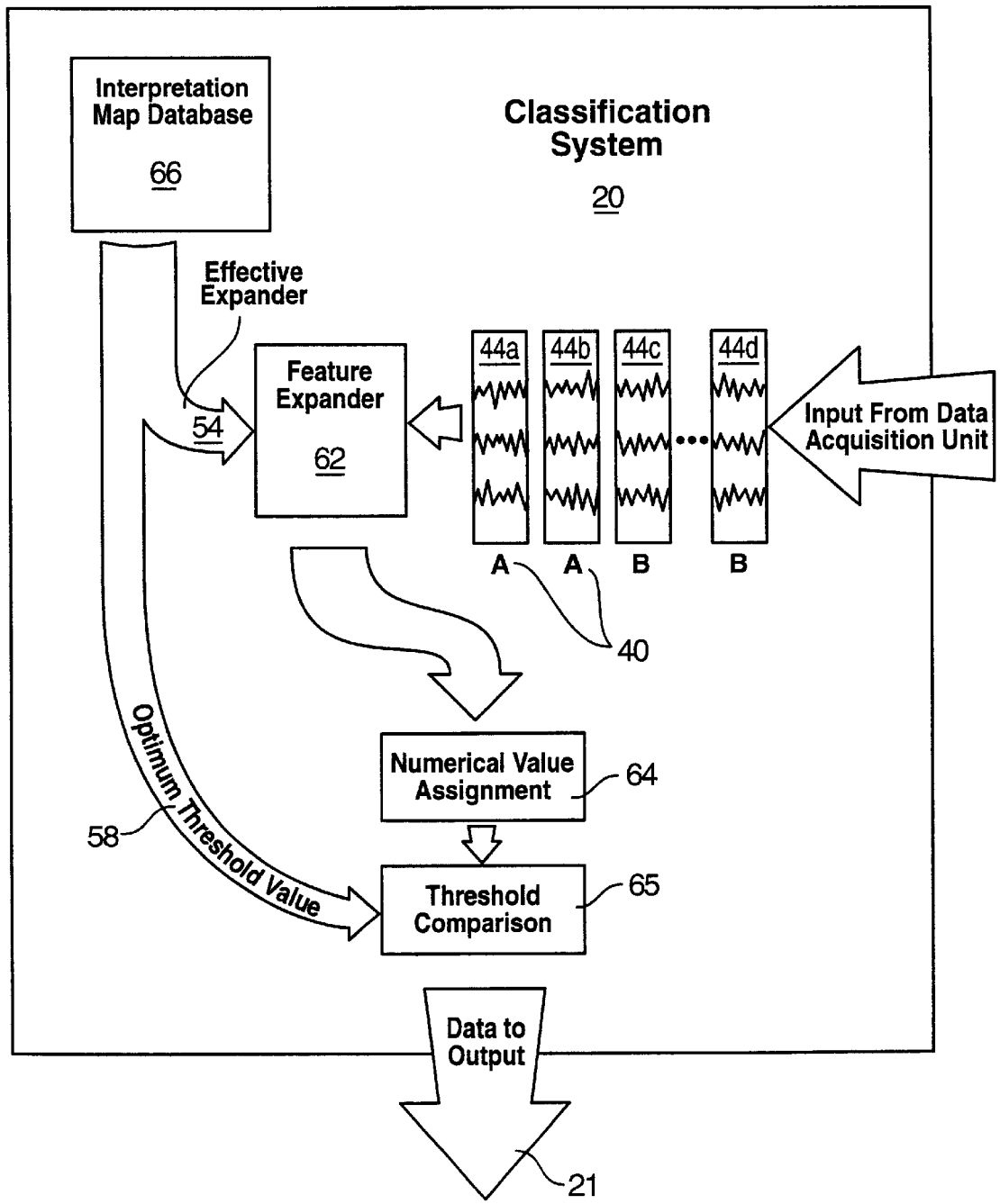
FIG. 5 is schematic block diagram of an alternative embodiment of a classification system in accordance with the present invention.

Referring now to FIGS. 4 and 5, after the ERI 10 has generated an accurate interpretation map 22, it may not be necessary to enter the learning cycle every time new epochs 38 are to be classified. For example, if the ERI 10 is analyzing EEG epochs 38 related to pre and post injection of ethanol in a human, and an interpretation map 22 has already been developed and tested for such a situation, then the newly generated EEG epochs 38 may be passed directly to the classification system 20 for analysis and classification. In such an application, the classification system 20 may have an internal interpretation map 66 containing the needed information.

As discussed hereinabove, certain embodiments in accordance with the present invention may incorporate an ERI 10 into a single unitary unit having a simple user interface. Such embodiments may be supplied with an internal interpretation map database 66 containing interpretation maps for analyzing hundreds or thousands of drugs, drug combinations or other common states or events, as desired. A display and user interface may provide a user with the ability to select which interpretation map is to be used from an interpretation map database 66. In an alternative preferred embodiment of the present invention, an ERI 10 may scan the interpretation map database 66 to find a map most suited to a particular state or event comparison.

An internal interpretation map 66 may also be supplied in addition to a learning system 18. An ERI 10 containing both a internal interpretation map database 66 and a learning system 18 may more quickly analyze common states or events using interpretation maps recorded in the internal interpretation map database 66, while still providing the hardware and software to learn new states and event comparisons.

In selected embodiments, an ERI 10 in accordance with the present invention, may store a copy of every new interpretation map 22 generated in an internal interpretation map database 66 for possible future reference and use. In such a manner, the ERI 10 may quickly build up a database of effective modifiers and the optimum threshold values for state comparisons even when not initially created with such.

Figure 6:
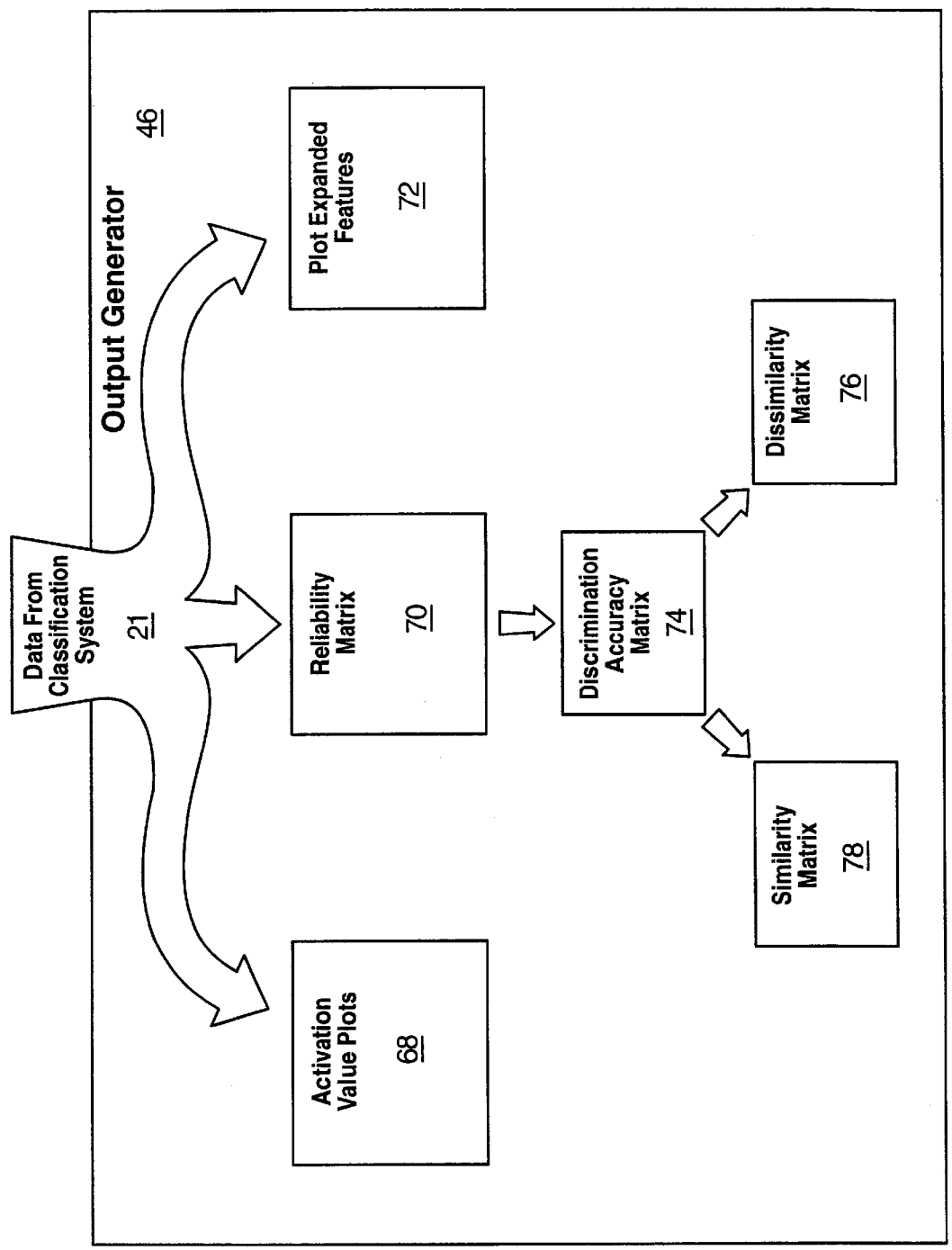
FIG. 6 is schematic block diagram of one presently preferred embodiment of an output generator in accordance with the present invention.

Referring now to FIG. 6, an ERI 10 in accordance with the present invention may present data in multiple useful formats. The following output formats are presented as exemplary models and are not to be interpreted as being restrictive of the available formats. For example, these formats may include activation value plots 68, reliability matrices 70, expanded feature plots 72 and any other suitable format. Moreover, several useful matrices may be derived from a reliability matrix 70. These derivatives may include discrimination accuracy matrix 74 dissimilarity matrix 76 and similarity matrix 78.

An expanded feature plot 72 may simply be a plot of the expanded epoch 44. Once a signal 12 of a particular epoch has been expanded, a characteristic feature may be easily seen. Several of the graphs relating to the Examples presented hereinbelow illustrate different forms of expanded feature plots.

Figure 7:
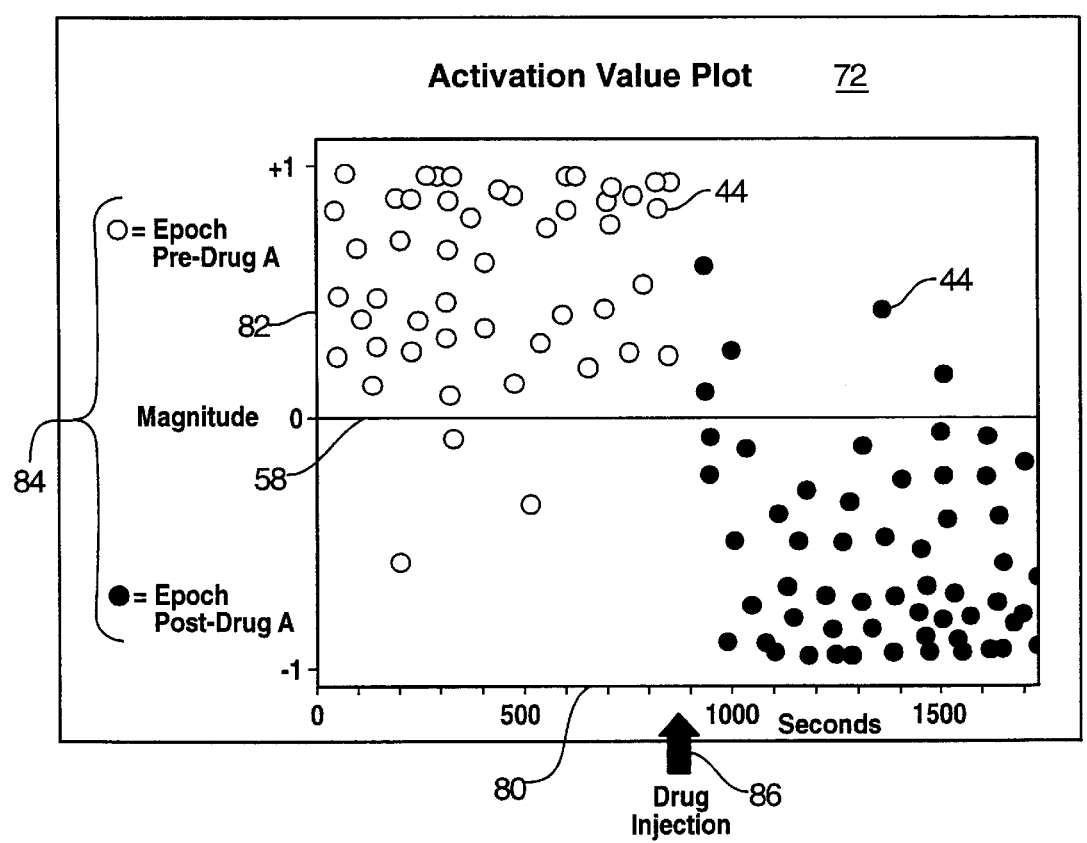
FIG. 7 is one presently preferred embodiment of an activation value plot in accordance with the present invention.

Referring now to FIG. 7, an activation value plot 72 may have a time axis 80 and a magnitude axis 82. The time axis 80 may represent a clock starting at the time the sampling of the input signal 12 begins and continuing until the sampling ends. The magnitude axis 82 may have a range 84 selected to illustrate a magnitude of the presence or non-presence of a particular distinguishing feature contained in each classified epoch 44. This magnitude may correspond to the numerical value assigned 64 during the classification process as shown in FIG. 5.

To create an activation value plot 72, the assigned numerical value of each classified epoch 44 may be scaled or otherwise manipulated to fit in the magnitude range 84 of the plot 72. In one presently preferred embodiment of the present invention, the assigned numerical value is manipulated to fit within the range 84 from −1 to +1. The optimum threshold value 58 may be normalized to zero. Each small circle represents an epoch 44 of highly processed signal activity. The epochs 44 may be spaced along the time axis 80 corresponding to the time when the epoch 44 was recorded.

For the particular example illustrated in FIG. 7, the observed exhibits mostly positive spectrum (from −0.25 to +1) epoch 44 activation values during the time before the injection 86 of drug A. Following the injection 86 of drug A, the epoch 44 activation values are represented by small circles having been darkly shaded. The observed entity (e.g., human or animal) exhibits mostly negative spectrum (from +0.25 to −1) epoch 44 activation values after the injection 86 of drug A. From this activation value plot 72, it can be seen that once drug A is injected, it takes less than 100 seconds to cross the blood-brain barrier and begin to affect the operation of the brain.

The ability to non-invasively and accurately track and monitor the progression of a drug across the blood-brain barrier in real time (on time scales of seconds to minutes) opens the door to a better understanding of this barrier, and sheds light on the effect a given drug has on brain function. The ability to accurately test which drugs are able to cross the blood-brain barrier and to monitor the time course of the crossing, constitutes a powerful new tool for the evaluation and acceleration of the development of neurological drug candidates. To this end, the present invention may be applied to several areas including dose-response studies.

Figure 8:
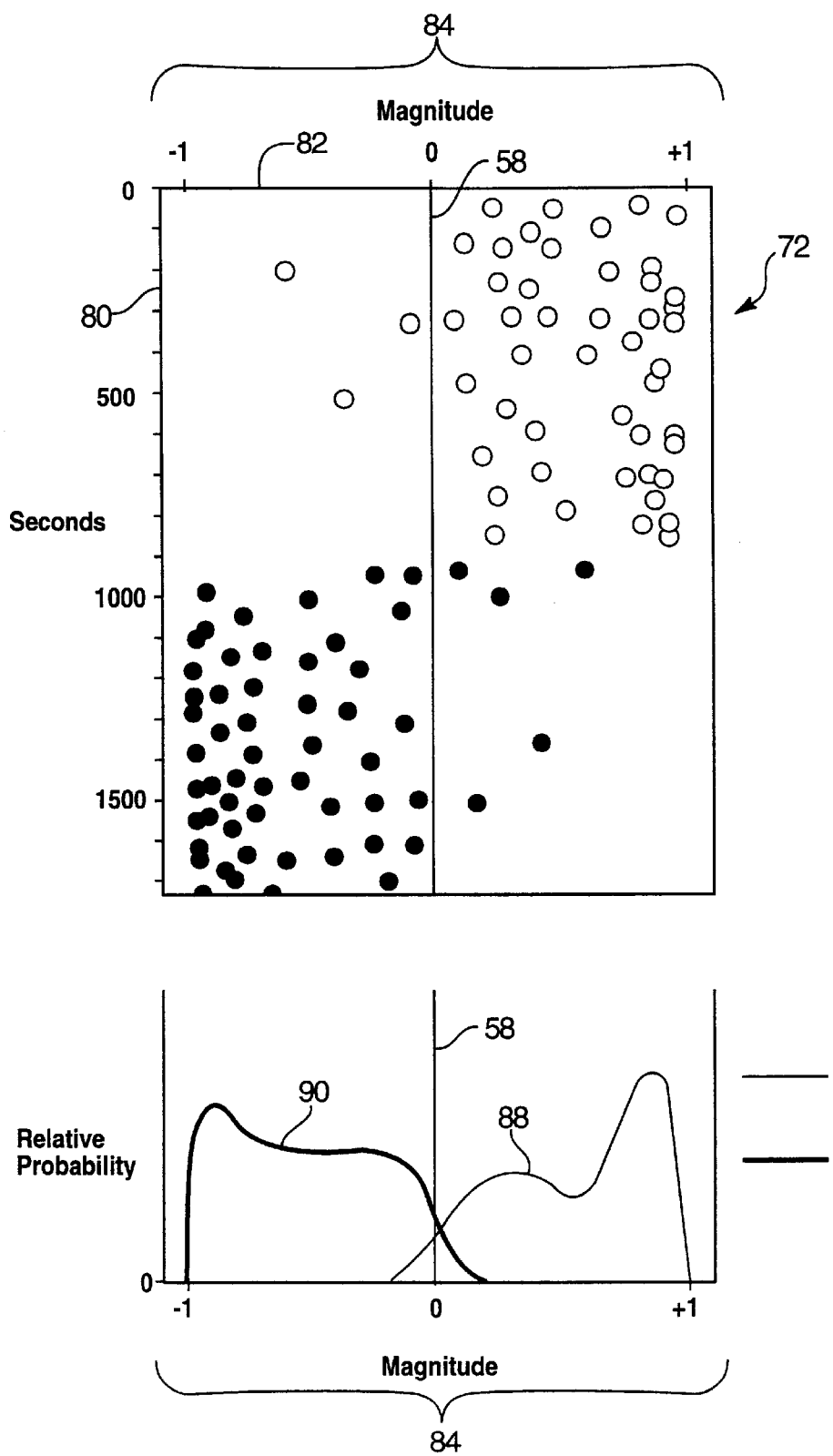
FIG. 8 is one presently preferred embodiment of a activation value plot used to generate a "fingerprinting" probability profile in accordance with the present invention.

Referring now to FIG. 8, the activation value plots 72 may be used to create a "fingerprint" corresponding to a particular event or state. Activation value plots 72 illustrate the relative probability that an epoch 44 corresponding to a particular state will have a particular magnitude 82. From the illustrated activation value plot 72, it can be seen that a normal non-drug A state generates a particular epoch 44 probability profile 88. A post-injection produces a different epoch 44 probability profile 90. Not only are the two profiles 88, 90 differently shaped, they are also shifted from one another.

Epoch 44 probability profiles 88, 90 may be used to identify a particular state or event that the observed entity (e.g., human or animal) is experiencing. In addition, the similarities and differences between selected epoch 44 probability profiles 88, 90 may aid researchers in identifying drugs or other stimuli that produce comparable results, benefits, side effects and the like.

Figure 9:
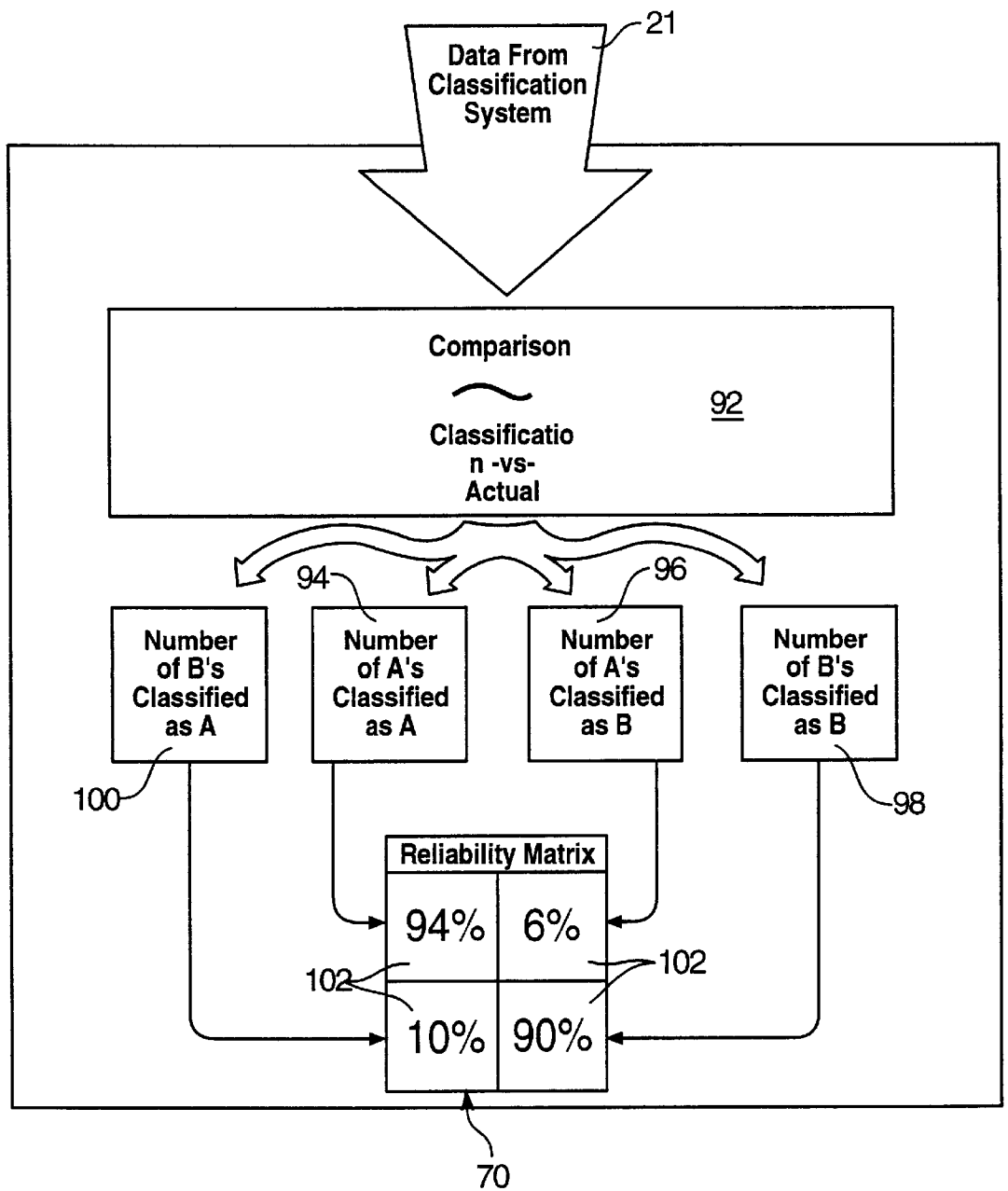
FIG. 9 is schematic block diagram of one presently preferred embodiment of a reliability matrix generator in accordance with the present invention.

Referring now to FIG. 9, in certain embodiments of the present invention, the classification accuracy of a particular interpretation map 22 may be determined by creating a reliability matrix 70. A reliability matrix may be created by a comparison function 92 comparing the classification of an epoch 44 as a particular event with the actual event associated with that epoch 44. For example, if a particular epoch 44 was classified as an event A epoch, then one of two things can be true. The epoch 44 can either be an event A epoch or the epoch 44 can be an event B epoch. The same may be true for an epoch 44 classified as an event B epoch.

After the comparison process 92, four numbers may be produced: the number of A event epochs classified as an A event epoch 94; the number of A event epochs classified as a B event epoch 96; the number of B event epochs classified as a B event epoch 98; and the number of B event epochs classified as an A event epoch 100. By dividing these numbers (i. e., the numbers indicated by the identifiers 94, 96, 98, 100) by the total number of actual epochs 44 related to that particular event, accuracy percentages 102 may be calculated.

Reliability percentages 102 may be incorporated into a reliability matrix 70. For example, if 100 event A epochs where classified and 94 where classified as an A event epoch, then the AA (matrix notation) percentage 102 would be 94%. That would leave 6 event A epochs that where classified as B event epochs, and the AB percentage 102 would be 6%. Likewise, BB and BA percentages 102 may be calculated in a similar manner.

The reliability matrix 70 provides the user with a better understanding of how much a particular classification may be trusted. In the illustrated example, a user may be quite comfortable that, using this particular interpretation map 22, an A event epoch 38 will indeed be classified as an A event. The classification system has shown that 94% of all A event epochs 38 were correctly classified.

Figure 10:
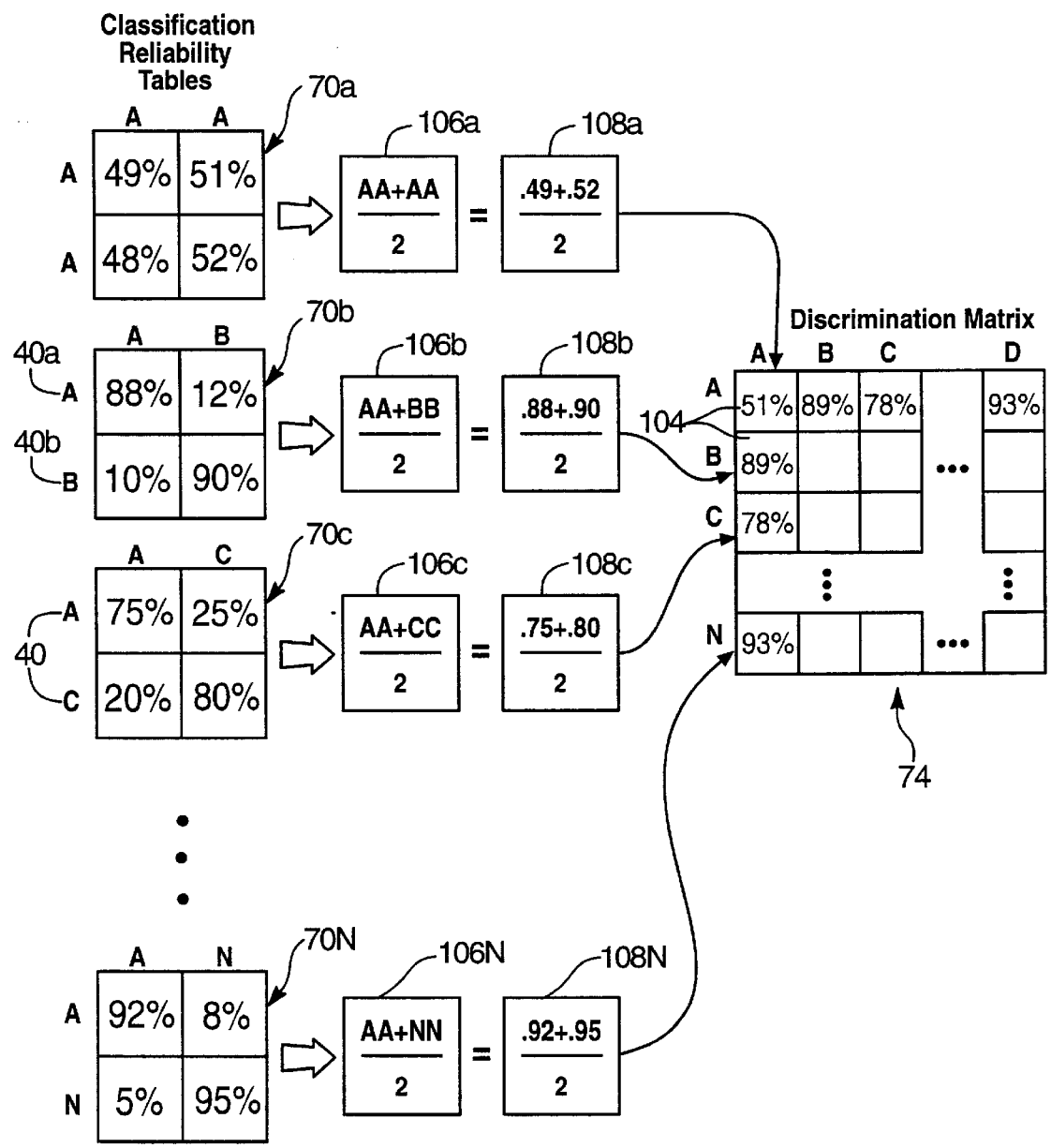
FIG. 10 is schematic block diagram of one presently preferred embodiment illustrating the use of multiple reliability matrices to create a single discrimination accuracy matrix in accordance with the present invention.

Referring now to FIG. 10, multiple reliability matrices 70a, 70b, 70c, . . . , 70n may be used to generate a discrimination accuracy matrix 74. Reliability matrices 70 provide the probability that two states (A and B, B and C, C and D, and the like) will be classified correctly. For example, a particular reliability matrix 70b may state that when compared with state B, an ERI 10 may correctly classify 88% of all state A epochs. When compared with state A, that same ERI 10 may correctly classify 90% of all state B epochs. A total classification accuracy 104 of the ERI 10 with respect to states A and B may be determined by averaging the two clarifications to produce 89%. FIG. 10 illustrates this total classification accuracy generation with matrix notation 106 as well as a numeric example 108.

In applications where the number of state A epochs analyzed does not equal the number of state B epochs analyzed, a total classification accuracy may be determined by dividing the total number of correct classifications (regardless of state) by the total number of epochs analyzed.

Once a total classification accuracy 104 has been generated for a particular pair of states, this value may be inserted in the appropriate locations of the discrimination accuracy matrix 74. It may be noted that discrimination matrices 74 are symmetric, thereby reducing the number of calculations necessary to complete the matrix 74. Reliability matrices 70 may be generated and total classification accuracies 104 calculated using selected state pairs until the discrimination matrix 74 is complete.

A complete discrimination matrix 74 may provide the user with a comparison of the similarities of a variety of states. It may be noted that the diagonal of the discrimination accuracy matrix 74 may often contain values near 50%. The diagonal contains total classification accuracies 104 of a particular state compared against itself. As would be expected, an ERI 10 cannot repeatable distinguish a state 40 from itself, therefore, it typically is right half the time and wrong half the time.

Referring now to FIG. 11, a discrimination matrix 74 may be converted to a dissimilarity matrix 76 by a dissimilarity transformation 110. Dissimilarity matrices 76 provide a method for comparing how different a particular event 40a or state 40a is from another event 40b or state 40b. As can be seen, the diagonal contains low dissimilarity values. This is to be expected for the state 40 having a low dissimilarity with itself.

Referring now to FIG. 12, a discrimination matrix 74 may be converted to a similarity matrix 78 by a similarity transformation 112. As can be seen, the diagonal contains high similarity values. This is to be expected for the state 40 tending to be very similar to itself.

Sas appreciated, similarity matrices 78 may be particularly useful. A similarity matrix 78 enables a user to objectively calculate how similar the effects of a particular state 40a are to the effects of another state 40b. This comparison may have a profound impact on the ability of a user to predict and quantify the effects of a particular drug (state A) with a drug (state B) having known effects.

Figure 13:
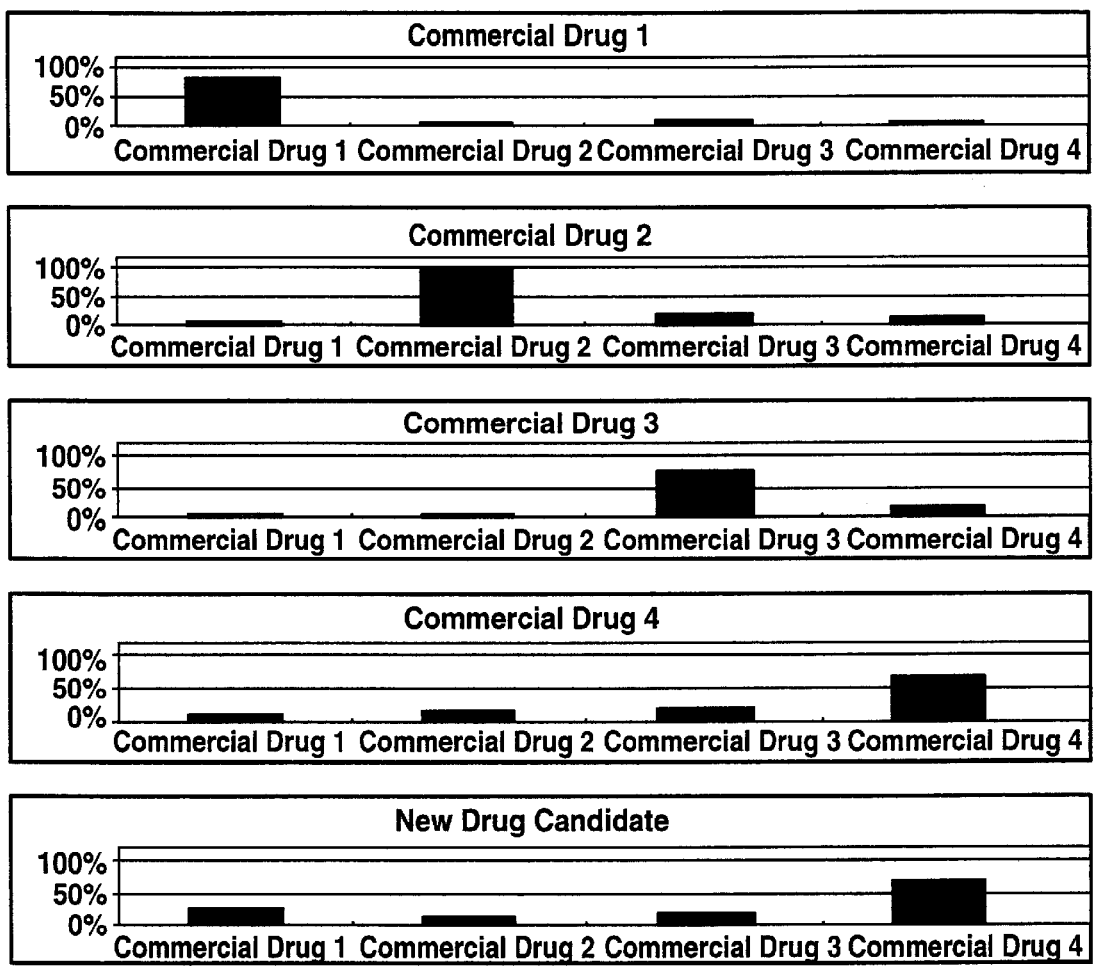
FIG. 13 is one presently preferred embodiment of a similarity matrix comparing the characteristics of a theoretical new drug candidate against the characteristics of theoretical commercial drugs 1–4 in accordance with the present invention.

Referring now to FIG. 13, suppose the effects (helpful and harmful) of a commercial drug 4 are well known and documented. In an ERI 10 comparison it is found that a newly discovered, much less expensive drug candidate is very similar to commercial drug 4. Therefore, there is a high probability that the new candidate drug will have the same effects as commercial drug 4, for it is affecting the observed entity (e.g., human or animal) in a very similar way. Therefore, such objective analysis of the effects of the new candidate drug may greatly speed the testing and clinical trials of the new drug and allow it to reach the consumer much faster with a better understanding of its effects and side effects.

A similarity matrix 78 also provides the ability to perform improved, more objective drug modeling. Similar to the engineer who places his model plane in a wind tunnel to see how a complete plane will act in actual flight, a drug researcher may apply a particular drug in an animal test and accurately predict how it will affect humans. For example, suppose the effects of drug X on humans as well as rats are well known and documented. In an ERI 10 comparison it is found that a newly discovered drug Y produces a signature or "fingerprint" in a rat very similar to that of drug X. A prediction using an ERI 10 in accordance with the present invention may provide much more accurate predictions or extrapolations to humans because the similarity is not calculated from symptoms. Rather, the similarity may be objectively measured in the fundamental effects the drug has on a particular and fundamental aspect of the observed entity, such as the brain.

Figure 14:
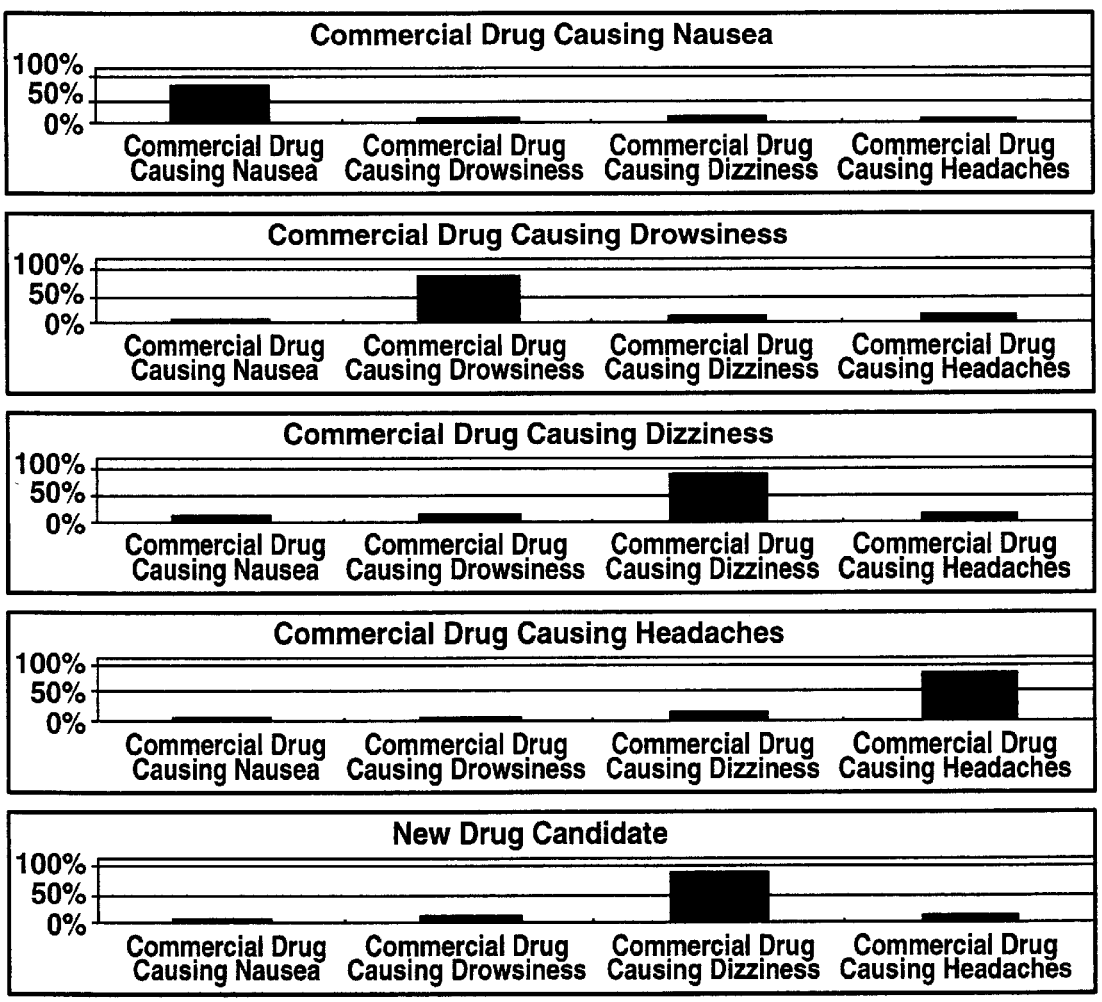
FIG. 14 is one presently preferred embodiment of a similarity matrix used to screen for the neurological side effects of a theoretical new drug candidate against known neurological side effects of theoretical commercial drugs exhibiting nausea, drowsiness, dizziness, and headaches respectively in accordance with the present invention.

Referring now to FIG. 14, another powerful way to test for drug similarity between drugs M and N, may be to generate a pre-injection to post-injection interpretation map for drug M, and then to use that very same map to classify both pre and post-injection data corresponding to drug N. If the interpretation map created for drug M is able to accurately classify the presence and absence of drug N, then there is a high likelihood of similarity between the two drugs. On the other hand, if the interpretation map does not work with drug N (low classification accuracy) then drug N is likely to be dissimilar to drug M in its affects on the observed entity.

In this manner, various interpretation map "crossover" drug comparison tests can be made. An interpretation map 22 may be generated by epochs 38 corresponding to a related group of several drugs, as shown in FIG. 1. For example, an interpretation map 22 may be built to identify a distinct class or type of drug. This map 22 could then be subsequently used to measure, by calculating the classification accuracy, the degree of membership of a new drug candidate to the known drug class.

Figure 15:
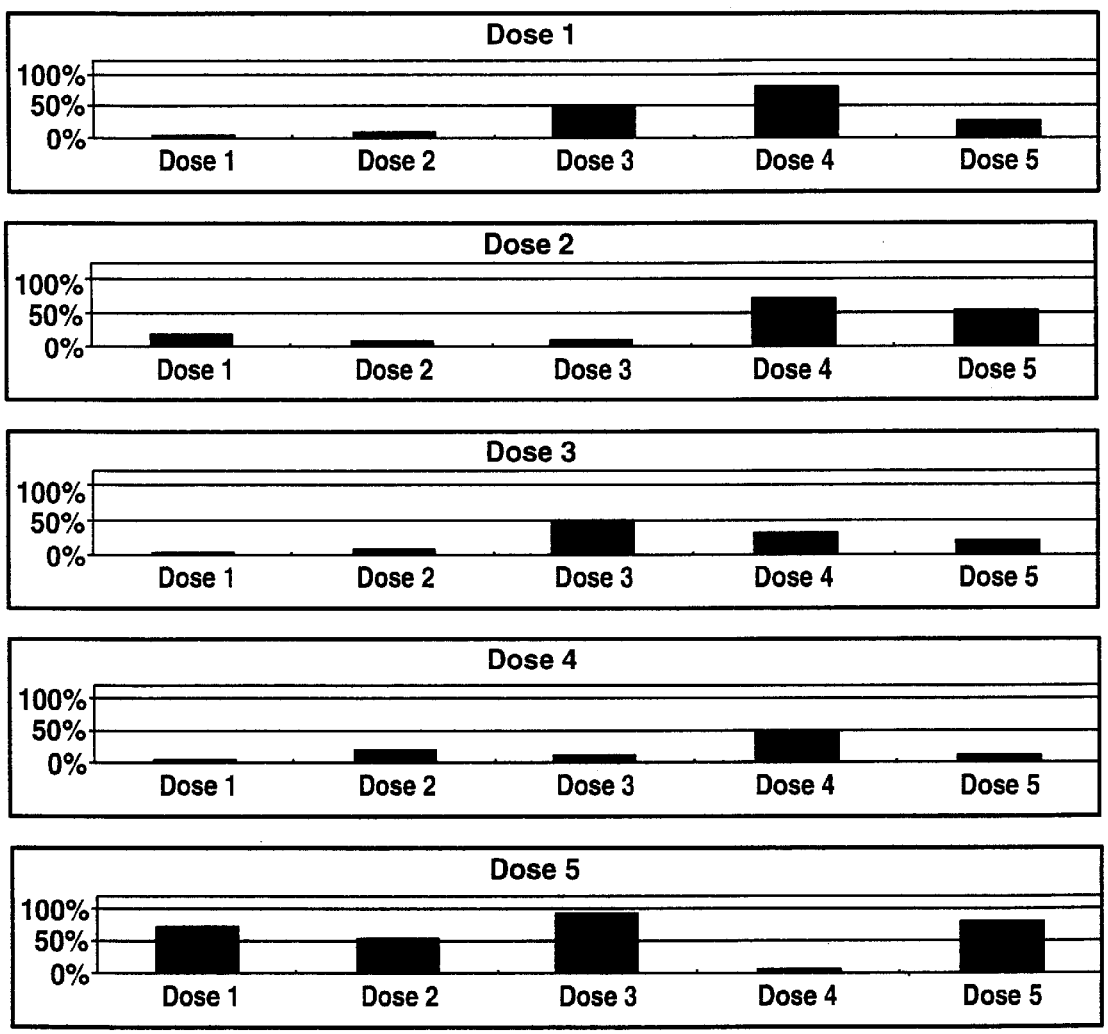
FIG. 15 is one presently preferred embodiment of a similarity matrix used to compare the theoretical results of different doses of a particular drug in accordance with the present invention.
Figure 16:
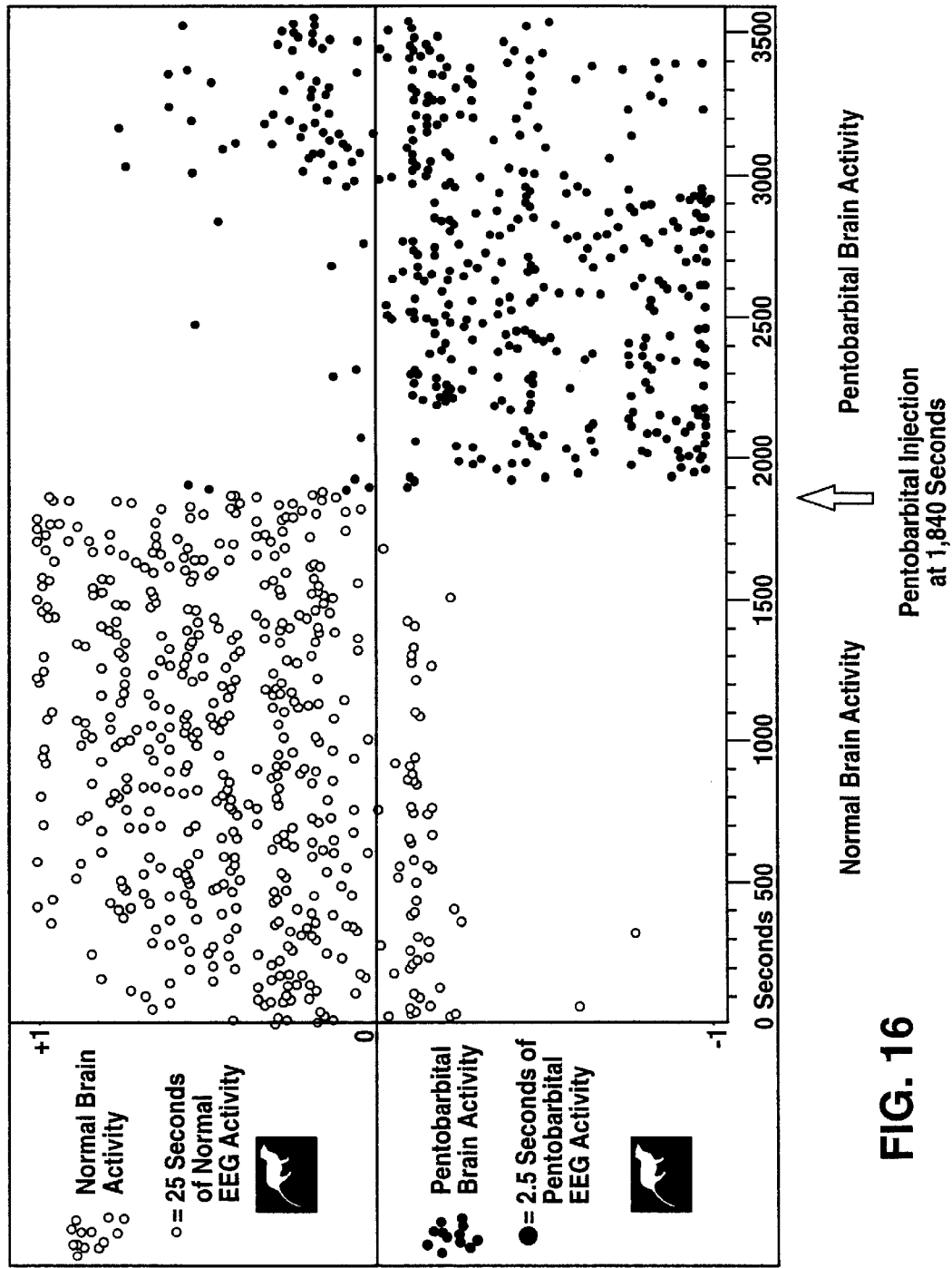
FIG. 16 is one presently preferred embodiment of an experimentally derived EEG activation value plot for pentobarbital in accordance with the present invention.

Referring now to FIG. 15, a similarity matrix may also be used to identify relationships between one dose of a given drug and a collection of other doses all of the same drug. In this way, dose response relationships can be determined according to the way a particular set of doses affect an observed entity. As can be seen, does one and dose two are most likely to produce a similar result. Dose five will most likely produce a very different response in the observed entity than any of the other doses.

The following examples will illustrate the invention in further detail. It will be readily understood that the present invention, as generally described and illustrated in the Examples herein are merely exemplary of the presently preferred embodiments of the present invention. Thus, the following more detailed description of the presently preferred embodiments of the methods and formulations of the present invention, as represented in Examples I through V are not intended to limit the scope of the invention, as claimed, but are merely representative of the possible embodiments and applications of the present invention.

EXAMPLE I

The subjects were six male Sprague-Dawley rats with individual masses between 400 and 500 grams. The rats were individually caged in a temperature and humidity controlled environment with a 12 hour light/dark cycle. Food and water were available ad libitum.

All behavioral testing was done in the dark during the dark cycle. For the chronic implant, rats were anesthetized with a one-time 50 mg/kg intraperitoneal dose of pentobarbital and supplemented with 20–27 mg/kg intramuscular ketamine. A one-time injection of 0.2 mg/kg subcutaneous atropine was administered to mitigate fluid build-up in the airways. Four stainless steel skull screws (size 000) were implanted bilaterally over the parietal and frontal cortices and served as EEG leads (120 $\mu$m HML-coated stainless steel wire).

A bundle of eight teflon-insulated microwires (50 to 62 $\mu$m) was also implanted into the VTA (−5.8 mm AP, 0.7 mm ML, and 7.8 mm from the cortical surface) and served as a depth electrode for subcortical recordings. Two silver wires serving as grounding leads were wrapped around seven to eight skull screws (size 00) and the implant was cemented with dental acrylate. The rats were given at least one week of recovery following surgical implantation before experimentation.

Spontaneous EEG was recorded in rats using a detachable headset containing 16 field effect transistors for impedance lowering, one for each microwire and EEG electrode. EEG was differentially amplified (10,000×; parietal versus parietal, parietal versus frontal, and frontal versus frontal configurations) and filtered (0.1–100 Hz at −3 dB; 60 Hz anti-aliasing notch filter) by an Axon Instruments CyberAMP 380 signal conditioner.

Motor activity was assessed by a piezoelectric activity transducer cemented to underside of the suspended floor of the chamber. Piezoelectric activity was filtered at 0.1–100 Hz (−3 dB) and amplified 10–100 times by an Axon Instruments CyberAMP 380 signal conditioner. EEG and piezoelectric recordings were digitized at 1000 Hz with a National Instruments PCI-MIO-16XE-10 multifunction I/O board in a Pentium III computer and streamed to disk for later analysis. The duration of each recording session was one hour.

A video recording system consisting of a camcorder, video graphics cards, Macintosh Quadra 950 computer, a video monitor and a videocassette recorder was employed to monitor rat behavior. Graphical windows displaying EEG and piezoelectric activity were superimposed on the video signal for off-line correlation of behavior with electrophysiological responses. Piezoelectric and EMG activity was analyzed in four second activity epochs by a root-mean square processing algorithm, and five minutes of epochs were averaged at ten minute pre and five minute post drug injection for determinations of ataxia.

Drug-induced ataxia was determined behaviorally when the animals splayed their hind-quarters and evinced abnormal gait with intermittent loss of postural control. The intermittent loss of postural control was coincident with high voltage paroxysms on the piezoelectric and EMG recordings.

All drugs were dissolved in physiological saline (0.9%) and administered intravenously. Ethanol was administered as a 10% w/v solution. All drugs, as well as saline, were injected over two to three minutes thirty minutes into the recording session.

Referring now to FIGS. 16–24, each small circle represents a two second epoch of highly processed EEG activity. For this particular type of processing, the brain normally (pre-injection) exhibits mostly positive spectrum (from −0.25 to +1) of EEG activation values.

Following the injection of the drug, the activation values are represented by small circles having been darkly shaded. Note that the processed EEG data exhibits a drifted spectrum of activity (from −1 to +0.25) with mostly negative activation values. In each Figure, there is a period of time required for the drug to cross the blood-brain barrier and enter the brain. This effect is readily visible through appropriately processed EEG epochs.

The ability to non-invasively and accurately track and monitor the progression of a drug across the blood-brain barrier in real time (on time scales of seconds to minutes) opens the door to a better understanding of this barrier, and sheds light on the effect of a given drug has on brain function. The ability to accurately test which drugs are able to cross the blood-brain barrier and to monitor the time course of the crossing, constitutes a powerful new tool for the evaluation and acceleration development of neurological drug candidates.

Figure 17:
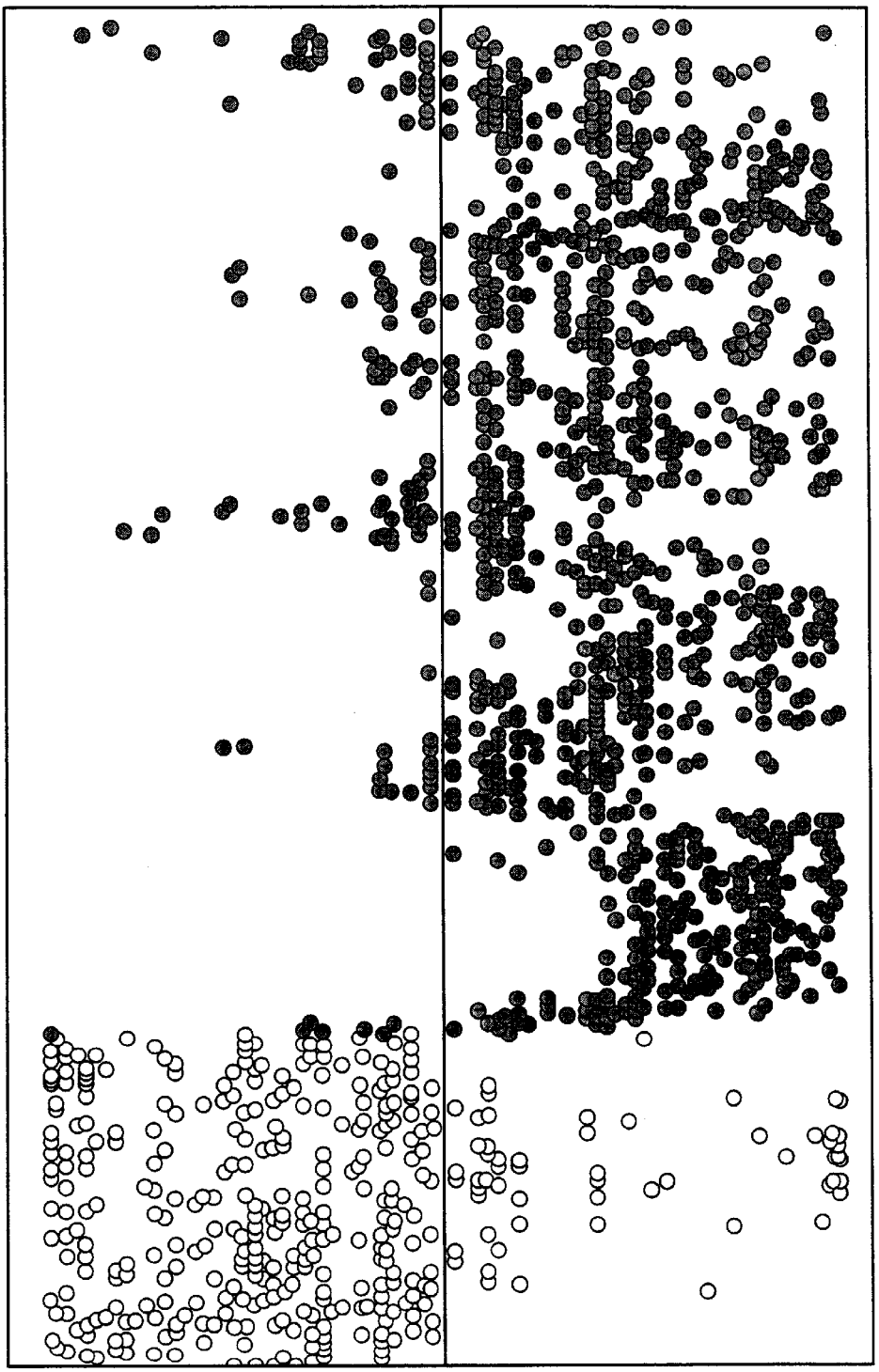
FIG. 17 is one presently preferred embodiment of an experimentally derived EEG activation value plot for pentobarbital at a low resolution in accordance with the present invention.
Figure 18:
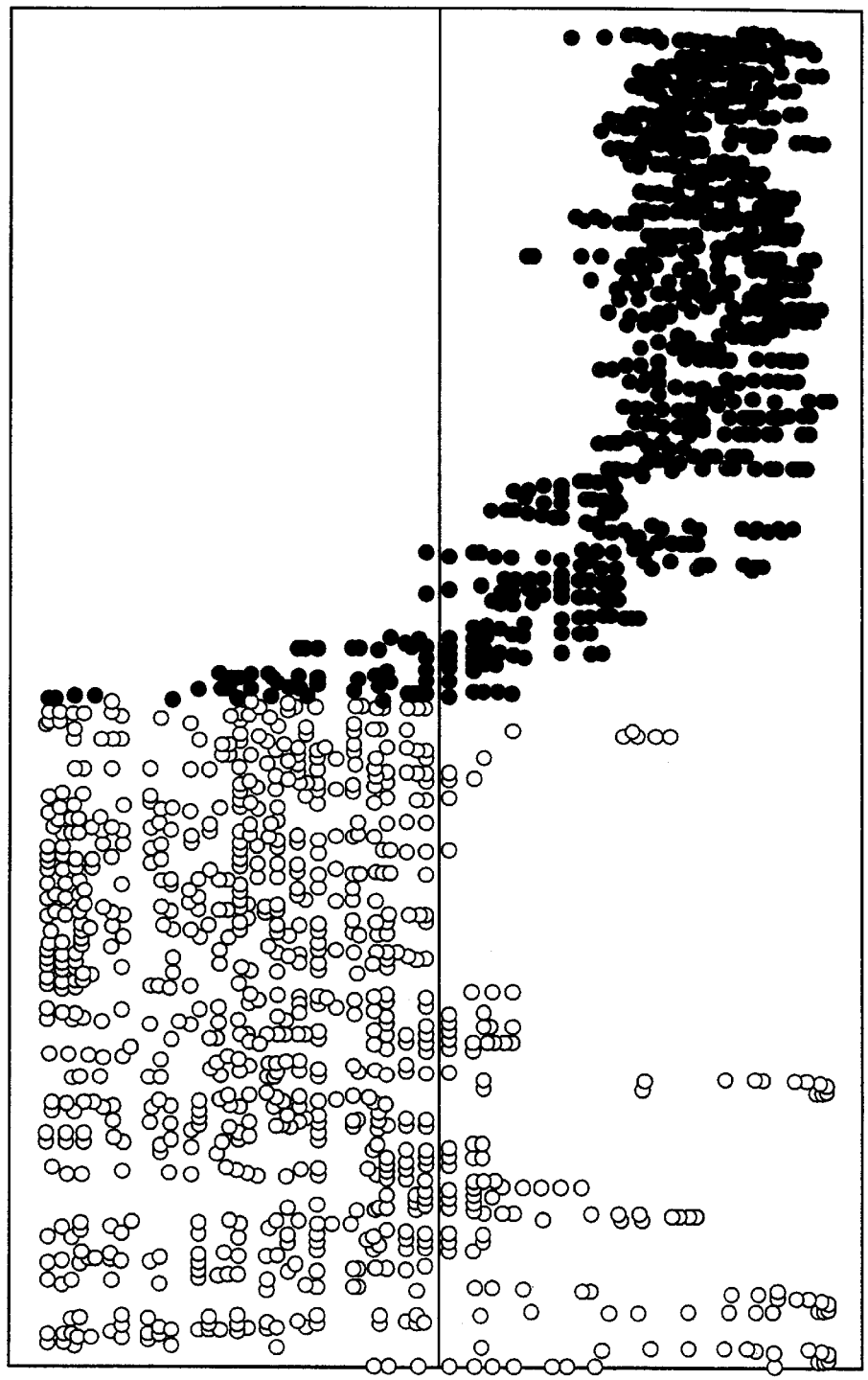
FIG. 18 is one presently preferred embodiment of an experimentally derived EEG activation value plot for pentobarbital at a medium resolution in accordance with the present invention.
Figure 19:
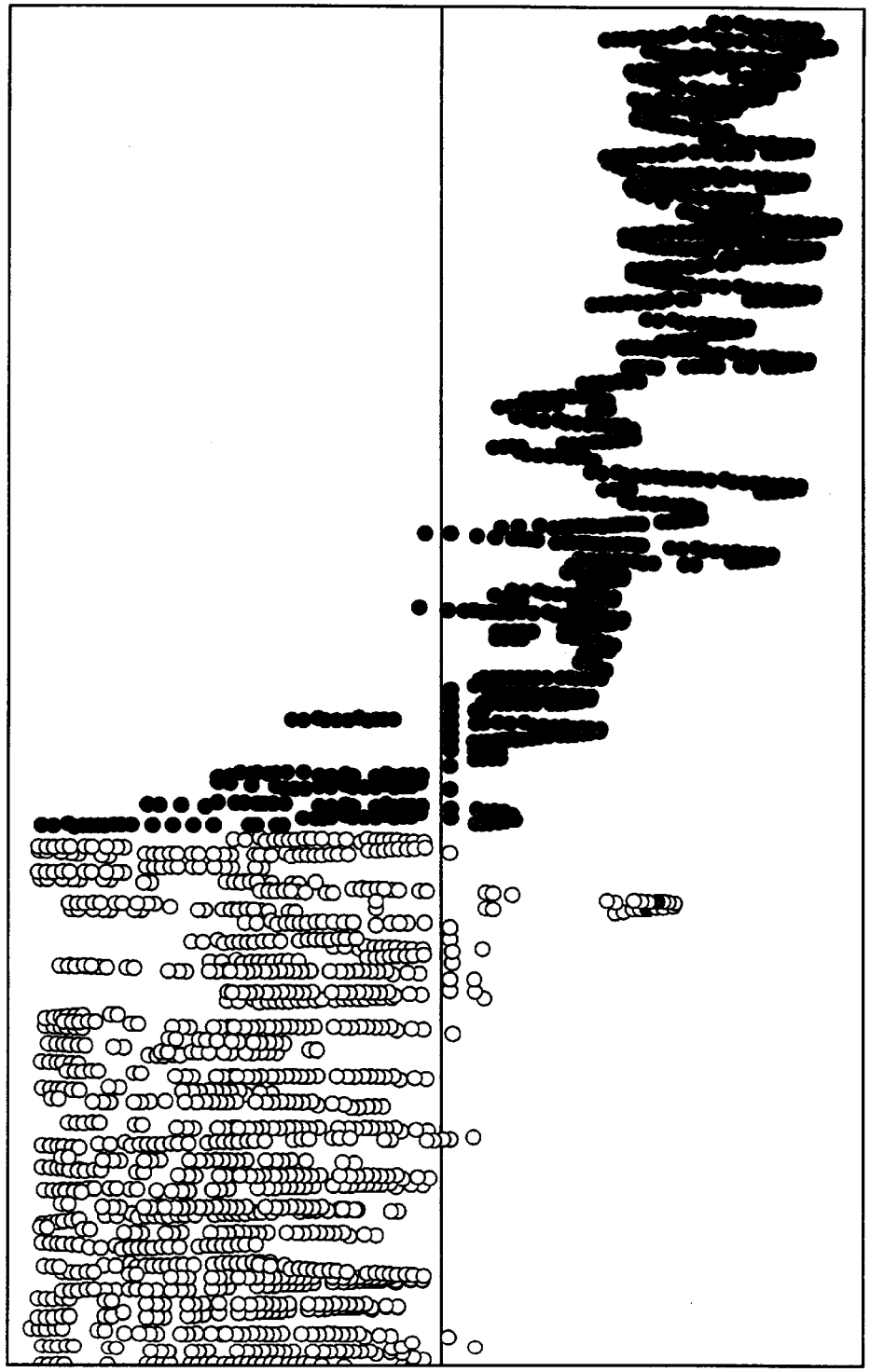
FIG. 19 is one presently preferred embodiment of an experimentally derived EEG activation value plot for pentobarbital at a high resolution in accordance with the present invention.
Figure 20:
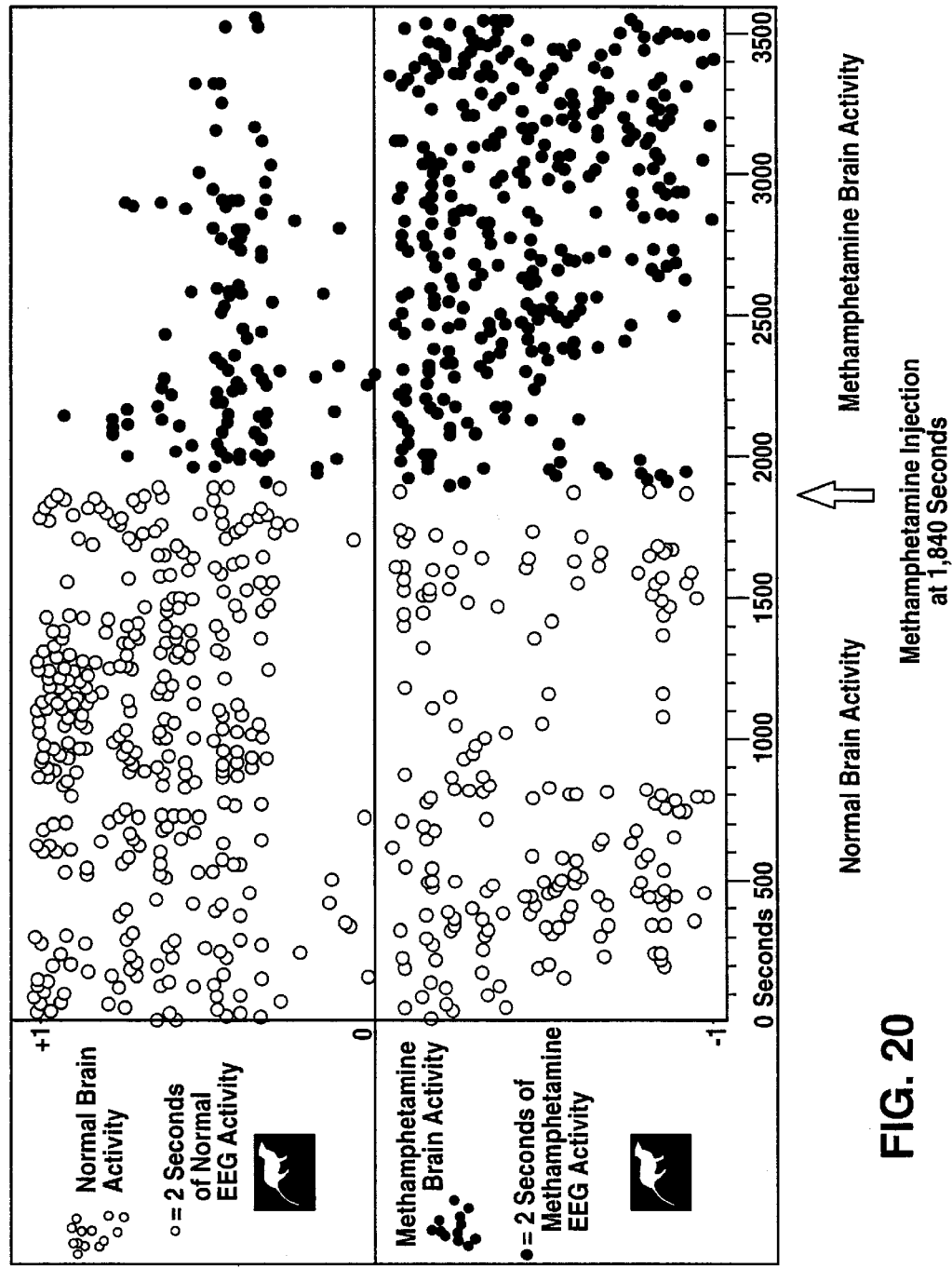
FIG. 20 is one presently preferred embodiment of an experimentally derived EEG activation value plot for methamphetamine in accordance with the present invention.
Figure 21:
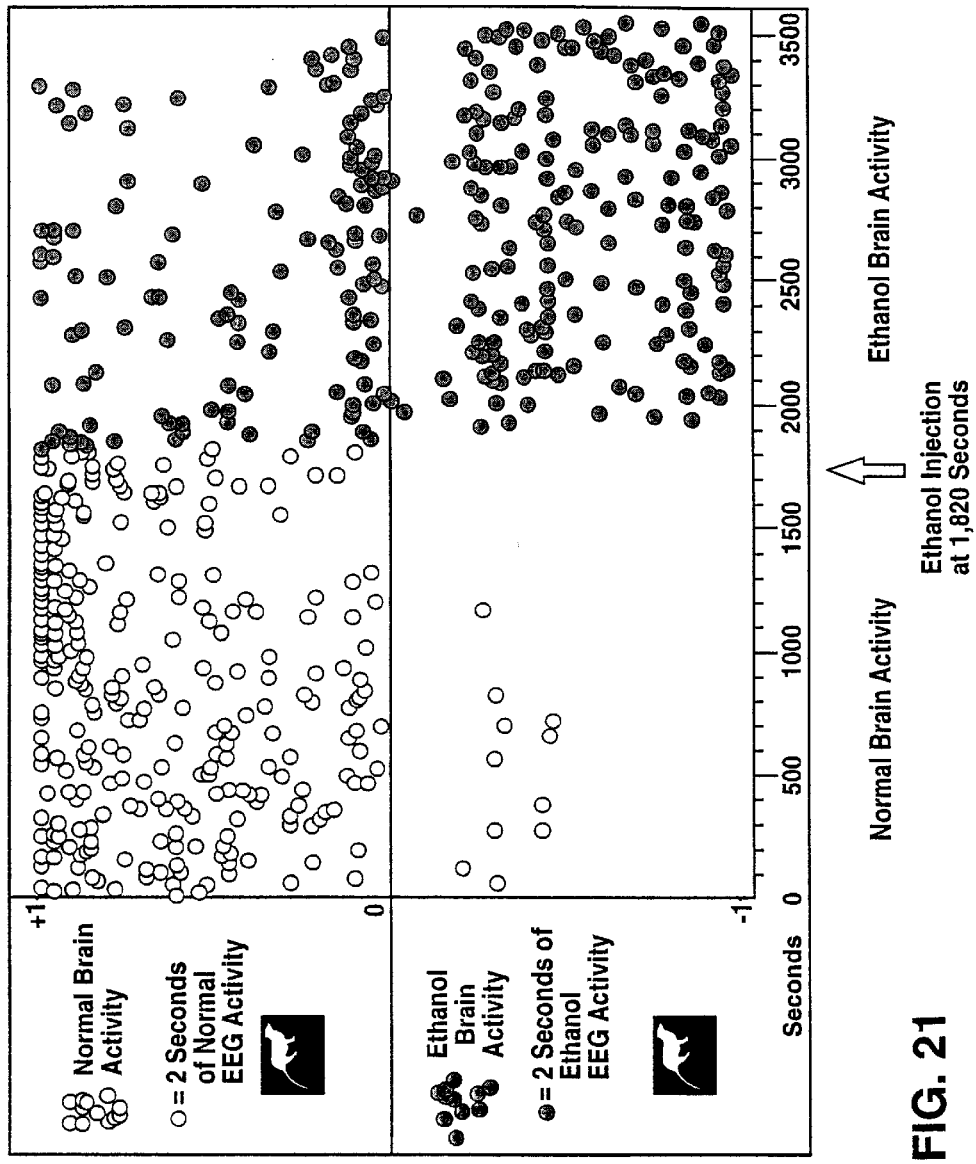
FIG. 21 is one presently preferred embodiment of an experimentally derived EEG activation value plot for ethanol in accordance with the present invention.
Figure 22:
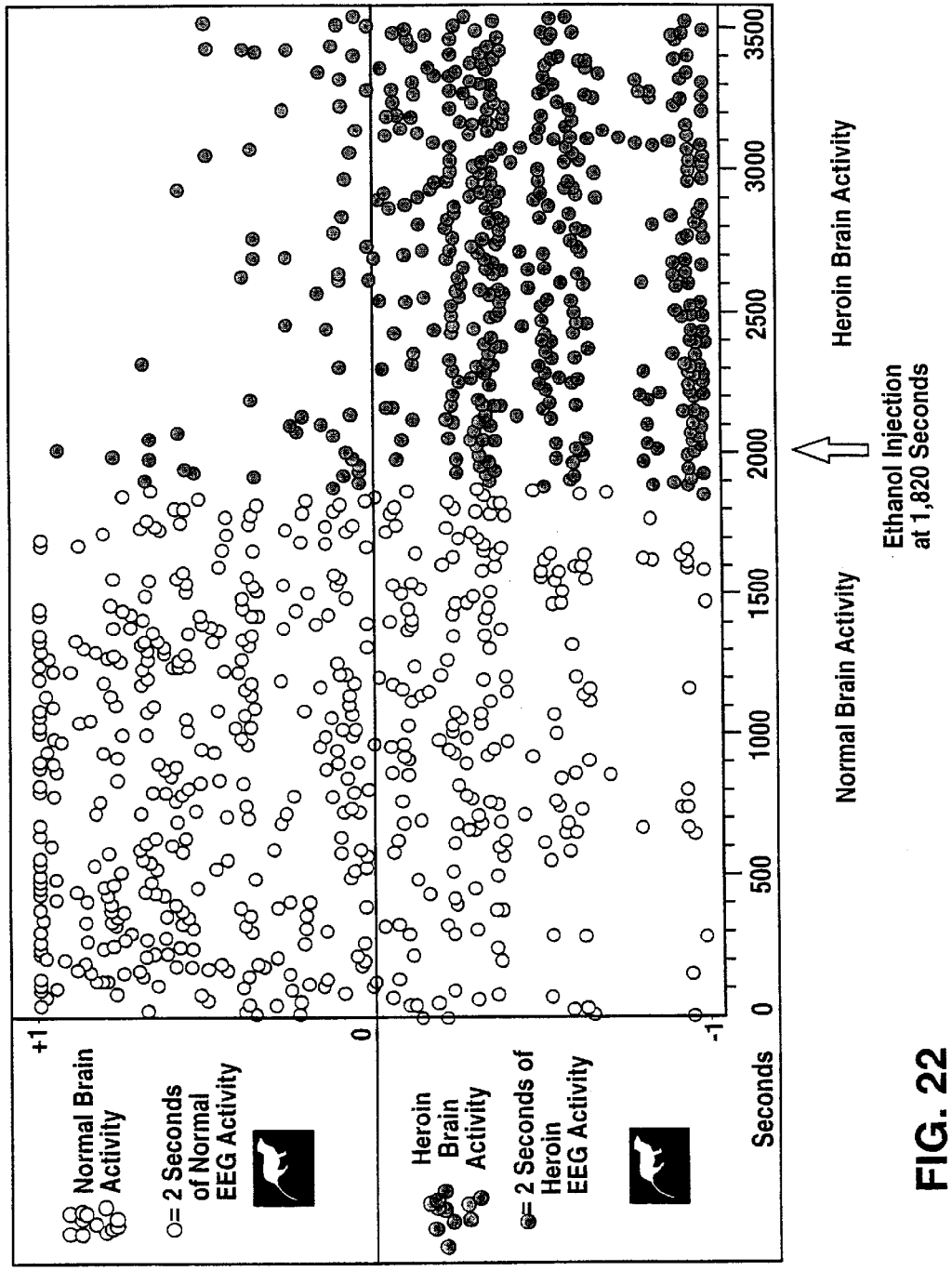
FIG. 22 is one presently preferred embodiment of an experimentally derived EEG activation value plot for heroin in accordance with the present invention.
Figure 23:
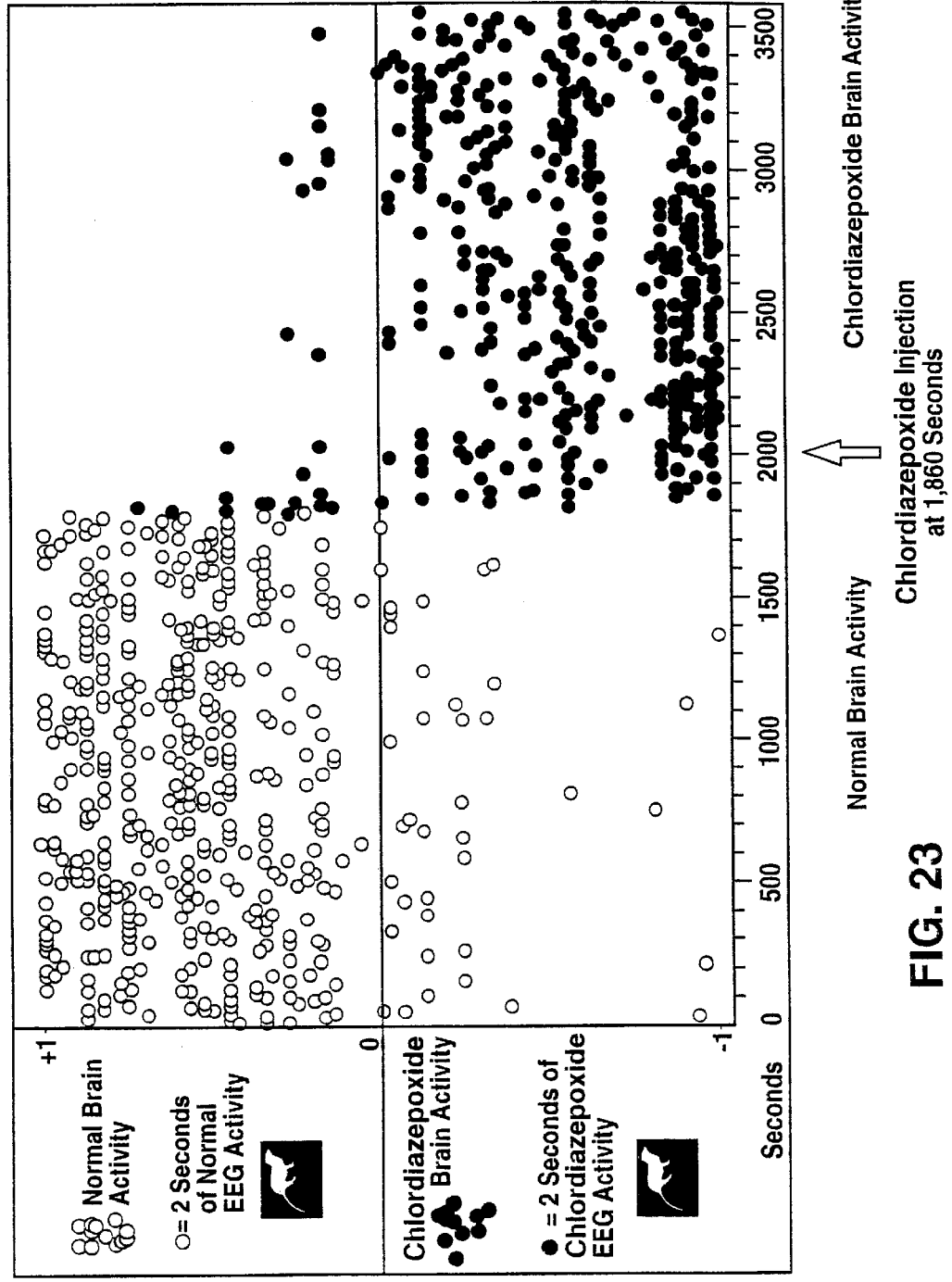
FIG. 23 is one presently preferred embodiment of an experimentally derived EEG activation value plot for chlordiazepoxide in accordance with the present invention.
Figure 24:
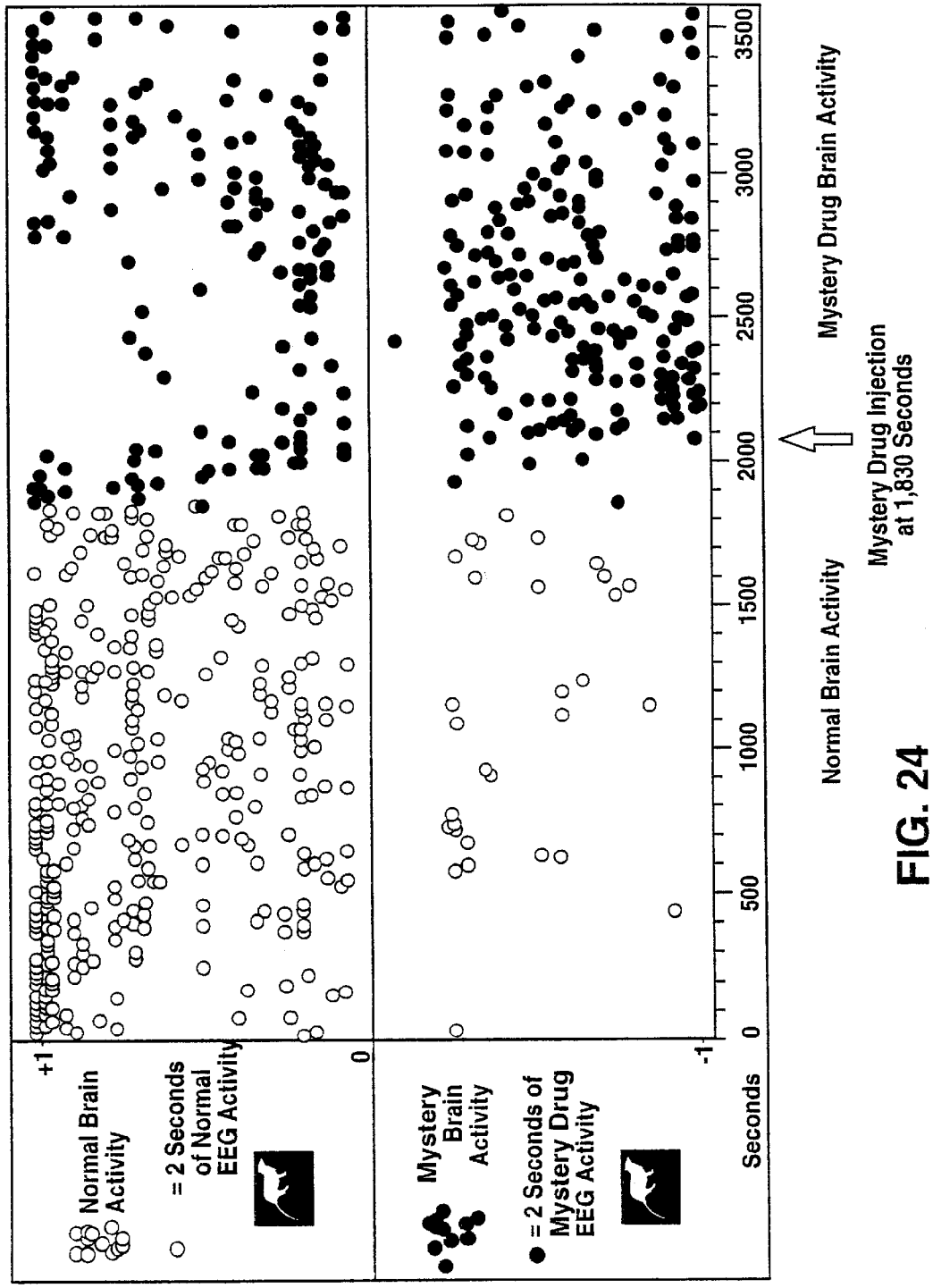
FIG. 24 is one presently preferred embodiment of an experimentally derived EEG activation value plot for an unknown drug later determined to be ethanol in accordance with the present invention.

Referring specifically to FIGS. 17–19, EEG epochs are parsed by skipping over just one or a few frames, where each frame is a data point or a time slice. This may generate a large number of EEG epochs (each epoch being similar to the previous epoch except for a small amount of EEG data corresponding to a small shift in time). These epochs are then introduced to an ERI for classification whereby activation values are generated which reflect the degree of presence or absence of particular patterns of features in the raw EEG data epochs.

By making the time shift (corresponding to a particular selected number of frames) increasingly smaller in the parsing operation, its possible to continually increase the temporal resolution of the blood-brain barrier crossing to achieve very high resolutions and thereby make it possible to accurately distinguish the slope of the crossing or the rate of change of CNS activity over time as the drug establishes itself in the brain or exerts its effect either directly or indirectly on the brain.

For example, FIG. 17 provides an example of a regular low resolution Pentobarbital blood-brain barrier drug crossing for a particular rat (named R850 in this case). The horizontal axis corresponds to one hour of time. Note that immediately after the intravenous drug injection there is a marked and dramatic shift or change which occurs in the distribution of activation values. This zone or region (the time immediately before and immediately after the drug injection) in which the change occurs can be "zoomed in" by parsing the data prior to introducing it to the classification algorithm which generates the activation values.

FIG. 18 is a medium resolution Pentobarbital plot (time axis is about 10 minutes duration). FIG. 19 is a high resolution Pentobarbital plot (time axis is about 5 minutes duration) of activation values corresponding to the same EEG data set, in which the number of frames shifted from one epoch to the next is rather small. By increasing the sampling rate and decreasing the number of frames shifted from epoch to epoch, and also by decreasing the size of the epoch, it is possible to achieve a very high degree of temporal resolution (even significantly higher than shown in these Figures) to track the rate at which brain activity changes due to the increasing influence of a drug as it enters an animal or human body.

It may be that the rate of change of central nervous system (CNS) activity and the temporal shape of the activation values during the crossing, may be indicative of the type of drug present in the body. This is because different drugs tend to have distinct mechanisms of inhibition or activation of receptors on cell membranes. Different drugs also have other influences on various brain processes such that each drug may establish its CNS activity changes at a distinct and characteristic rate.

Figure 25:
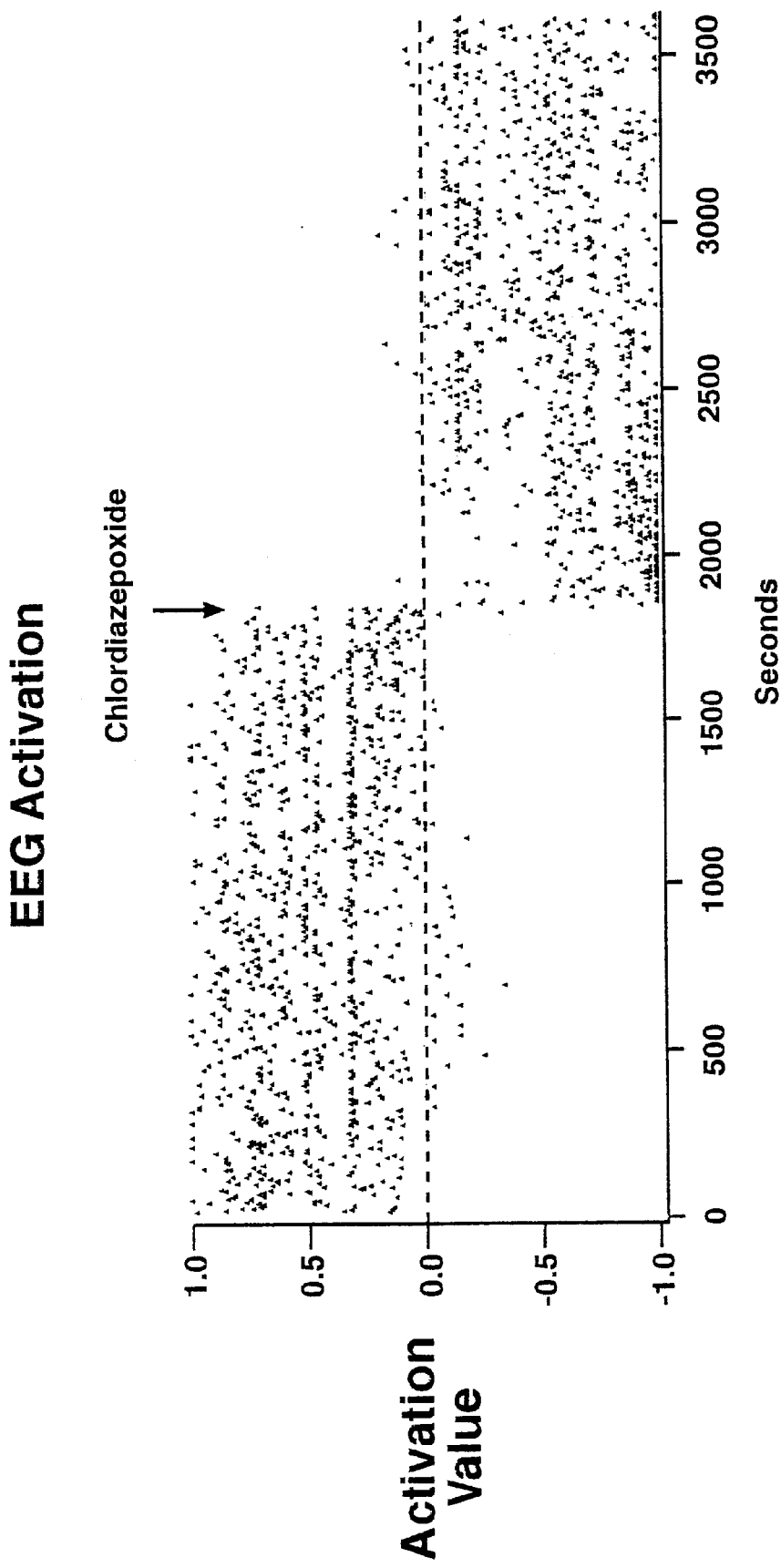
FIG. 25 is one presently preferred embodiment of an experimentally derived EEG activation value plot for chlordiazepoxide in accordance with the present invention.
Figure 26:
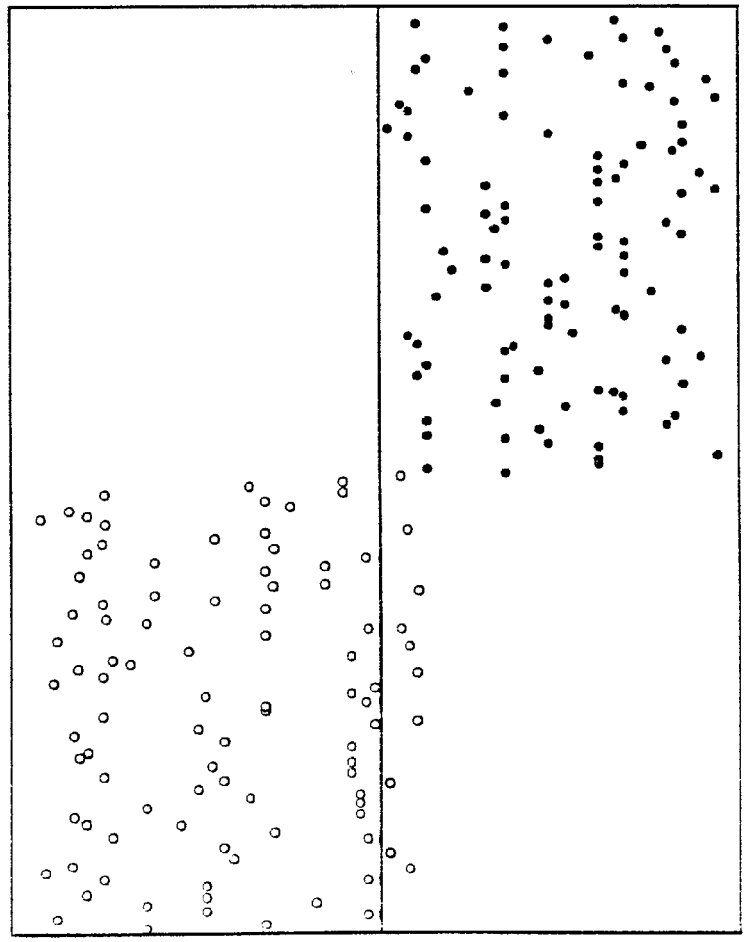
FIG. 26 is one presently preferred embodiment of an experimentally derived EEG activation value plot comparing the epoch values for chlordiazepoxide and ethanol in accordance with the present invention.
Figure 27:
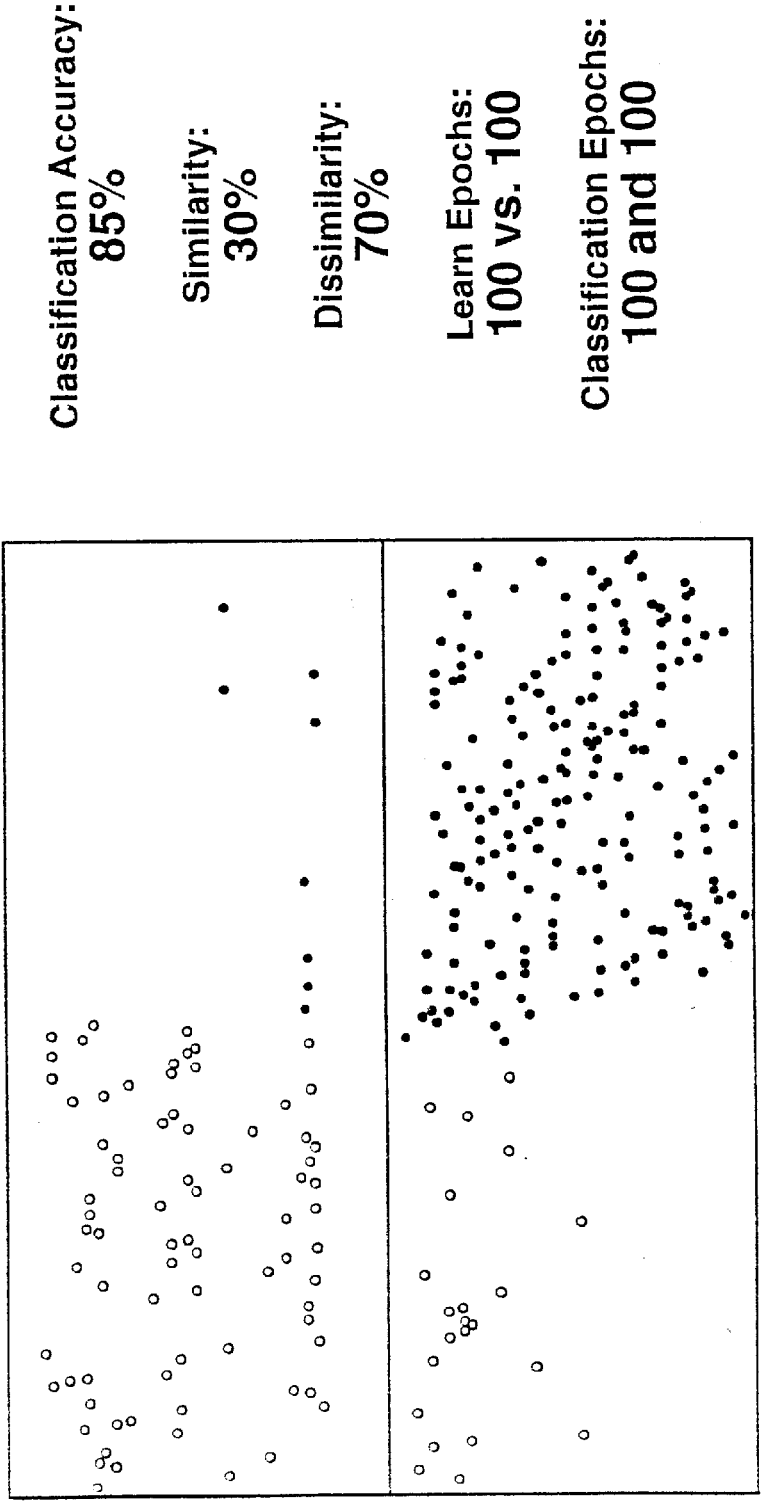
FIG. 27 is one presently preferred embodiment of an experimentally derived EEG activation value plot comparing the epoch values for pentobarbital and chlordiazepoxide in accordance with the present invention.
Figure 28:
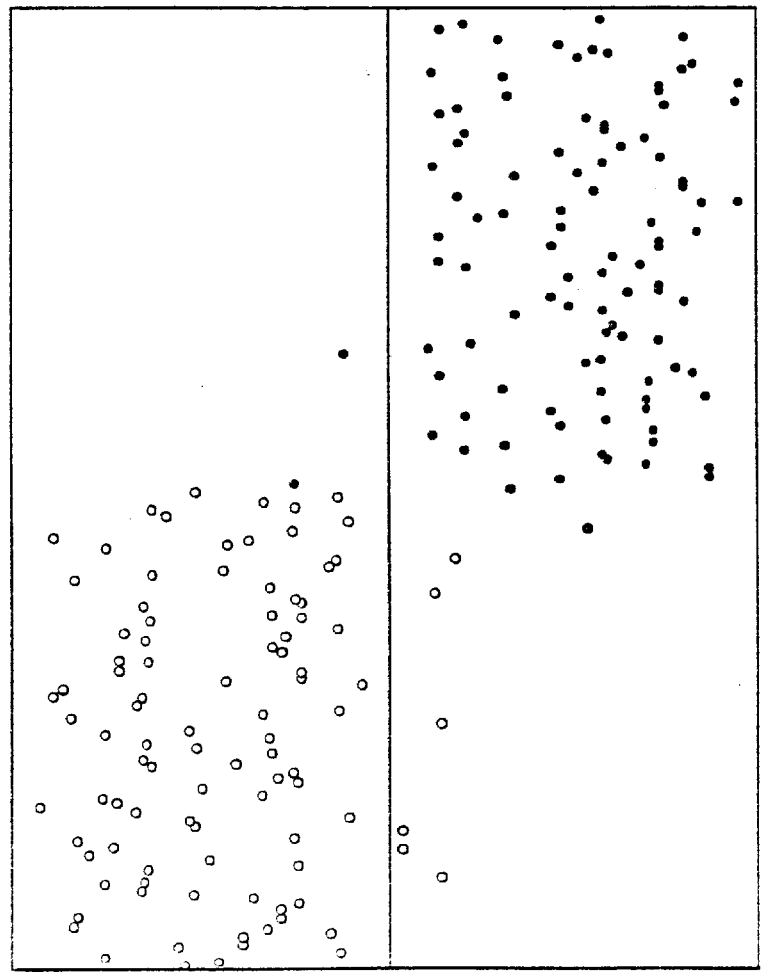
FIG. 28 is one presently preferred embodiment of an experimentally derived EEG activation value plot comparing the epoch values for pentobarbital and ethanol in accordance with the present invention.
Figure 29:
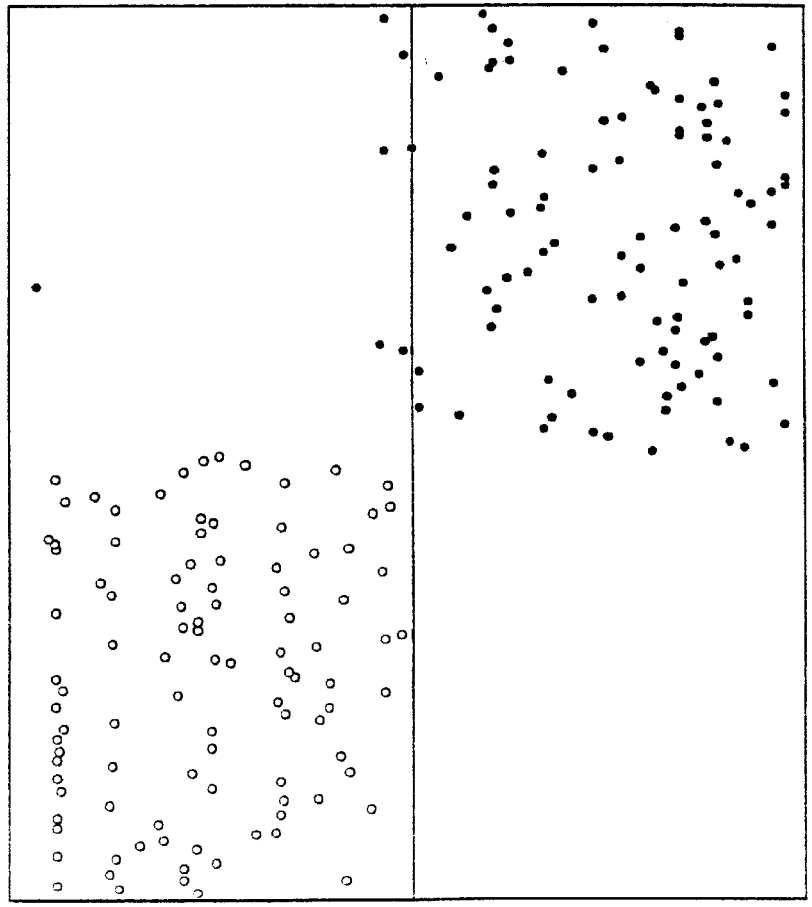
FIG. 29 is one presently preferred embodiment of an experimentally derived EEG activation value plot comparing the epoch values for pentobarbital and heroin in accordance with the present invention.
Figure 30:
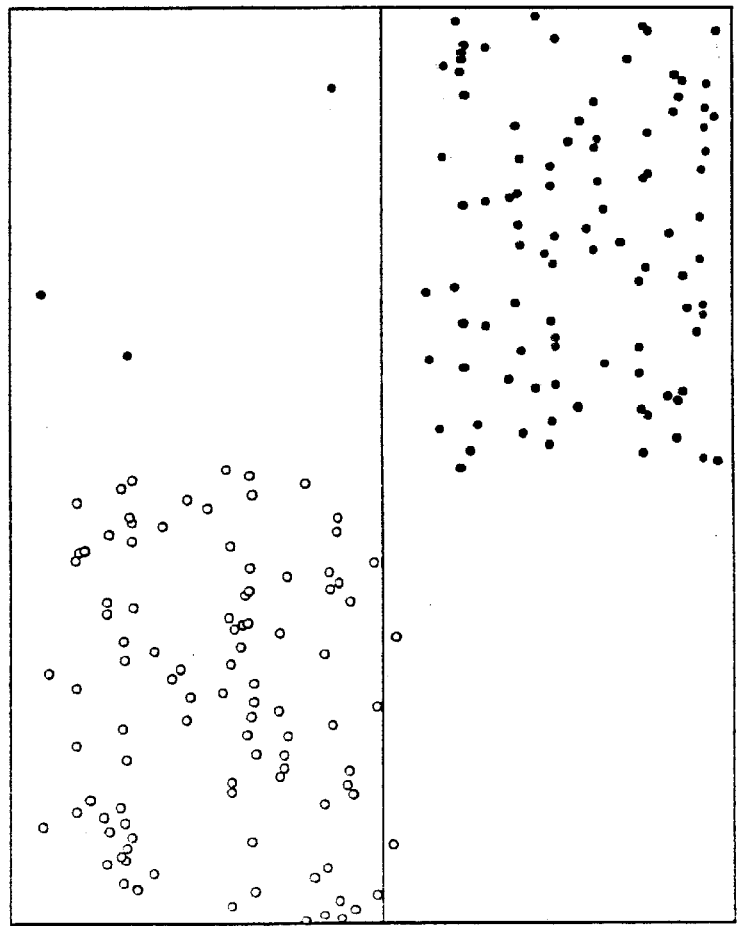
FIG. 30 is one presently preferred embodiment of an experimentally derived EEG activation value plot comparing the epoch values for chlordiazepoxide and heroin in accordance with the present invention.

Referring now to FIG. 25, the time course of the effects of each of the drugs on EEG activation was determined for each rat. The activation value plot contains one hour of recorded and processed EEG data. The EEG data was divided into epochs of two seconds in duration. Chlordiazepoxide (6.0 mg/kg) was administered intravenously thirty minutes into the sampling. Activation values represent the degree of presence (greater than zero) or absence (less than zero) of a pattern of features (e.g. a pattern of phase-weighted frequencies) inherent in the raw spontaneous EEG. The learning algorithm identified feature patterns that optimally discriminate between chlordiazepoxide and non-drug states.

Referring to FIGS. 26–30, activation plots comparing drug A versus drug B were created from one hundred (100) classification epochs of post-injection drug A and post-injection drug B for all the drugs (i.e., saline isovolumic with ethanol, pentobarbital 10.0 mg/kg, chlordiazepoxide 6.0 mg/kg, ethanol 1.0 mg/kg, heroin 0.3 mg/kg, methamphetamine 2.0 mg/kg and an unknown drug).

Figure 31:
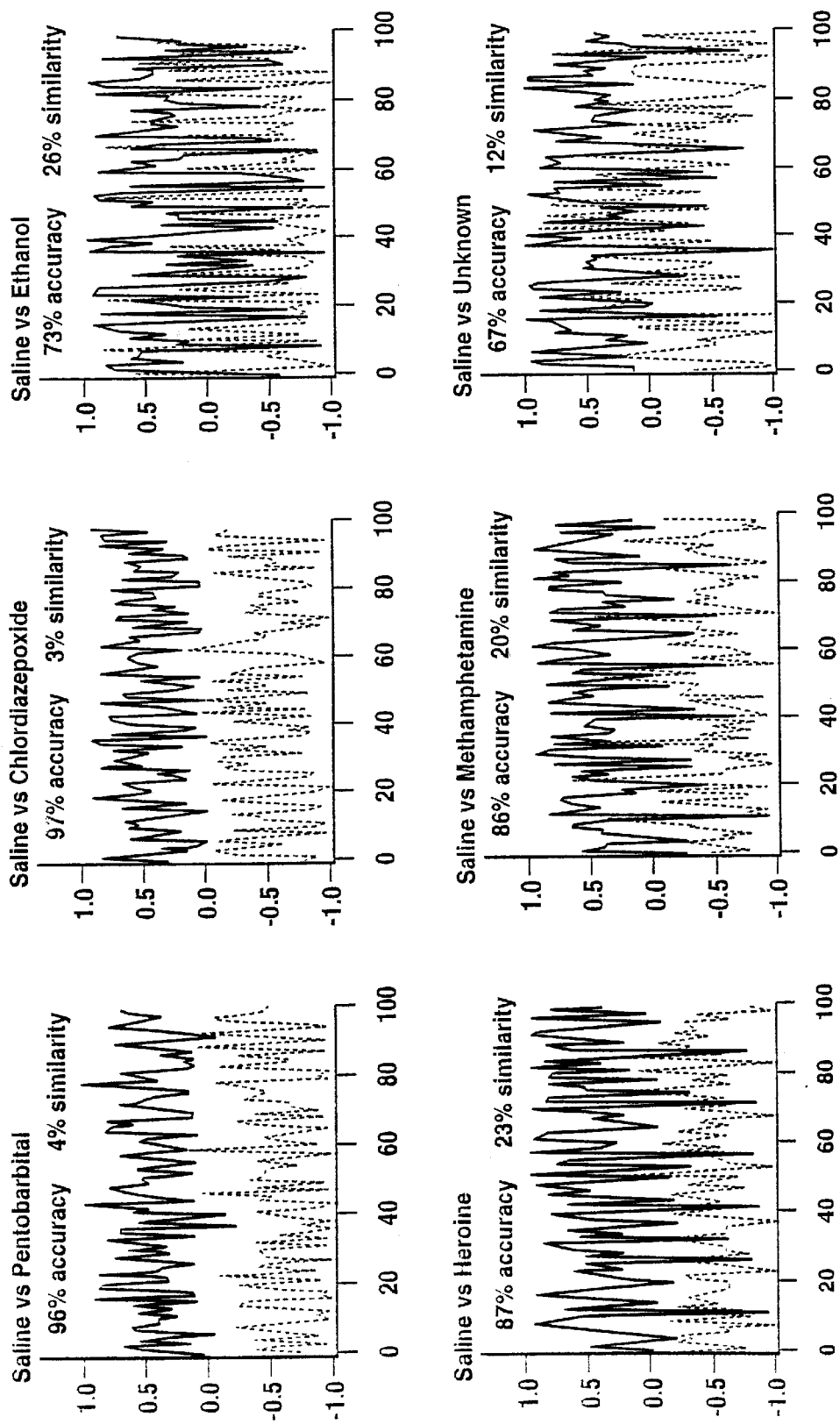
FIG. 31 is an alternative embodiment of an experimentally derived EEG activation value plot comparing the epoch values for saline paired against pentobarbital, chlordiazepoxide, ethanol, heroin, methamphetamine, and the unknown drug in accordance with the present invention.

FIG. 31 compares the activation plots for saline versus all the drugs in one rat. The classification epochs were distinct from the learning epochs in which one hundred (100) learned epochs for saline and a paired drug were used to build an interpretation map, which was then used to classify the epochs for saline versus that drug. These plots demonstrate quantitative differences between saline activation and the other drugs. For example, the activation differential between saline and chlordiazepoxide was more than that between saline and ethanol.

The doses of pentobarbital, chlordiazepoxide and ethanol all produced mild ataxia as assessed by visual monitoring and a reduction in motor activity as determined by a piezo-electric transducer mounted on the underside of the suspended floor of the rat plexiglass chamber (mean pentobarbital decrease in Vrms=69±8% (n=6), mean chlordiazepoxide decrease in Vrms=75±9% (n=6), mean ethanol decrease in Vrms=61±9% (n=6); no significant differences between drugs at $P>0.05$; pre-ethanol Vrms= 0.3±0.06 V (n=6)). Heroin was given at a rewarding dose and methamphetamine was given at a dose that increased motor activity (mean increase in Vrms=78±7% (n=6)).

Figure 32A:
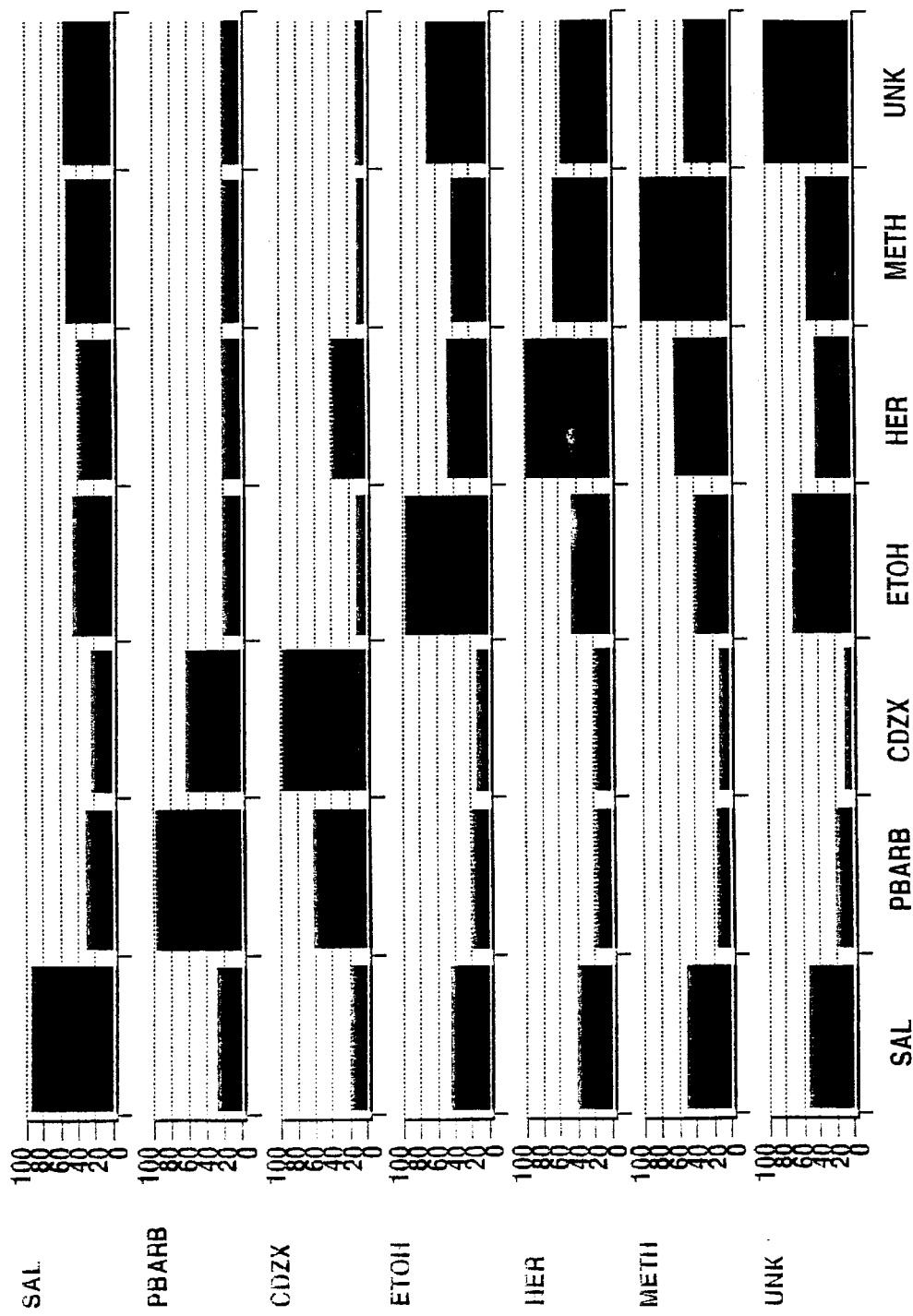
FIG. 32A is one presently preferred embodiment of an experimentally derived EEG similarity matrix comparing saline, pentobarbital, chlordiazepoxide, ethanol, heroin, methamphetamine, and the unknown drug against each other in accordance with the present invention.

Referring now to FIG. 32A, similarity matrices were then constructed based on drug discrimination accuracies corresponding to pre-drug A versus pre-drug B, post-drug A versus post-drug B and post/pre-drug A versus post/pre-drug B conditions. FIG. 32A illustrates a cumulated similarity matrix (average of the six rats) for the post-drug A versus post-drug B condition. Clear discriminations are evident in the similarity matrix. For example, pentobarbital is most like chlordiazepoxide and least like heroin. Heroin is moderately similar to methamphetamine. Of the drugs tested, ethanol is the most like saline. However, it is only 42% similar. Ethanol is clearly most like the unknown drug. After the production of these result, it was discovered that the unknown drug was indeed ethanol.

Figure 32B:
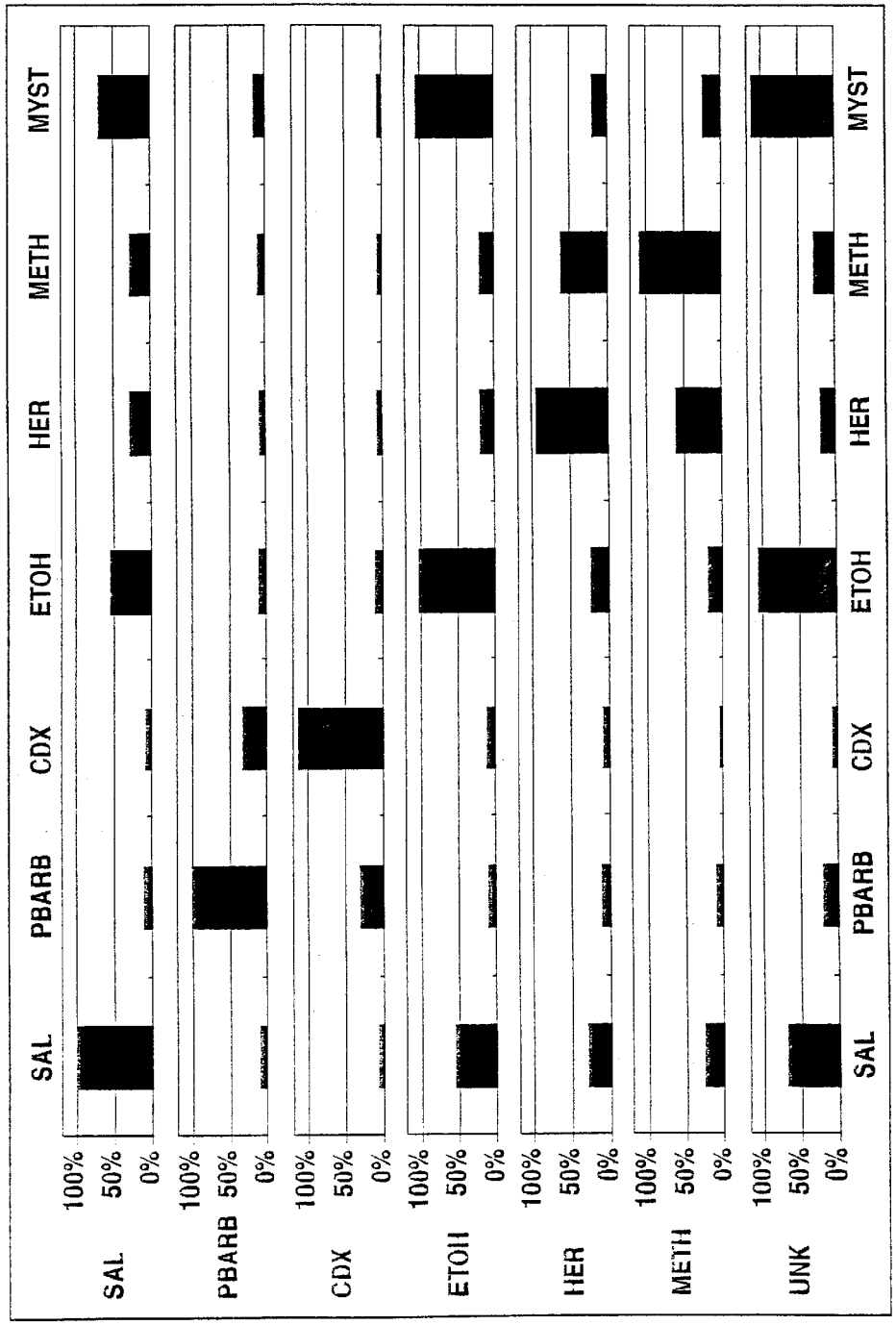
FIG. 32B is an alternative embodiment of an experimentally derived EEG similarity matrix comparing saline, pentobarbital, chlordiazepoxide, ethanol, heroin, methamphetamine, and the unknown drug against each other in accordance with the present invention.

FIG. 32B is a similarity matrix containing data collected from one rat rather that than an average of five rats as is presented in FIG. 32A. The greater accuracy of FIG. 32B is a result of a more rigorous pre-processing of the raw EEG inputs signals.

Figure 33:
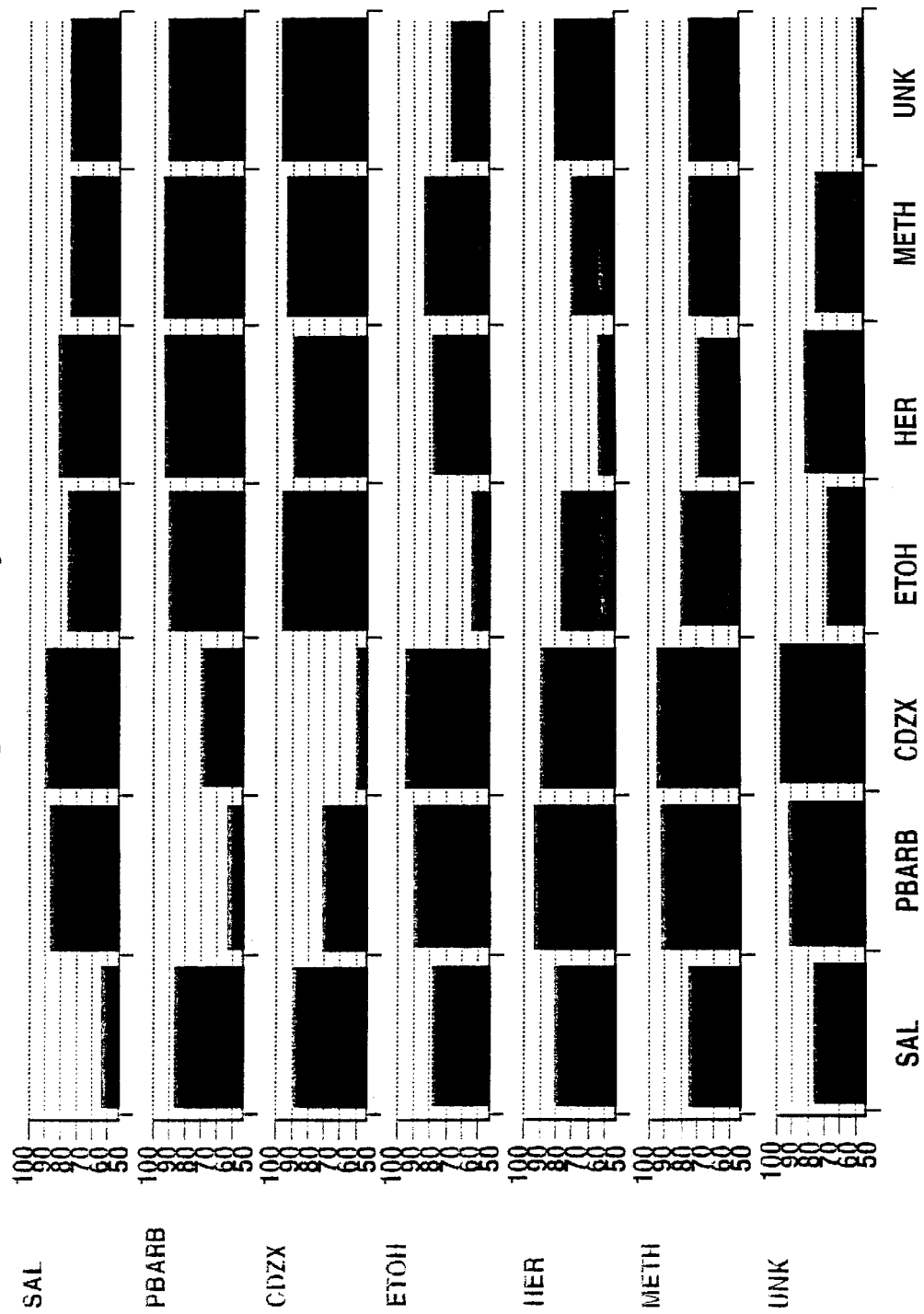
FIG. 33 is one presently preferred embodiment of an experimentally derived EEG discrimination accuracy matrix comparing saline, pentobarbital, chlordiazepoxide, ethanol, heroin, methamphetamine, and the unknown drug against each other in accordance with the present invention.

Referring now to FIG. 33, drug discrimination accuracy was determined for each of the drugs administered. The discrimination matrix provides a measure of the ease of discriminating between arbitrary drug A and arbitrary drug B. Classification accuracy was determined by the formula $A=(1-S)/2$, where A is the classification accuracy and S is the similarity. The accuracy is high when the similarity is low, hence it is easy to distinguish drug A from drug B. When the accuracy is 0.5 (50%), it is difficult to distinguish between drug A and drug B.

FIG. 33 further illustrates the classification accuracies for post-drug A versus post-drug B. Note that each drug is difficult to distinguish from itself (i. e., classification accuracy is about 50%) as reflected in the diagonal portion of the graph. Some drugs are easily distinguished from each other. For example, the effects of ethanol on electrocortical activity can be accurately discriminated from the effects of chlordiazepoxide and pentobarbital, even though their behavioral effects (i.e., ataxia) are similar.

Figure 34:
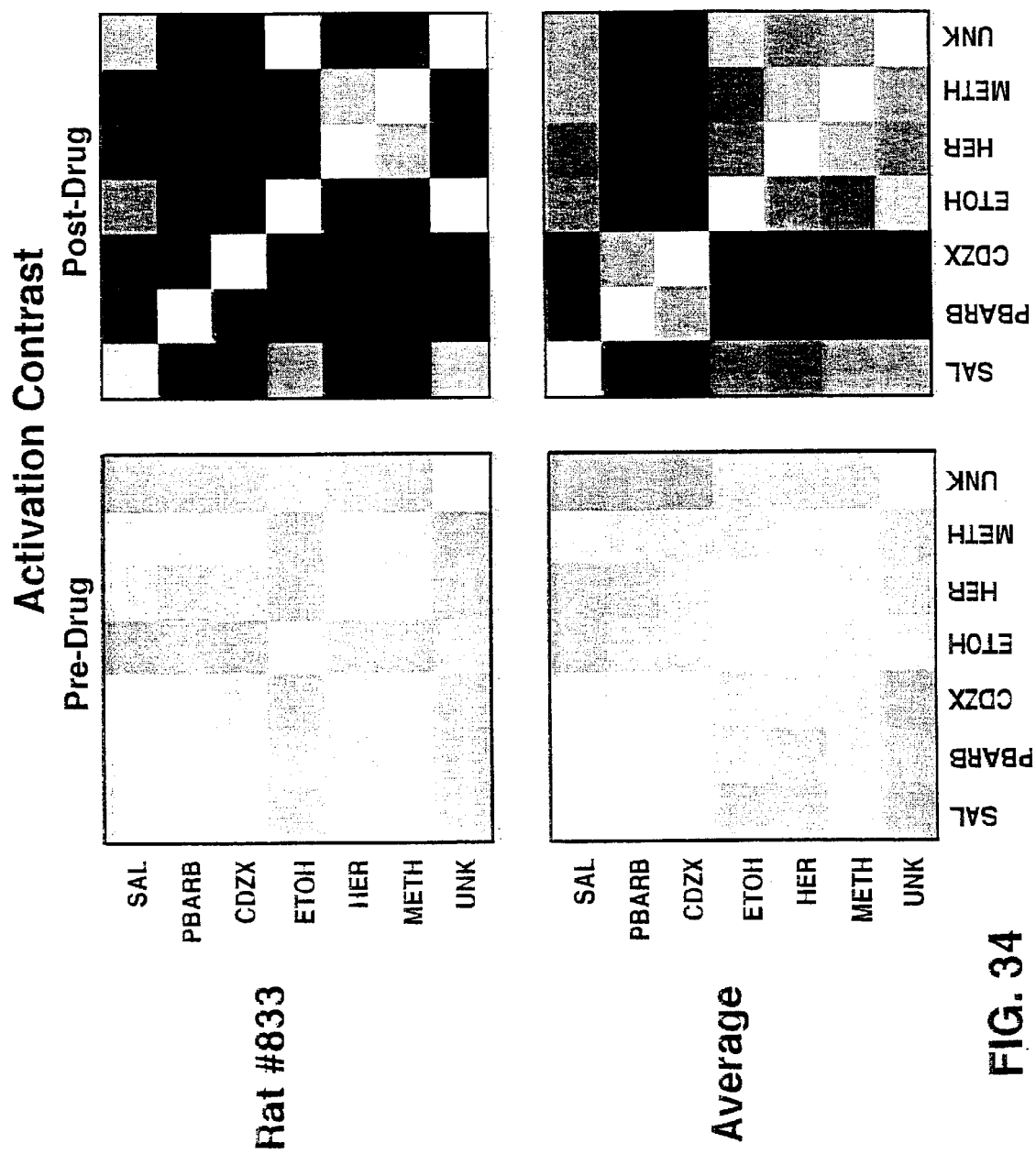
FIG. 34 is one presently preferred embodiment of a collection of experimentally derived EEG activation contrast plots comparing pre and post drug average activation values comparing saline, pentobarbital, chlordiazepoxide, ethanol, heroin, methamphetamine, and the unknown drug against each other in accordance with the present invention.

Referring now to FIG. 34, for ease of comparison across pre-drug, post-drug and post/pre-drug conditions, the similarity matrices were normalized to linearized grayscale images. These images allowed for easy visual inspection of differences between conditions, and demonstrate the contrast between pre-drug and post-drug EEG activations for each of the conditions.

In conclusion, ERI analysis was able to detect, with varying degrees of accuracy, and within a time resolution of five to ten seconds, the activation of electrocortical activity by all drugs tested. In addition, ERI was able to discriminate ethanol effects from chlordiazepoxide and pentobarbital, despite the fact that all three drugs produced similar behavioral effects characterized by ataxia and reduced motor activity. Finally, the utility of ERI was validated by the successful determination of a blind drug as ethanol based on the dissimilarity matrix.

These findings indicate that ERI is useful in the detection and discrimination of the central nervous system (CNS) activating effects of select psychoactive substances. In this study, only one channel of EEG activity was measured. It stands to reason that discrimination accuracies of different psychoactive drugs will be improved even further by multiple channel recordings, the addition of single-trial evoked potential analysis and by correlation with other physiological and behavioral indices such as measurements of core body temperature, blood pressure, motor activity, electrocardiographic activity and electromyelographic activity.

The ERI at the present invention therefore is particularly useful tool for determinations regarding the time course of brain activation by various investigational substances. The ability to reliably and accurately discriminate the brain electrocortical activating effects of various investigational substances is a useful tool for the categorization of drugs into a particular class of psychoactive drugs. This objective should be obtainable might obtain following the development of a library of known responses to the fiduciary compounds within a pharmaceutical class.

EXAMPLE II

Figure 35:
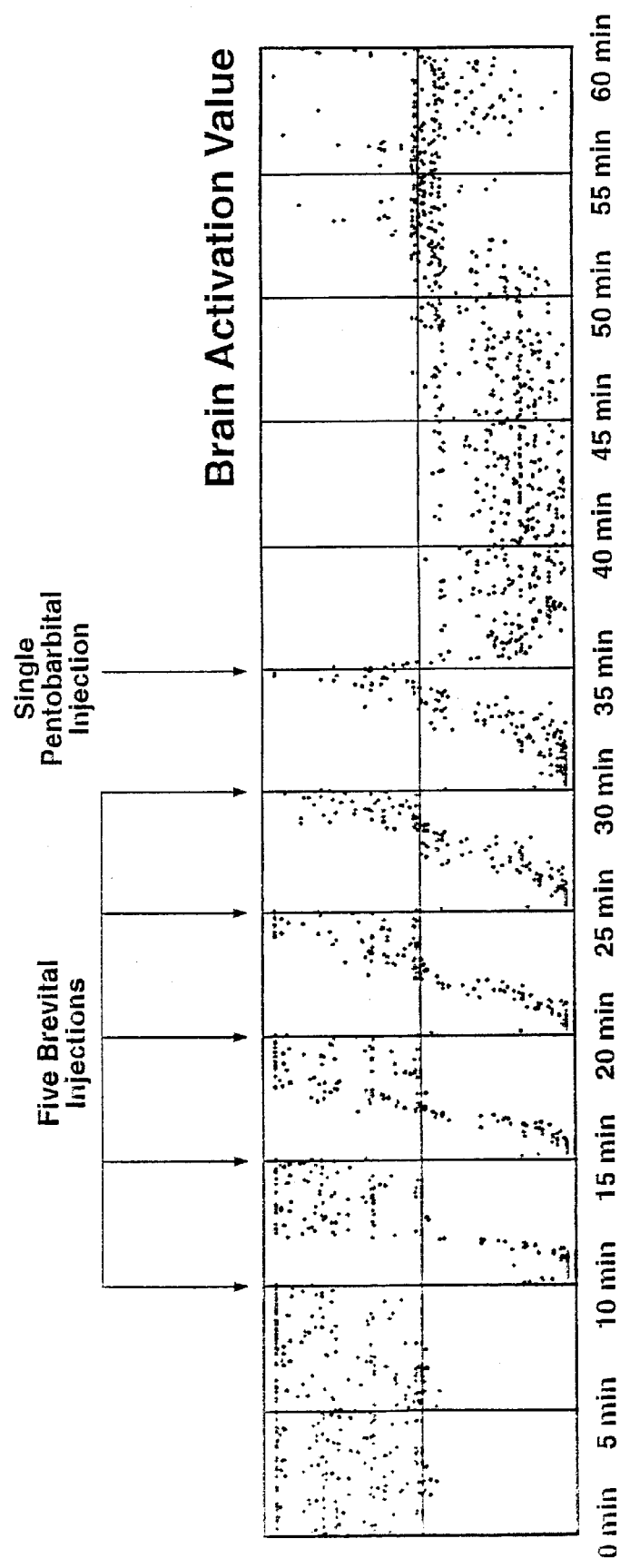
FIG. 35 is one presently preferred embodiment of an experimentally derived EEG activation value plot illustrating five brevital injection and a single pentobarbital injection in accordance with the present invention.

Referring now to FIG. 35, the brain activation value plot comes from data collected during a one hour EEG study on a freely behaving rat. Fast acting Brevital (3 mg/kg, 150 uL) was administered intravenously at 10, 15, 20, 25 and 30 minutes. Pentobarbital (10 mg/kg, 0.1 mL) was given intravenously at 35 minutes. A single EEG electrode in the rat brain was sampled at 10 KHz. Each data point in the above brain activation value plot represents one second of highly processed EEG. The method of processing the EEG was derived from a pattern learning algorithm that trained on EEG data taking just before and just after the Brevital injection at 30 minutes. The EEG training data was taken from 100 seconds recorded from 28:10 until 29:50 and 180 seconds recorded from 30:10 until 33:10. Each data point represents the degree of presence of a learned combination of phase-encoded frequencies between 1,000 and 3,000 Hertz.

As shown in the above brain activation value plot, fast acting Brevital can be seen moving in and out of the brain. It enters the brain very rapidly at each injection and then exits. Notice that Brevital leaves the brain a little more slowly after each subsequent injection. The single Pentobarbital injection enters the brain more slowly than the Brevital injections and stays in the brain for a much longer duration. This brain activation value plot reveals the temporal dynamics of two barbituates as they cross the blood-brain barrier and modify brain activity as revealed by spontaneous EEG.

EXAMPLE III

Figure 36:
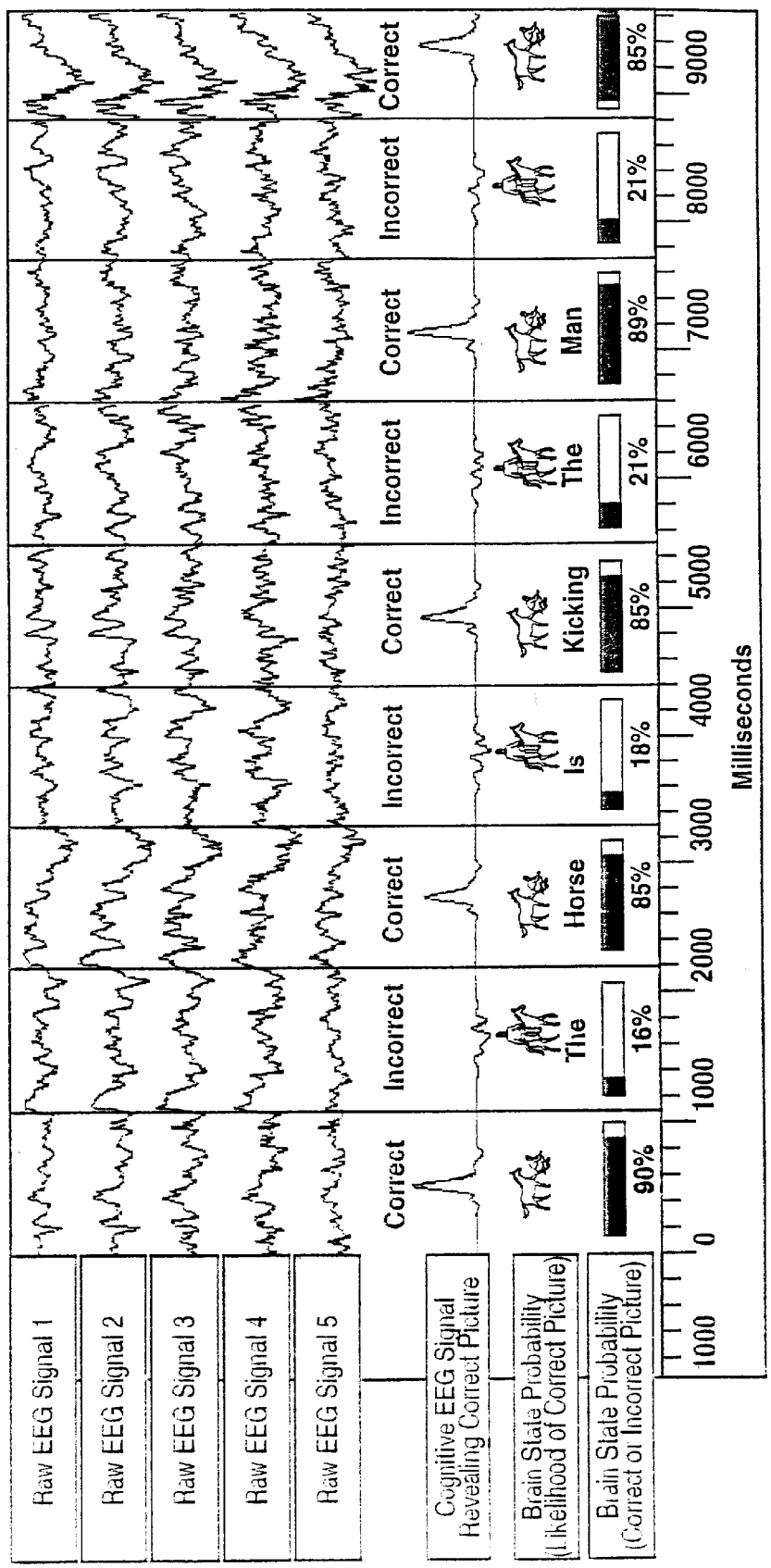
FIG. 36 is one presently preferred embodiment of a collection of experimentally derived EEG data including raw data, expanded data, and probability of a correct classification in accordance with the present invention.

Referring now to FIG. 36, a "cognitive comprehension" study was conducted on a human subject who viewed a computer screen displaying a written sentence describing a situation in a picture scene such as "The horse is kicking the man." The subject first read the sentence and viewed a correct picture (such as the picture of the horse kicking the man) and also some incorrect pictures (such as the picture of the man sitting on the horse). The pictures were then presented sequentially (one at a time) on the screen while five channels of raw EEG data were recorded from the subject's scalp.

Nine 1,100 ms epochs (columns) of raw EEG signal data are shown in FIG. 36. Note that it is difficult to visually discern discriminant patterns in the five raw EEG signal channels.

The cognitive EEG signal channel is a highly processed combination of EEG data from the five raw EEG signal channels and five epochs. A particular weighting pattern has been learned (discovered) and applied to a collection of amplitude, phases, locations, frequencies and latencies to generate the cognitive EEG signal. Note how this cognitive EEG signal robustly reveals the presence of a correct picture on the display screen. The fact that the cognitive EEG signal exhibits striking differences between correct and incorrect pictures is an indication that the subject comprehends and understands the meaning of the particular English sentence.

The ability to accurately monitor cognitive functions such as comprehension, memory and awareness from EEG analysis opens new doors of opportunity in psychiatric drug evaluation and development. This increased sensitivity in the monitoring of neurocognitive circuits will increase the efficacy of neurological drug development in pre-clinical and in early clinical trials. In addition, an increased ability to measure cognitive ability from EEG or the like may improve our understanding of neurological disorders such as Alzheimer's disease and other forms of dementia.

Additionally, cognitive monitoring may provide a useful method for studying coma patients. Other embodiments in accordance with the present invention may even provide a method for communicating with patients who are in a coma, but are still able to hear.

EXAMPLE IV

Figure 37:
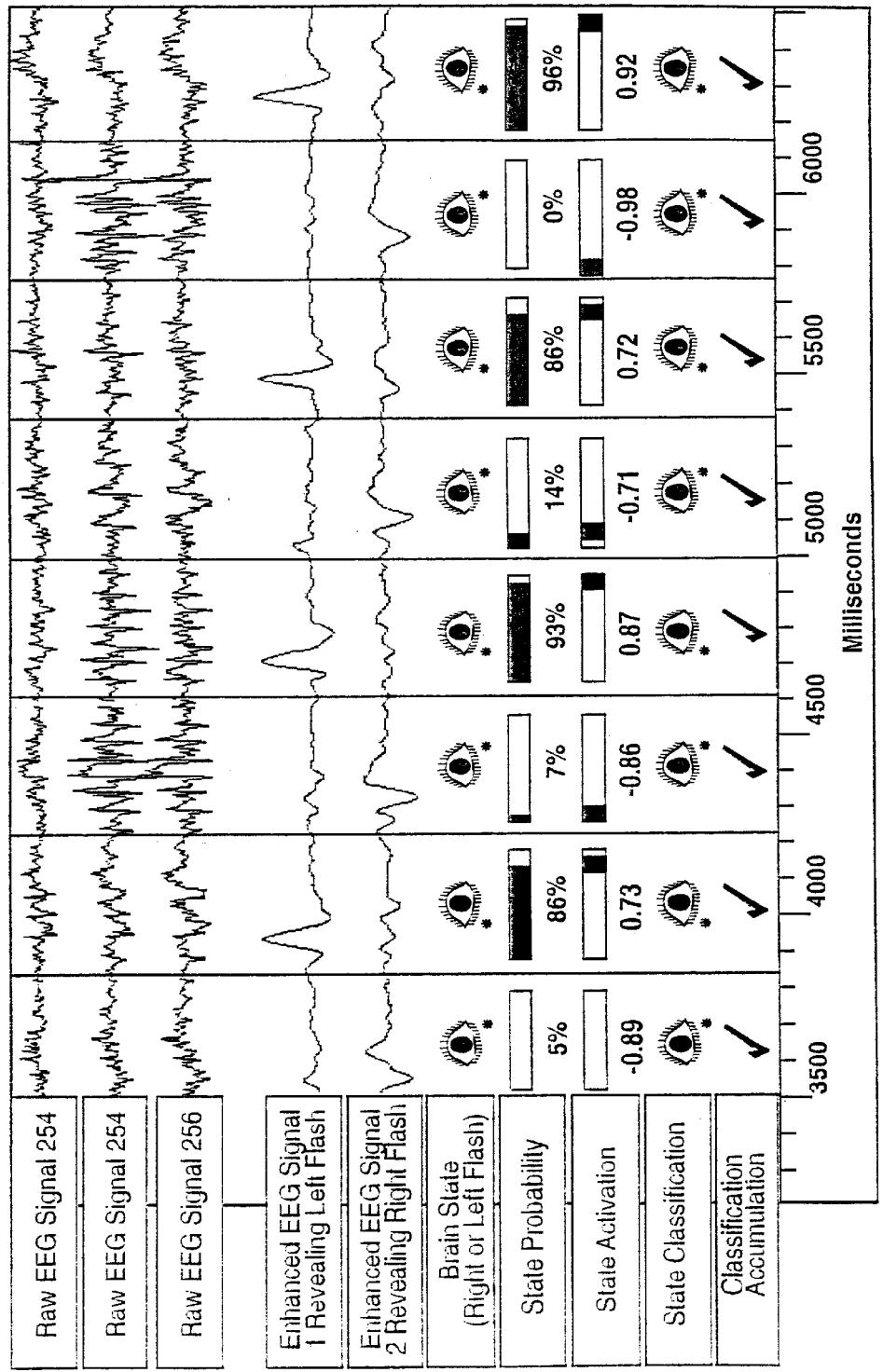
FIG. 37 is another presently preferred embodiment of a collection of experimentally derived EEG data including raw data, expanded data, and probability of a correct classification in accordance with the present invention.

Referring now to FIG. 37, notice that the three raw EEG signals (254, 255 and 256) do not reveal the presence or location of a light flash. Rather, the tiny light flash signal is obscured in background brain activity noise. This noise stems from other neuronal processing unrelated to the signal of interest. The signal of interest is exclusively correlated with the presence and location (right or left) of a brief visual flash stimulus.

Notice that the enhanced EEG signal 1 readily reveals the presence or absence of a visual checkerboard flash stimulus in the lower left quadrant of the subject's visual field. The subject's eyes were fixated on a point in the center of a computer monitor while 30 millisecond checkerboard flashes were presented at random times and locations in the four quadrants of the screen. In this study, mathematical representations of visual-flash brain-location maps were automatically generated and used to determine with 99% accuracy the difference between a left and a right checkerboard flash in the subject's field of vision. Note that the enhanced EEG signal 2 reveals the presence of a visual checkerboard flash to the lower right side of the subject's visual field. The state probability channel indicates the probability of a flash on the lower left side of the screen.

The attainment of a 99% accuracy in single trial (single EEG segment) brain state classification demonstrates the technological capability for revealing hidden signals of interest from a sea of background brain activity noise. Many evoked and event related potential studies are currently under way in animal toxicology, CNS pharmacology and in human clinical trials. It is no longer necessary to rely on the limited and inconclusive methods of traditional EP, ERI and EEG analysis. This new EEG and EKG signal enhancement technology of the present invention can now be used to robustly reveal the subtle effects of drugs on the brain, heart and other organs of the body. Significant new information concerning drug presence, dose response, delivery, pharmacology, metabolism, toxicology and side effects are now be available consistent with the novel apparatus and methods discussed herein.

EXAMPLE V

Figure 38:
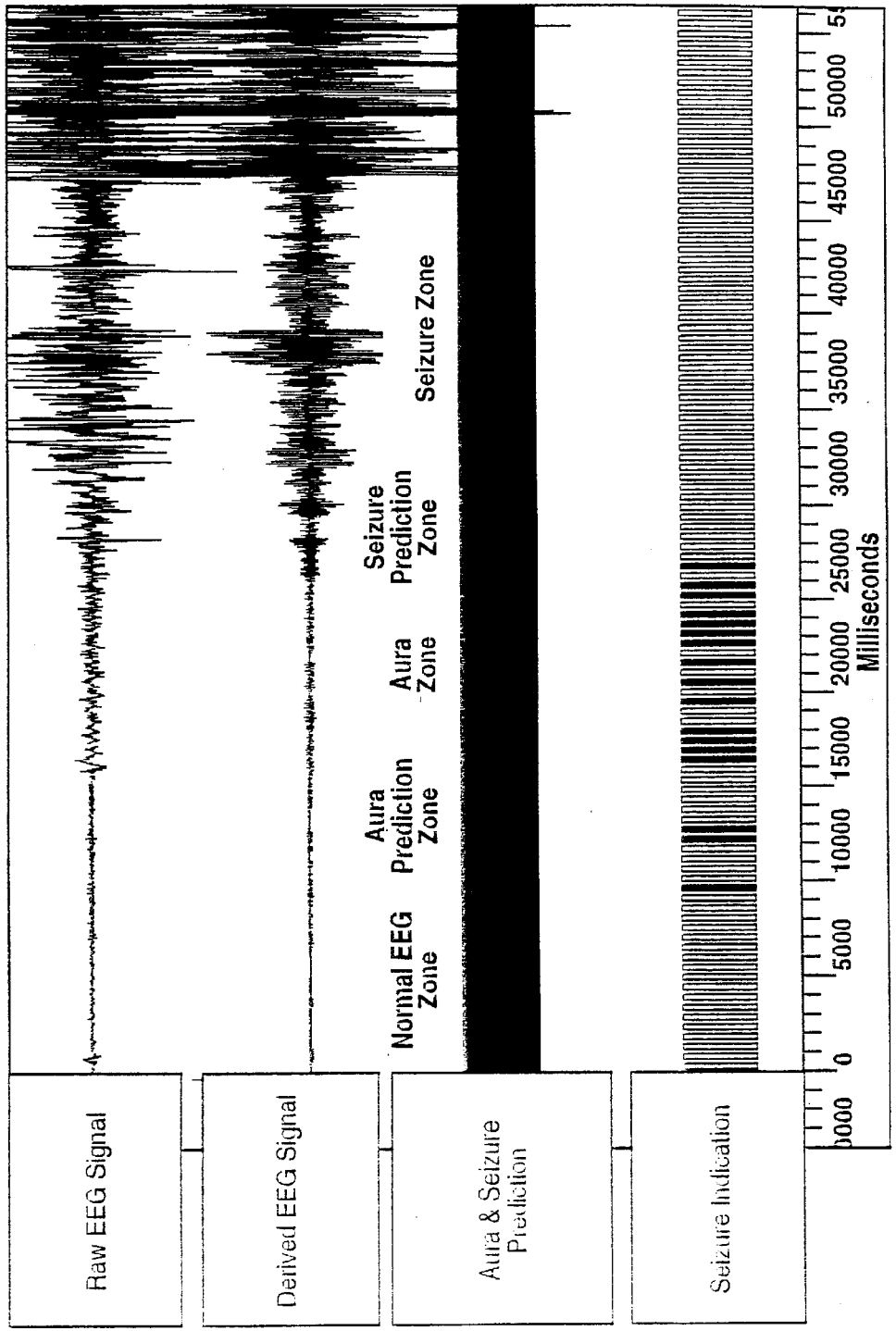
FIG. 38 is one presently preferred embodiment of a collection of experimentally derived EEG data illustrating a seizure predication in accordance with the present invention.

Referring now to FIG. 38, an epilepsy study was conducted where raw EEG was analyzed and recorded continuously from a patient before, during and after the occurrence of a major seizure. The raw EEG signal corresponds to a single extracranial EEG channel. A difficult seizure prediction problem is the automatic calibration of threshold values, for each patient, that are robustly repeatable from seizure to seizure. EEG signals have been studied for years in many laboratories in an attempt to predict and diagnose the onset of migraine headaches, auras and seizures. However, it has been difficult with standard analysis procedures to predict event onset times with high accuracy due to the inherent noise and complexity of the EEG signals.

Hardware and software technology, in accordance with the present invention has generated aura and seizure models and these models have been used to produce an automatic prediction capability. The aura and seizure prediction channel (the dark horizontal bar just below the Derived EEG Signal) provides an indication of the location of five brain activity zones: Normal EEG Zone, Aura Prediction Zone, Aura Zone, Seizure Prediction Zone and Seizure Zone. Note that the Aura Prediction Zone precedes (and predicts the onset of) the Aura Zone.

Additionally, the seizure indication channel (the horizontal bar at the bottom of the display screen) clearly delineates the Aura Prediction Zone and the Aura Zone. The occurrence of these two zones immediately precedes the seizure prediction zone which in turn precedes the actual seizure zone. The existence of this sequence of brain activity zones provides significant opportunity to accurately predict the onset of seizures prior to their occurrence.

The ability to predict and diagnose migraines, auras and seizures in individual patients and in patient populations will provide a powerful tool for the development of pharmacological agents designed to treat migraine headaches and reduce the frequency and severity of seizures. For example, the ability to predict migraines and seizures may be closely linked with the ability to detect the influence of a drug on the pattern of EEG activity present during such a migraine or seizure. Such EEG drug pattern discovery and tracking technology may further lead to increasingly effective.

EXAMPLE VI

The subject for this study was a single 32 year old right-handed male. He was instructed to lie quietly on a bed in a magnetically isolated room. Four hundred (400) pulses of air of 30 milliseconds duration were delivered to the subject's right thumb through a plastic tube connected to a pneumatic air pump. The pulses were delivered at a rate of about one per second. The inter-stimulus interval was randomized about a one-second mean in order to avoid the production of standing waves in the brain due to perfect periodicity.

MEG data was collected using a Biomagnetic Technologies Incorporated (BTI) 37-channel helium bathed magnetogradiometer. This machine uses Super Conducting Quantum Interference Devices (SQUIDS) to measure ultra-weak (femtotesla) magnetic fields from the brain. The measurement coils were positioned approximately two centimeters above the subject's head over the left somatosensory cortex, aligned to sense spatial gradients in the radial component of the extracranial neuromagnetic wavefield normal to the scalp surface.

The 37 channels were each sampled at 297.6 Hertz, and recorded from 150 milliseconds pre-stimulus to 850 milliseconds post-stimulus for each of the 400 air pulses. This resulted in 400 raw MEG data epochs. Each of these 400 raw epochs was divided into two sub-epochs of 484 milliseconds each. In order to facilitate the Fourier Transforms portion of the analysis, 16 milliseconds were deleted from each raw epoch so that the sub epochs would each have exactly 144 frames.

The air pulse stimulus was 150 ms into the first sub-epoch. The second sub-epoch was used as a control, consisting of neural noise defined as brain activity unrelated to the study event of interest. No epochs were removed due to the presence of artifacts such as dye blinks, facial EMG, etc. Therefore, 400 "touched" and 400 "non-touched" epochs were presented for analysis.

The strategy of the new algorithm is to apply several different methods of analysis to each type of epoch to find subtle but consistent inherent differences between epoch types, and similarities within the same epoch type. By using an integrated system of different methods it is hoped that the inherent limitations of any single technique can be avoided. The software then analyzes all factors and identifies the set of characteristics which best differentiates and identifies the epoch types (learning process). These characteristics are then mathematically encoded as an "interpretation map", which is used subsequently to analyze waveforms which the software has not previously "seen" (classification process).

The researcher defines the length and other parameters of each epoch type and labels them. In this study two epoch types were present, but any number could be used depending on the study design. The epoch length and other settings are determined by experience or trial and error. The software is fast enough that multiple trials can be run on the same waveform data using different parameters in a short amount of time to see which trial obtains the best results. The 400 epochs of each type (touched and non-touched) were divided into two groups of 300 learning and 100 testing epochs.

Epochs set aside for learning (a total of 600 in this study) are first preprocessed by the software to remove unwanted artifacts, dc (zero frequency) amplifier drifts, and to emphasize latency regions of interest. Each epoch is then decomposed into features in an extended phase space representing spatial, time, frequency, phase, and inter-channel relationships. These features are then analyzed in detail for characteristics common to the epoch type. This analysis includes evaluation of coherence between signals distributed in complex fashion across all four domains of space, time, frequency, and phase.

The program next performs a set of analyses to find features that are most reliably different between epoch types, called state separation analysis. This consists of waveform analysis, distribution function analysis, fuzzy logic analysis, and discriminant optimization. Finally, the results of the above analyses are used to generate a set of parameters, components, functions, and criteria, which best identify epoch type and discriminate between epochs. This is recorded as an interpretation map for subsequent use in evaluating "unknown" data.

Figure 39:
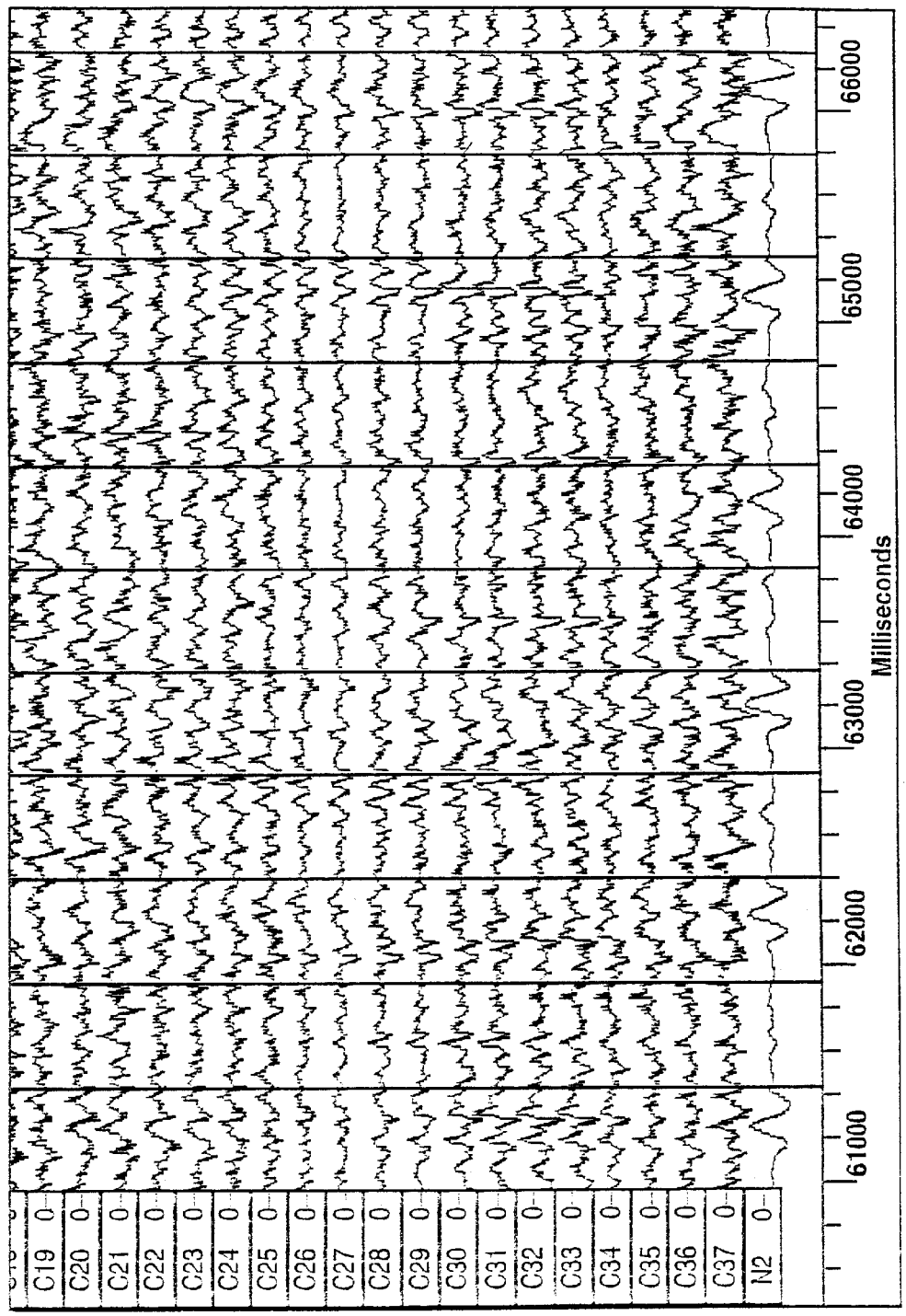
FIG. 39 is one presently preferred embodiment of a collection of experimentally derived EEG data including raw data and a robust Single Trial Evoked Response Signal (STERS) in accordance with the present invention.

Referring now to FIG. 39, the 200 testing epochs (100 each of touched and non-touched) were then processed by the software for classification into one of the two epoch types. The data is first pre-processed in the same way as in learning mode. The program then uses the interpretation map to apply the set of analyses and criteria it previously determined was optimal to the "unknown" epoch's classification. The software analyzes each epoch as an individual event (no averaging) and presents it as a composite, "clean" waveform made up of those characteristics used in its analysis and classification. This resultant waveform is called a Single Trial Event Related Signal (STERS). The method of producing STERS is called Single Trial Event Resolution (STER). The software also provides a statistical summary of results, including the confidence level that each epoch was classified correctly, as well as calculations of sensitivity, specificity, overall accuracy, and significance level.

Analysis of the raw data resulted in twenty different STERS "channels", each with characteristic event-related waveform signals differing in shape, amplitude, and latency from each other. As this study was primarily performed to assess the validity and accuracy of the new algorithm, we selected the most robust signal for statistical analysis.

FIG. 39 is a display of several raw MEG channels (channels 18 through 37 are visible in this Figure), and the most robust of the derived Single Trial Evoked Response Signal (STERS) channels produced by the analysis. The raw MEG epochs, of 484 ms duration, have been multiplexed by event type, producing the alternating touched and non-touched epochs shown here. The STERS waveform at the bottom of the screen reveals the thumb-touch signal that was previously hidden in the complex 37-channel MEG data.

Of the 200 epochs evaluated in interpret mode (100 touched and 100 non-touched), the algorithm correctly classified 181 for an overall accuracy of 90.5%. It correctly labeled 91 of 100 touched and 90 of 100 non-touched epochs. It incorrectly labeled 10 non-touched epochs as touched, and 9 touched epochs as non-touched.

Figure 40:
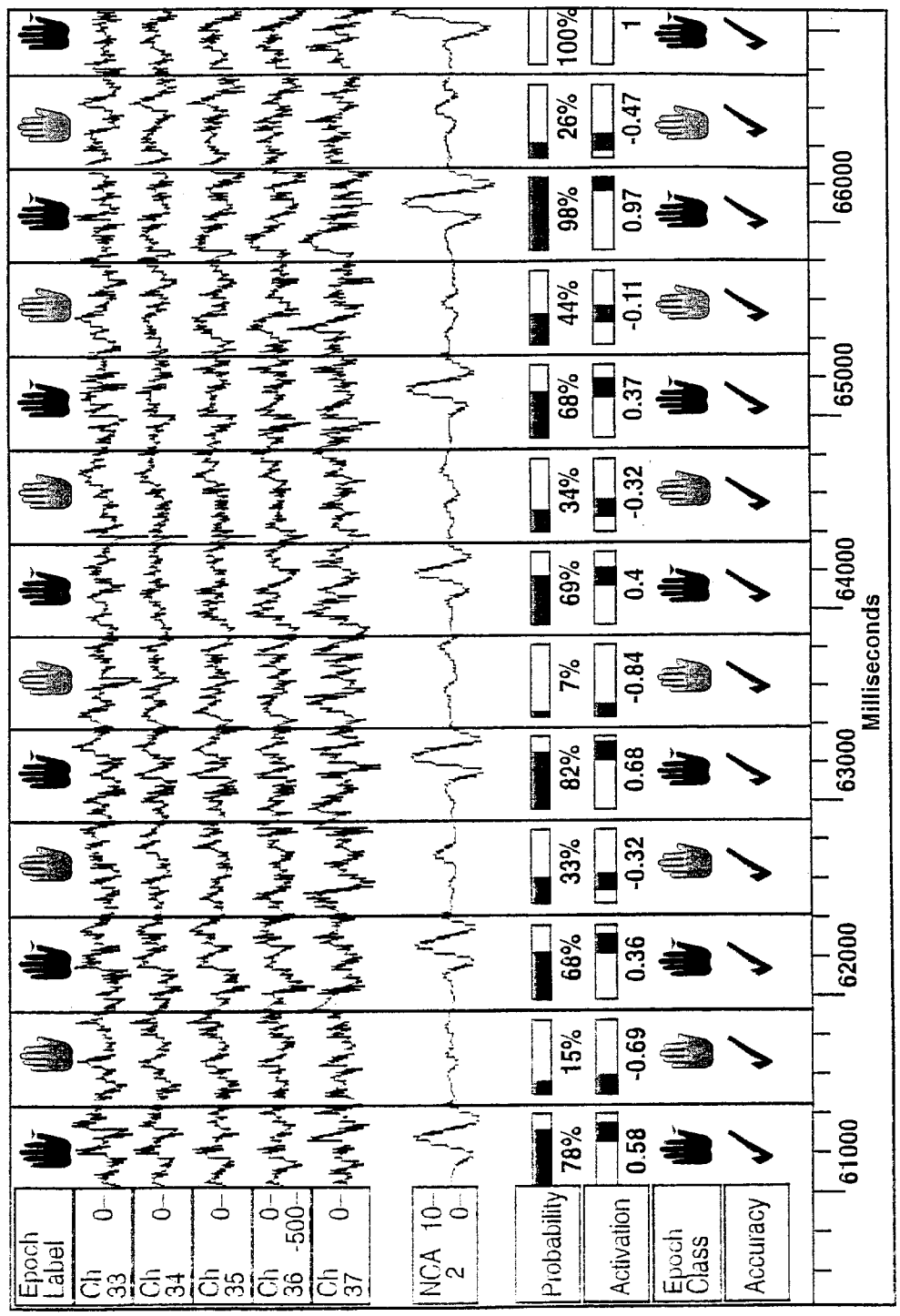
FIG. 40 is another presently preferred embodiment of a collection of experimentally derived EEG data including raw data, expanded data, and probability of a correct classification in accordance with the present invention.

Referring now to FIG. 40, visual results taken from the computer monitor are shown. The visual differences between the "computer enhanced" STERS waveform in the center of the display and the raw waveforms (channels 33–37) above are pronounced. It can also be seen that even though the STERS waveforms are generally robust where the thumb touch occurred, there exist differences from epoch to epoch in amplitude, shape, and latency. The non-touched epochs are generally flatter, with lower amplitudes, and exhibit greater variety in shape than the touched epochs. These variations are probably due to differences in "background" brain activity noise from epoch to epoch. In spite of this variation, the thumb touches are well differentiated from background noise.

Figure 41:
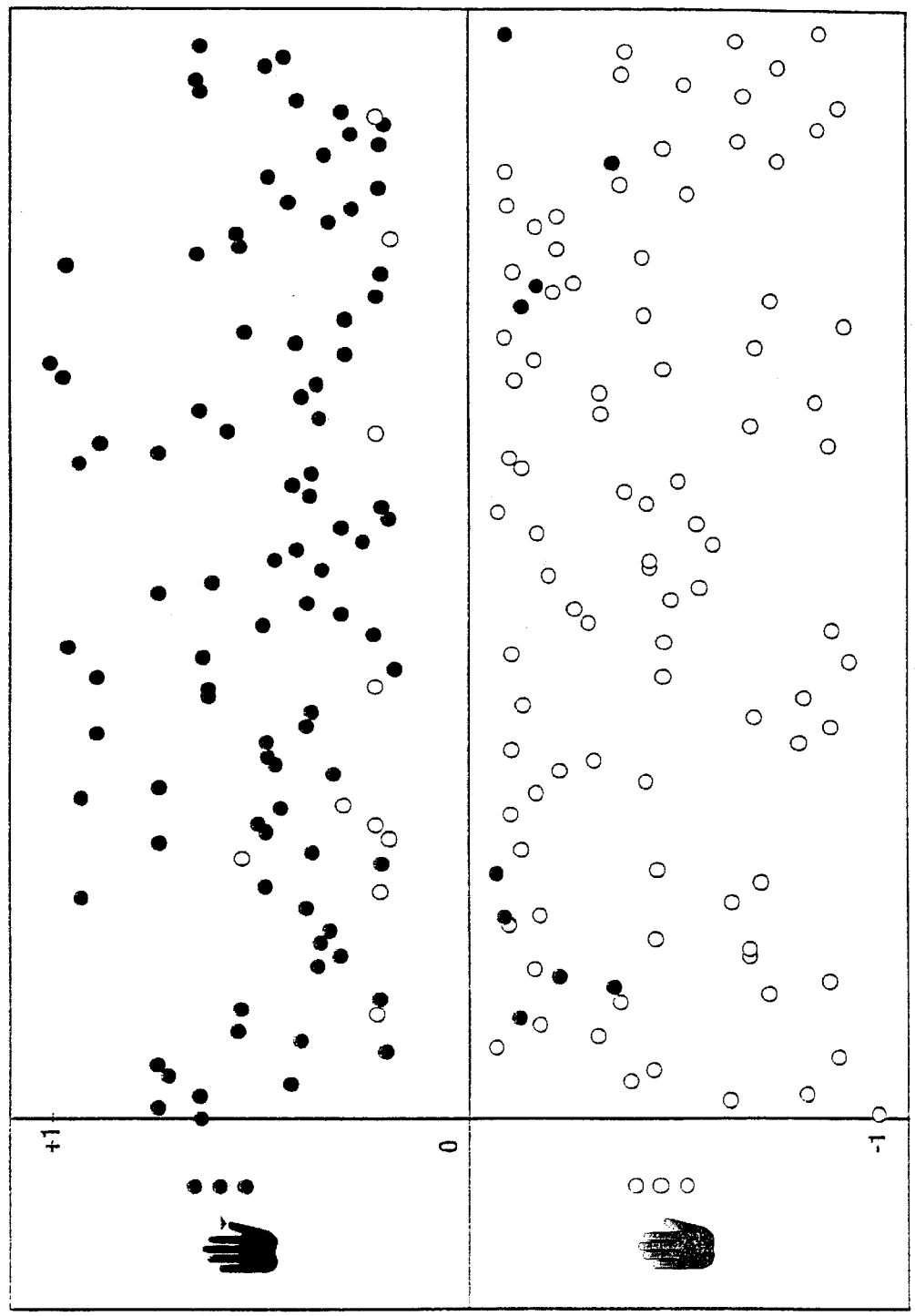
FIG. 41 is one presently preferred embodiment of an experimentally derived EEG activation value plot comparing the epoch values for touched and untouched states in accordance with the present invention.

FIG. 40 illustrates thirteen columns of data from the study. Each 484 ms epoch (column) contains either a touched or a non-touched event-type. The epochs alternate by event-type, beginning with touched epochs. The epoch label at the top indicates which type the epoch "truly" was. The epoch classification channel gives the type of epoch assigned by the program to the epoch. The Probability channel assigns a computer-calculated probability that the epoch contained a "touch". The Activation channel gives the degree to which the epoch met the criteria for its classification, from +1 for touched, to −1 for non-touched epochs. The Accuracy channel places a check mark if the label matches the true epoch type, an "X" if it doesn't. Notice that although the STERS touched waveforms are generally robust, they do reveal significant differences in amplitude, shape, and latency between distinct touched epochs FIG. 41 is a plot of the activation values derived in the study. The activation value represents the degree to which each condition is considered by the program to be present in the testing epoch (column).

FIG. 41 is a plot of the values of the Activation channel of FIG. 40, showing how each of the 200 epochs were classified. The black dots represent the 100 true touched epochs, and the white dots correspond to the 100 true non-touched epochs. The black dots that lie above the horizontal line are those correctly classified as touched epochs, and those that lie underneath the line are incorrectly classified as non-touched epochs. The white dots above the line were incorrectly classified as touched, below the line correctly as non-touched. The further from the line, the greater the degree to which the epoch matched its classification. Note that even though there is some overlap, the categories separate quite cleanly.

Figure 42:
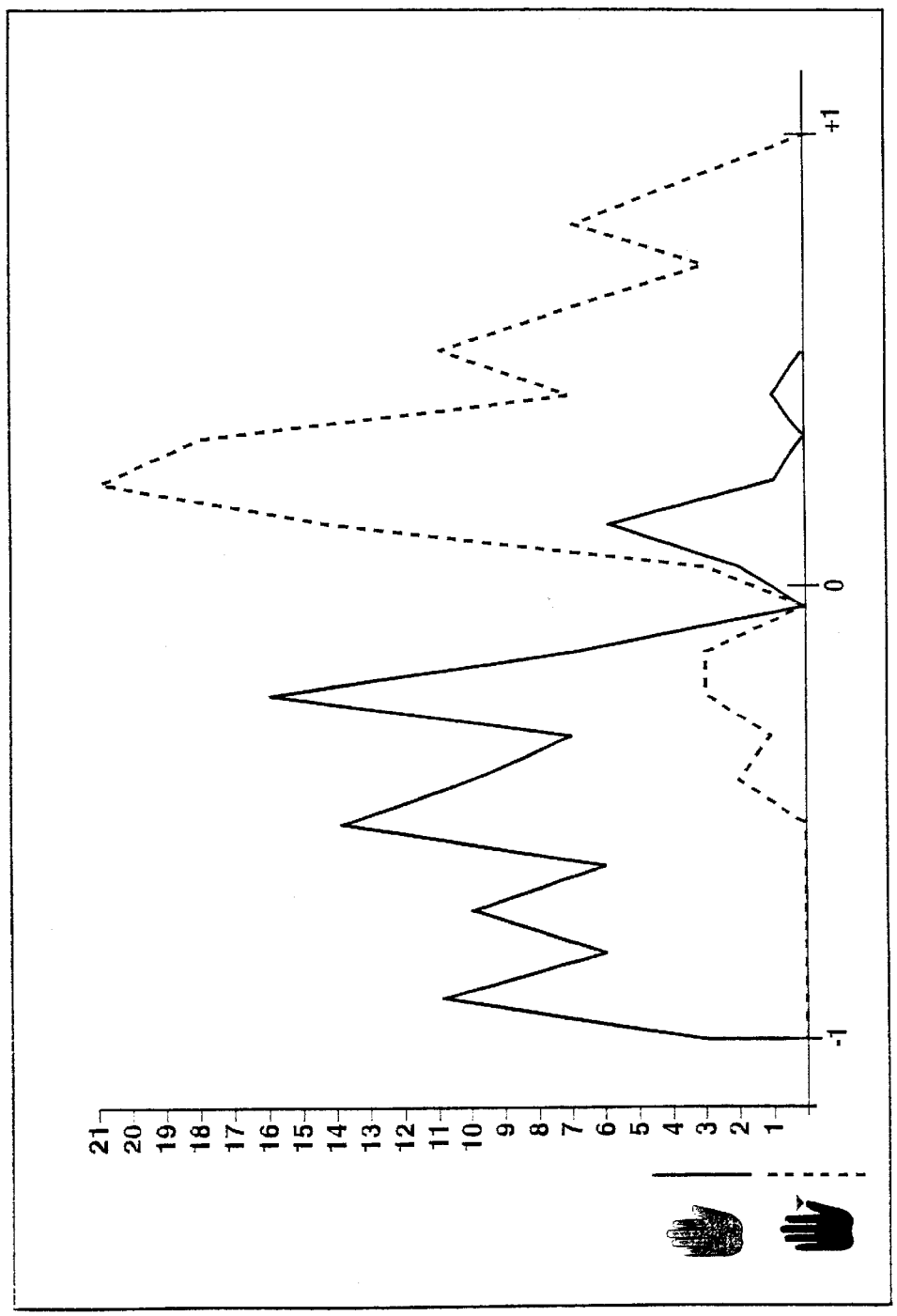
FIG. 42 is one presently preferred embodiment of a histographic representation of experimentally derived EEG activation values for touched and untouched states in accordance with the present invention.

FIG. 42 is a histogram showing the same data graphically. The black line represents the true touched epochs, and the gray line corresponds to the true non-touched epochs. Notice that most of the epochs were correctly separated into their true event-types, as indicated by the areas under the curves. Also note the relatively sharp demarcation between the "touched" and "non-touched" areas.

Figure 43:
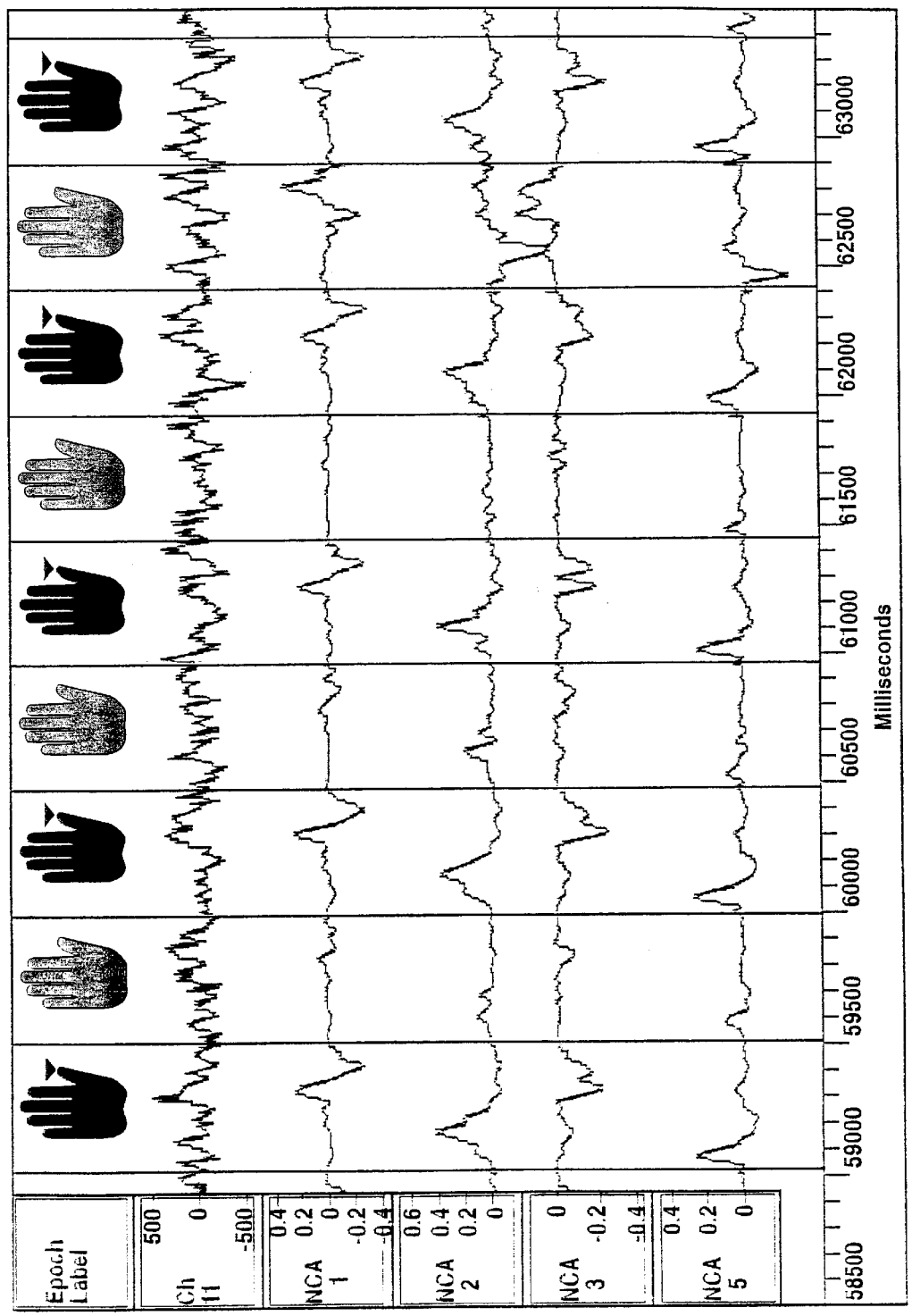
FIG. 43 is one presently preferred embodiment of a collection of experimentally derived EEG data including epoch label, raw data, and four Single Trial Evoked Response Signals (STERS) in accordance with the present invention.

Referring now to FIG. 43, separate analysis of the same data was performed using only the channel 11 waveform, selected randomly to assess the results using only a single channel. This evaluation was interesting because even from a single channel the program was able to derive four distinct STERS waves, each possessing different shape and latency with respect to the onset of the air-pulse stimulus.

FIG. 43 illustrate results of the channel 11 analysis displaying true epoch labels, raw MEG data, and four STERS channels (labeled NCA on the chart) corresponding to touched and non-touched event types. Each column represents one 484 ms epoch of data. The top row contains Epoch-Label icons indicating the true event type for each epoch. The second row contains one channel (channel 11) of raw MEG data. Note that the displayed epochs (columns) have been multiplexed by event-type beginning with the touched event type. Thus, the first, third, fifth, seventh, and ninth epochs (columns) contain touched events (air-pulse stimulus present at 150 ms latency into the epoch), whereas the second, fourth, sixth, and eighth columns (epochs) contain non-touched events (no stimulus present).

The third through sixth rows (STERS channels 1 through 4) contain single-event related waveform signals. The STERS waveform signals for each epoch (column) were derived or generated by the classification process from the raw MEG epoch data displayed in the second-to-top row (channel). Notice that the STERS (NCA) channels reveal robust single-event related waveform signals, which repeat for each of the touched event-type epochs. Each STERS channel reveals distinct waveform shapes, latencies, and other event-discriminating information.

The computer analysis of these MEG waveforms can be considered as a "test" of whether or not the subject's thumb was touched, similar to a clinical laboratory test of a disease state or condition. The use of the statistical concepts of sensitivity, specificity, predictive value, and accuracy, are therefore valid.

Sensitivity is defined as the percentage of times that the test is positive in epochs that are known to contain the specific event. Sensitivity is calculated by dividing the number of true-positive results by the total number of true-positive and false-negative results. Specificity is defined as the percentage of times that the test is negative in epochs which are known not to contain the event. Specificity is calculated by dividing the number of true-negative results by the total number of true-negative and false-positive results. The predictive value of a positive test is defined as the likelihood that an epoch for which the test is positive actually has the event. It is calculated by dividing the number of true-positive results by the total number of true-positive and false-positive results. The predictive value of a negative test is defined as the likelihood that an epoch for which the test is negative does not have the event. It is calculated by dividing the number of true-negative results by the total number of true-negative and false-negative results.

The sensitivity in this study (ability to correctly identify a puff of air touching the thumb) was 91%. Specificity (ability to correctly identify when a puff had not occurred) was 90%. The positive predictive value was 90%, and the negative predictive value 91%. The analysis correctly classified 181 of the 200 epochs for an accuracy rate of 90.5%.

The probability of correctly classifying 181 or more out of the 200 epochs is $1.24 \times 10^{-34}$. This indicates that the results are statistically significant, and that the classification algorithm is effective in discriminating between the two conditions. The analysis involving just a single channel obtained a classification accuracy of 80.5% and a p-value of $4.16 \times 10^{-19}$.

While not reported in detail in this study, the derivation of multiple (twenty) distinct STERS from the raw data suggests the method may be applied to "tracking" signal processing through different areas of the brain. We suspect much information remains to be discovered and analyzed in this data set.

It has been shown that STER analysis is accurate and valid for the detection of single-trial somatosensory events in MEG waveforms, specifically of a puff of air on the thumb. STER analysis is an accurate, valid strategy for the rapid analysis of single-trial MEG and EEG events. It appears to avoid the major weaknesses of prior analysis strategies and algorithms, while combining their strengths.

Data has been presented showing that STER analysis can be applied to visual evoked EEG potentials with equal or better sensitivity and accuracy than reported here for somatosensation. Future investigations should focus on characterizing and validating the STERS of other different event types and sources, including audition as well as somatosensation. Signals arising within the brain, stem, and cord such as motor activations, learning, attention, autonomic processes, etc. should also be investigated for the applicability of this new tool.

Detailed analysis of the different STERS waves generated from a single somatosensory event may produce new insights into signal processing by the brain. Our results suggest possible clinical applications and functional research avenues. More efficient CNS monitoring during surgery may be possible. Preliminary data has indicated that STER may be able to rapidly identify specific "intention to move" motor activations, a finding which carries possible implications for the treatment of paraplegics. Other avenues of research and potential applications will doubtless become apparent as this new tool is investigated further.

From the above discussion, it will be appreciated that the present invention provides an integrated waveform analysis method and apparatus capable of extracting useful information from highly complex and irregular waveforms such as EEG, EKG and MEG data. Unlike prior art devices, the present invention provides novel systems and methods for signal processing, pattern recognition and data interpretation by means of observing the affects of a particular state or event on an observed entity. The present invention also provides a method for improved drug modeling for evaluating the benefits of drugs and side-effect predication in relation to an observed entity (e.g., human or animal) and an improved method for drug fingerprinting.

Additionally, the present invention to provide novel systems and methods for measuring the effect of a particular event or state on the cognitive skills, motor ability, sensation, perception and the like of an observed entity (e.g., human or animal). Consistent with the foregoing, the present invention provides novel systems and methods for one or more of the following: (1) determining whether a drug successfully crosses the blood-brain barrier; (2) determining whether a drug alters brain function; (3) determining whether a drug modifies cardiovascular activity; (4) determining of dose-response relationships by analyzing the effect of a range of doses on EKG or EEG; (5) measuring drug-induced brain activity patterns indicating the presence of particular side effects inducing drowsiness, nausea, headaches, dizziness or cognitive impairment; (6) identifying the effect of a neurological drug on the electrical activity of the brain and heart in animal models and in human clinical trials; (7) improving the accuracy of drug evaluation with improved discrimination of physiological similarities and differences between distinct drug types; (8) lowering the cost of toxicology testing by more accurately revealing the effects of drugs on neurological and cardiovascular information processing systems in pre-clinical and in clinical trials; and (9) speeding the development of new drugs by shedding new light on drug-induced brain and heart activity patters.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for assessing a condition of a first organism having body waves corresponding to states of the organism, the method comprising:
   recording first signals corresponding to a body wave, output by a portion of the first organism in a first state, to provide a first record;
   recording the first signals, during a time period in which the first organism is in a second state, to provide a second record;
   processing the first and second records by applying feature expansion procedures thereto; and
   evaluating results of the feature expansion procedures to identify first selected feature expansion procedures effective to distinguish values of the first signals corresponding to the first state from values of the first signals corresponding to the second state.

2. The method of claim 1, further comprising providing a signal interpretation map reflecting the first selected feature expansion procedures.

3. The method of claim 1, further comprising:
   recording a third record corresponding to a third state;
   applying the first selected feature expansion procedures;
   classifying the third state as correlating to one of the first and second states.

4. The method of claim 3, wherein the third state is selected from:
   a condition selected to be comparable to one of the first and second states of the first organism;
   an unidentified state of the first organism;
   an unidentified state resulting from a second organism, distinct from the first organism, being in a condition to be compared to one of the first and second states of the first organism; and
   an unidentified state of the second organism.

5. The method of claim 1, further comprising:
   providing a third record extending over a time period corresponding to transition of the organism between the first and second states; and
   applying the first selected feature expansion procedures.

6. The method of claim 5, further comprising identifying a transition time corresponding to a transition between the first and second states.

7. The method of claim 6, wherein identifying a transition time further comprises creating an activation value plot reflecting classifications of portions of the third record as corresponding to the first and second states.

8. The method of claim 7, wherein identifying further comprises determining a time after which the third record reflects that transition is substantially complete between the first and second states.

9. The method of claim 1, further comprising administering a chemical compound to the first organism.

10. The method of claim 9, wherein the first state corresponds to a first amount of the chemical compound and the second state corresponds to a second amount of the chemical compound.

11. The method of claim 9, wherein the first state corresponds to a first time after administration of the chemical compound, and the second state corresponds to a second time after administration of the chemical compound.

12. The method of claim 9, wherein the first state corresponds to a first chemical compound, and the second state corresponds to a second chemical compound.

13. The method of claim 9, wherein the first state corresponds to a first time, previous to administration of the chemical compound, and the second state corresponds to a second time, after administration of the chemical compound.

14. The method of claim 9, wherein the chemical compound is unapproved by a responsible regulatory agency as a therapeutic.

15. The method of claim 1, further comprising providing a signal interpretation map reflecting the selected feature expansion procedures.

16. The method of claim 1, wherein processing further comprises:
   recording expansion values output from a feature expansion process applied to the first and second records;
   classifying the expansion values in accordance with the correspondence thereof to the first and second states;
   comparing a first set of expansion values corresponding to the first state against a second set of expansion values corresponding to the second state; and
   selecting a threshold value effective to distinguish expansion values corresponding to the first state from expansion values corresponding to the second state.

17. The method of claim 16, further comprising generating a similarity matrix reflecting correspondence between records associated with the first, second, third, and fourth states.

18. The method of claim 1, further comprising:
   recording second signals corresponding to third and fourth states;
   making third and fourth records corresponding to the third and fourth states, respectively;
   processing the third and fourth records; and
   evaluating the processing of the third and fourth records to identify second selected feature expansion procedures effective to distinguish values of the second signals corresponding to the third state from values of the second signals corresponding to the fourth state.

19. The method of claim 1 wherein the organism is selected from a plant, an animal, a human, and a microbe.

20. A method for predicting the physiological effect of a compound on an organism, the method comprising:
   providing a signal interpretation map corresponding to a first compound and a first organism;
   administering a test compound to the first organism:
   monitoring signals propagated from the first organism;
   analyzing the signals using first selected feature expansion procedures to form signal feature expansions corresponding to the signals;
   classifying the signals in accordance with the signal interpretation map applied to the signal feature expansions; and
   predicting a physiological effect of the test compound on the organism based on the classifying.

* * * * *